US012779208B2

(12) United States Patent
Staats et al.

(10) Patent No.: US 12,779,208 B2
(45) Date of Patent: Nov. 3, 2026

(54) NERVE STIMULATION THERAPY FOR MAINTAINING TELOMERE LENGTHS

(71) Applicant: ELECTROCORE, INC, Rockaway, NJ (US)

(72) Inventors: Peter Staats, Atlantic Beach, FL (US); Bruce J. Simon, Mountain Lakes, NJ (US); Joseph P. Errico, Palm Beach Gardens, FL (US)

(73) Assignee: ELECTROCORE INC., Rockaway, NJ (US)

( * ) Notice: Subject to any disclaimer, the term of this patent is extended or adjusted under 35 U.S.C. 154(b) by 0 days.

(21) Appl. No.: 17/731,393

(22) Filed: Apr. 28, 2022

(65) Prior Publication Data

US 2022/0323745 A1 Oct. 13, 2022

Related U.S. Application Data

(63) Continuation-in-part of application No. 17/491,313, filed on Sep. 30, 2021, now Pat. No. 11,590,341, and (Continued)

(51) Int. Cl.
*A61N 1/18* (2006.01)
*A61N 1/04* (2006.01)
*A61N 1/36* (2006.01)

(52) U.S. Cl.
CPC ......... *A61N 1/0456* (2013.01); *A61N 1/0492* (2013.01); *A61N 1/36034* (2017.08)

(58) Field of Classification Search
CPC ................ A61N 1/0456; A61N 1/0551; A61N 1/36053; A61N 1/36034
See application file for complete search history.

(56) References Cited

U.S. PATENT DOCUMENTS 3,590,810 A 7/1971 Kopecky
4,196,737 A 4/1980 Bevilacqua
(Continued)

FOREIGN PATENT DOCUMENTS

EP 1967226 9/2008
EP 2777764 8/2015
(Continued)

OTHER PUBLICATIONS

Greicius et al., Functional connectivity in the resting brain: A network analysis of the default mode hypothesis, PNAS, Jan. 2003, vol. 100, No. 1, pp. 253-258.
(Continued)

*Primary Examiner* — Michael J D'Abreu
(74) *Attorney, Agent, or Firm* — Farber LLC

(57) ABSTRACT

Systems, devices and methods are provided for delivering electrical impulses to the vagus nerve to inhibit the reduction of telomere lengths in cellular DNA, thereby potentially increasing an individual's longevity and/or healthspan. A method comprises positioning a contact surface of a device in contact with an outer skin surface of a patient. An electrical impulse is applied transcutaneously from the device through the outer skin surface of the patient to a vagus nerve in the patient according to a stimulation protocol. The stimulation protocol includes at least two doses administered each day for a plurality of day. The doses each have a duration of about 60 seconds to about 5 minutes, preferably about 90 seconds to 3 minutes. The electrical impulse and the stimulation protocol are sufficient to modulate the vagus nerve such that such that the rate of telomere shortening in the patient's cellular DNA is reduced.

14 Claims, 25 Drawing Sheets

Related U.S. Application Data a continuation-in-part of application No. 17/471,962, filed on Sep. 10, 2021, now Pat. No. 11,894,148, said application No. 17/491,313 is a continuation-in-part of application No. 16/838,953, filed on Apr. 2, 2020, which is a continuation-in-part of application No. 16/229,299, filed on Dec. 21, 2018, now Pat. No. 11,581,090.

(60) Provisional application No. 62/609,807, filed on Dec. 22, 2017.

(56) References Cited

U.S. PATENT DOCUMENTS

| | | | | |
|---|---|---|---|---|
| 4,989,605 | A | 2/1991 | Rossen | |
| 5,109,847 | A | 5/1992 | Liss et al. | |
| 5,458,141 | A | 10/1995 | Neil | |
| 5,487,759 | A | 1/1996 | Bastyr et al. | |
| 5,782,874 | A | 7/1998 | Loos | |
| 5,899,922 | A | 5/1999 | Loos | |
| 5,983,131 | A | 11/1999 | Weaver et al. | |
| 6,104,956 | A | 8/2000 | Naritoku et al. | |
| 6,341,236 | B1 | 1/2002 | Osorio et al. | |
| 6,366,814 | B1 | 4/2002 | Boveja et al. | |
| 6,463,327 | B1 | 10/2002 | Lurie et al. | |
| 6,587,719 | B1 | 7/2003 | Barrett et al. | |
| 6,610,713 | B2 | 8/2003 | Tracey | |
| 6,631,297 | B1 | 10/2003 | Mo | |
| 7,254,444 | B2 | 8/2007 | Moore | |
| 7,734,340 | B2 | 6/2010 | De Ridder | |
| 7,797,041 | B2 | 9/2010 | Libbus et al. | |
| 2002/0099417 | A1 | 7/2002 | Naritoku et al. | |
| 2002/0183237 | A1 | 12/2002 | Puskas | |
| 2002/0183804 | A1 | 12/2002 | Malaney et al. | |
| 2003/0212311 | A1 | 11/2003 | Nova et al. | |
| 2004/0073271 | A1 | 4/2004 | Harry et al. | |
| 2004/0243182 | A1 | 12/2004 | Cohen et al. | |
| 2004/0249416 | A1 | 12/2004 | Yun et al. | |
| 2005/0021092 | A1 | 1/2005 | Yun et al. | |
| 2005/0065553 | A1* | 3/2005 | Ben Ezra | A61N 1/36053 607/2 |
| 2005/0065574 | A1 | 3/2005 | Rezai | |
| 2005/0113630 | A1 | 5/2005 | Fox et al. | |
| 2005/0137644 | A1 | 6/2005 | Boveja et al. | |
| 2005/0165458 | A1 | 7/2005 | Boveja | |
| 2005/0187590 | A1 | 8/2005 | Boveja et al. | |
| 2005/0216062 | A1 | 9/2005 | Herbst | |
| 2005/0267544 | A1 | 12/2005 | Lee et al. | |
| 2005/0278001 | A1 | 12/2005 | Qin et al. | |
| 2006/0015153 | A1 | 1/2006 | Gliner et al. | |
| 2006/0074284 | A1 | 4/2006 | Juola et al. | |
| 2006/0074450 | A1 | 4/2006 | Boveja et al. | |
| 2006/0100668 | A1 | 5/2006 | Ben-David et al. | |
| 2006/0100671 | A1 | 5/2006 | Ridder | |
| 2006/0173510 | A1 | 8/2006 | Besio et al. | |
| 2006/0178703 | A1* | 8/2006 | Huston | A61N 1/36053 607/2 |
| 2007/0027496 | A1 | 2/2007 | Parnis et al. | |
| 2007/0038264 | A1 | 2/2007 | Jaax et al. | |
| 2007/0106337 | A1 | 5/2007 | Errico et al. | |
| 2007/0123952 | A1 | 5/2007 | Strother et al. | |
| 2007/0142886 | A1 | 6/2007 | Fischell et al. | |
| 2007/0150006 | A1 | 6/2007 | Libbus et al. | |
| 2007/0156182 | A1 | 7/2007 | Castel et al. | |
| 2007/0250145 | A1 | 10/2007 | Kraus et al. | |
| 2007/0276449 | A1 | 11/2007 | Gunter et al. | |
| 2008/0021512 | A1 | 1/2008 | Knudson et al. | |
| 2008/0027513 | A1 | 1/2008 | Carbunaru | |
| 2008/0045776 | A1 | 2/2008 | Fischell et al. | |
| 2008/0077192 | A1 | 3/2008 | Harry et al. | |
| 2008/0114199 | A1 | 5/2008 | Riehl et al. | |
| 2008/0132964 | A1 | 6/2008 | Cohen et al. | |
| 2008/0177190 | A1 | 7/2008 | Libbus et al. | |
| 2008/0208266 | A1 | 8/2008 | Lesser et al. | |
| 2008/0306325 | A1 | 12/2008 | Burnett et al. | |
| 2009/0036945 | A1 | 2/2009 | Chancellor | |
| 2009/0099622 | A1 | 4/2009 | Fowler | |
| 2009/0105782 | A1* | 4/2009 | Mickle | A61N 1/36053 607/45 |
| 2009/0112283 | A1 | 4/2009 | Kriksunov et al. | |
| 2009/0132018 | A1 | 5/2009 | DiUbaldi et al. | |
| 2009/0157149 | A1 | 6/2009 | Wahlgren et al. | |
| 2009/0182393 | A1 | 7/2009 | Bachinski | |
| 2009/0234417 | A1 | 9/2009 | Pastena et al. | |
| 2009/0234419 | A1 | 9/2009 | Maschino et al. | |
| 2009/0240297 | A1 | 9/2009 | Shavit et al. | |
| 2009/0287035 | A1 | 11/2009 | Dietrich et al. | |
| 2010/0030299 | A1 | 2/2010 | Covalin | |
| 2010/0069995 | A1* | 3/2010 | Danielsson | A61N 1/36114 607/50 |
| 2010/0152794 | A1 | 6/2010 | Radivojevic et al. | |
| 2010/0152811 | A1 | 6/2010 | Flaherty | |
| 2010/0286553 | A1 | 11/2010 | Feler et al. | |
| 2011/0046432 | A1 | 2/2011 | Simon et al. | |
| 2011/0152967 | A1 | 6/2011 | Simon et al. | |
| 2011/0213295 | A1 | 9/2011 | Henley et al. | |
| 2011/0224749 | A1 | 9/2011 | Ben-David et al. | |
| 2011/0230701 | A1 | 9/2011 | Simon et al. | |
| 2011/0319958 | A1* | 12/2011 | Simon | A61N 2/006 607/42 |
| 2012/0029601 | A1 | 2/2012 | Simon et al. | |
| 2012/0283697 | A1 | 11/2012 | Kim et al. | |
| 2012/0303080 | A1 | 11/2012 | Ben-David et al. | |
| 2013/0006322 | A1 | 1/2013 | Tai | |
| 2013/0060304 | A1 | 3/2013 | LaTendresse et al. | |
| 2013/0245486 | A1 | 9/2013 | Simon et al. | |
| 2014/0005743 | A1 | 1/2014 | Giuffrida et al. | |
| 2014/0031895 | A1 | 1/2014 | Rahimi | |
| 2014/0172041 | A1 | 6/2014 | Draghici | |
| 2014/0222102 | A1 | 8/2014 | Lemus | |
| 2014/0236040 | A1 | 8/2014 | Moon | |
| 2014/0257438 | A1* | 9/2014 | Simon | A61N 2/02 607/150 |
| 2015/0165226 | A1 | 6/2015 | Simon et al. | |
| 2015/0190637 | A1 | 7/2015 | Simon et al. | |
| 2019/0111255 | A1* | 4/2019 | Errico | A61N 2/02 |
| 2019/0111263 | A1* | 4/2019 | Levine | A61B 5/388 |
| 2019/0232047 | A1* | 8/2019 | Chu | A61H 23/00 |

FOREIGN PATENT DOCUMENTS

| | | | |
|---|---|---|---|
| JP | 2006-515192 | 11/2006 | |
| JP | 2009-125263 | 6/2009 | |
| JP | 2012-52385 | 9/2013 | |
| JP | 2014-510586 | 5/2014 | |
| KR | 101242190 | 3/2013 | |
| WO | WO1993/01862 | 2/1993 | |
| WO | WO2005/007120 | 1/2005 | |
| WO | WO2007/092062 | 8/2007 | |
| WO | WO2007/149811 | 12/2007 | |
| WO | WO2008/042902 | 4/2008 | |
| WO | WO2007/058780 | 5/2008 | |
| WO | WO-2008112915 A1 * | 9/2008 | A61H 23/00 |
| WO | WO2009/021080 | 2/2009 | |
| WO | WO2009/064641 | 5/2009 | |
| WO | WO2009/135693 | 11/2009 | |
| WO | WO2012/121750 | 9/2012 | |
| WO | WO 2012/174330 | 12/2012 | |
| WO | WO2013/066135 | 5/2013 | |

OTHER PUBLICATIONS

Heneka et al., Locus ceruleus controls Alzheimer's disease pathology by modulating microglial functions through norepinephrine, PNAS, Mar. 2010, vol. 107, No. 13, pp. 6058-6063.

Lee et al., Clustering of Resting State Networks, PLoS One, Jul. 2012, vol. 7, Issue 7, pp. 1-12.

Miyoshi, K. and Morimura, Y. "Clinical Manifestations of Neuropsychiatric Disorders," 2010, Neuropsychiatric Disorders, Springer, XIV, pp. 1-15.

(56) References Cited

OTHER PUBLICATIONS

International Search Report and Written Opinion dated Aug. 25, 2015 in related Application No. PCT/US15/31847 filed May 20, 2015 (10 pages).
International Search Report and Written Opinion dated May 8, 2007 in related PCT Application No. PCT/US2006/042823 filed Nov. 2, 2006 (5 pages).
International Search Report and Written Opinion dated Sep. 17, 2007 in related PCT Application No. PCT/US2006/042828 filed Nov. 2, 2006 (5 pages).
International Search Report and Written Opinion dated Mar. 26, 2008 in related PCT Application No. PCT/US2006/042752 filed Nov. 1, 2006 (7 pages).
International Search Report and Written Opinion dated Dec. 22, 2011 in related PCT Application No. PCT/US2011/049844 filed Aug. 31, 2011 (9 pages).
International Search Report and Written Opinion dated Apr. 30, 2013 in related PCT Application No. PCT/US2013/023014 filed Jan. 24, 2013 (7 pages).
International Search Report and Written Opinion dated Dec. 11, 2013 in related PCT Application No. PCT/US2013/058079 filed Sep. 4, 2013 (8 pages).
International Search Report and Written Opinion dated Jan. 29, 2014 in related PCT Application No. PCT/US2013/068804 filed Nov. 6, 2013 (10 pages).
Europe Office Action dated Apr. 24, 2018 in related Application No. 15796247.3 filed May 20, 2015 (6 pages).
Europe Office Action dated Jul. 26, 2018 in related Application No. 11818591.7 filed Aug. 12, 2011 (8 pages).

* cited by examiner

NERVE STIMULATION THERAPY FOR MAINTAINING TELOMERE LENGTHS

CROSS REFERENCE TO RELATED APPLICATIONS

This patent application is a Continuation-In-Part of U.S. Nonprovisional application Ser. No. 17/471,962, filed Sep. 10, 2021 and a Continuation-In-Part of U.S. Nonprovisional application Ser. No. 17,491,313, filed Sep. 30, 2021, which is a Continuation-In-Part of U.S. Nonprovisional application Ser. No. 16/838,953, filed Apr. 2, 2020, which is a Continuation-in-Part of U.S. Nonprovisional application Ser. No. 16/229,299 filed Dec. 21, 2018; which claims the benefit of U.S. Provisional application No. 62/609,807 filed Dec. 22, 2017; all of which are hereby incorporated by reference for all purposes as if copied and pasted herein.

This patent application is also related to the following commonly-assigned patents and patent applications: U.S. Nonprovisional application Ser. No. 14/335,726 filed Jul. 18, 2014, U.S. Nonprovisional application Ser. No. 14/292,491 filed May 30, 2014, now U.S. Pat. No. 9,375,571 issued Jun. 28, 2016, U.S. Nonprovisional application Ser. No. 13/858,114 filed Apr. 8, 2013, now U.S. Pat. No. 9,248,286 issued Feb. 2, 2016, U.S. Nonprovisional application Ser. No. 14/930,490 filed Nov. 2, 2015, U.S. Nonprovisional application Ser. No. 13/222,087 filed Aug. 31, 2011, now U.S. Pat. No. 9,174,066 issued Nov. 3, 2015, U.S. Nonprovisional application Ser. No. 13/183,765 filed Jul. 15, 2011, now U.S. Pat. No. 8,874,227 issued Oct. 28, 2014, U.S. Nonprovisional application Ser. No. 13/183,721 filed Jul. 15, 2011, now U.S. Pat. No. 8,676,324 issued Mar. 18, 2014, U.S. Nonprovisional application Ser. No. 13/109,250 filed May 17, 2011, now U.S. Pat. No. 8,676,330 issued Mar. 18, 2014, U.S. Nonprovisional application Ser. No. 13/075,746 filed Mar. 30, 2011, now U.S. Pat. No. 8,874,205 issued Oct. 28, 2014, U.S. Nonprovisional application Ser. No. 13/005,005 filed Jan. 12, 2011, now U.S. Pat. No. 8,868,177 issued Oct. 21, 2014, U.S. Nonprovisional application Ser. No. 12/964,050 filed Dec. 9, 2010, U.S. Nonprovisional application Ser. No. 12/859,568 filed Aug. 19, 2010, now U.S. Pat. No. 9,037,247 issued May 19, 2015, U.S. Nonprovisional application Ser. No. 12/612,177 filed Nov. 4, 2009, now U.S. Pat. No. 8,041,428 issued Oct. 18, 2011, U.S. Nonprovisional application Ser. No. 12/408,131 filed Mar. 20, 2009, now U.S. Pat. No. 8,812,112 issued Aug. 19, 2014, U.S. Nonprovisional application Ser. No. 15/149,406 filed May 9, 2016, U.S. Nonprovisional application Ser. No. 14/337,930 filed Jul. 22, 2014, now U.S. Pat. No. 9,333,347 issued May 10, 2016, U.S. Nonprovisional application Ser. No. 13/075,746 filed Mar. 30, 2011, now U.S. Pat. No. 8,874,205 issued Oct. 28, 2014, U.S. Nonprovisional application Ser. No. 12/964,050 filed Dec. 9, 2010, U.S. Nonprovisional application Ser. No. 12/859,568 filed 19 Aug. 2010, now U.S. Pat. No. 9,037,247 issued May 19, 2015, U.S. Nonprovisional application Ser. No. 14/462,605 filed Aug. 19, 2014, U.S. Nonprovisional application Ser. No. 13/005,005 filed Jan. 12, 2011, now U.S. Pat. No. 8,868,177 issued Oct. 21, 2014, U.S. Nonprovisional application Ser. No. 12/964,050 filed Dec. 9, 2010, U.S. Nonprovisional application Ser. No. 12/859,568 filed Aug. 19, 2010 now U.S. Pat. No. 9,037,247 issued May 19, 2015 and U.S. Nonprovisional application Ser. No. 12/408,131 filed Mar. 20, 2009 now U.S. Pat. No. 8,812,112 issued Aug. 19, 2014; all of which are hereby incorporated by reference for all purposes as if copied and pasted herein.

BACKGROUND

Ageing is the process of becoming older and is usually associated with dynamic changes in the biological, psychological, physiological, environmental, behavioral and social processes. In humans, ageing represents the accumulation of changes in a human being over time and can encompass physical, psychological, and social changes. Reaction time, for example, may slow with age, while memories and general knowledge typically increase. Ageing increases the risk of human diseases such as cancer, Alzheimer's disease, diabetes, cardiovascular disease, stroke and many more. Of the roughly 150,000 people who die each day across the globe, about two-thirds die from age-related causes.

Ageing not only impacts the lifespan of an individual, but also his or her healthspan. Healthspan is generally defined as the period of one's life that one is healthy, or free from serious disease. A disease is "serious" if it is a leading cause of death, which may include heart disease, lung, colorectal, breast or prostate cancer, COPD, stroke, lower respiratory infections, Alzheimer's disease, Type 2 diabetes and the like. If any individual has lived beyond his or her healthspan, they are generally chronically sick, often with a degenerating condition.

The factors proposed to influence biological ageing that reduce both lifespan and healthspan fall into two main categories: programmed and damage-related. Programmed factors follow a biological timetable, perhaps one that might be a continuation of the one that regulates childhood growth and development. This regulation would depend on changes in gene expression that affect the systems responsible for maintenance, repair and defense responses. Damage-related factors include internal and environmental assaults to living organisms that induce cumulative damage at various levels.

Programmed aging is at least partially associated with telomere shortening in the cells of the body. Telomeres, the specific DNA—protein structures found at both ends of each chromosome, protect genome from nucleolytic degradation, unnecessary recombination, repair, and intrachromosomal fusion. Telomeres therefore play a vital role in preserving the information in our genome. As a normal cellular process, a small portion of telomeric DNA is lost with each cell division. When telomere length reaches a critical limit, the cell undergoes senescence and/or apoptosis. Telomere length may therefore serve as a biological clock to determine the lifespan of a cell and an organism.

The primary mechanism of telomere length maintenance and lengthening is via the enzyme telomerase, which is active at high levels in germline and cancer cells, and at low levels in peripheral blood mononucleocytes (PBMCs). Telomerase, also called terminal transferase, is a ribonucleoprotein that adds a species-dependent telomere repeat sequence to the 3' end of telomeres. Telomerase protects the end of the chromosome from DNA damage or from fusion with neighboring chromosomes.

One of the key factors that negatively impacts the effectiveness of telomerase in maintaining telomere length is chronic stress. Chronic stress occurs when the body experiences stressors with such frequency or intensity that the autonomic nervous system does not have an adequate chance to activate the relaxation response on a regular basis. This means that the body remains in a constant state of physiological arousal. Chronic stress has been reported to accelerate ageing and the onset of age-related disease and has been directly linked to telomere shortening.

Acute stress generally prompts the adrenal glands to release a surge of hormones, including adrenaline and cortisol. Adrenaline increases your heart rate, elevates your blood pressure and boosts energy supplies. Cortisol, the primary stress hormone, increases sugars (glucose) in the bloodstream, enhances your brain's use of glucose and increases the availability of substances that repair tissues. Cortisol also curbs functions that would be nonessential or harmful in a fight-or-flight situation. It alters immune system responses and suppresses the digestive system, the reproductive system and growth processes. This complex natural alarm system also communicates with the brain regions that control mood, motivation and fear.

The body's stress response is usually self-limiting. Once a perceived threat or other stressor has based, hormone levels return to normal. But when these stressors persist, the "fight-or-flight" reaction remains turned on and adrenaline and cortisol levels remain high. This long-term activation of the stress response system and the overexposure to cortisol and other stress hormones that follows can disrupt almost all the body's processes and can accelerate telomere shortening and thus the ageing process.

What is needed, therefore, are improved systems and methods for maintaining telomere length to increase an individual's longevity and/or healthspan. In particular, it is desirable to provides systems and method that reduce systemic inflammation and/or chronic levels of cortisol or other stress hormones in the body to increase the effectiveness of telomerase in maintaining the length of telomeres in the cell's DNA, thereby increasing the length of time an individual may live a healthy life free from serious disease.

SUMMARY

This disclosure relates generally to the delivery of electrical impulses to bodily tissues for therapeutic purposes, and more specifically to vagal nerve stimulation devices designed to maintain telomere lengths in cellular DNA to potentially increase an individual's lifespan and/or healthspan.

In one aspect, a method comprises positioning a contact surface of a device in contact with an outer skin surface of a patient. An electrical impulse is applied transcutaneously from the device through the outer skin surface of the patient to a vagus nerve in the patient according to a stimulation protocol. The stimulation protocol includes at least two doses administered each day for a plurality of day. The doses each have a duration of about 60 seconds to about 5 minutes, preferably about 90 seconds to 3 minutes. The electrical impulse and the stimulation protocol are sufficient to modulate the vagus nerve to inhibit the reduction of telomere lengths in cellular DNA.

Vagal nerve stimulation with the specific stimulation protocol described herein may directly or indirectly increase an activity of telomerase within the patient. Increasing telomerase activity protects the end of the chromosome from DNA damage or from fusion with neighboring chromosomes, thereby maintaining the length of the telomeres or at least inhibiting the natural reduction of telomeres.

Inhibiting the reduction of telomere lengths may potentially increase the lifespan or healthspan on an individual. Lifespan as defined herein as the duration of life of an individual. Healthspan is defined herein as the period of one's life that one is substantially free from serious disease. A disease is "serious" if it is a leading cause of death, which includes heart disease, lung, colorectal, breast or prostate cancer, COPD, stroke, lower respiratory infections, Alzheimer's disease and Type 2 diabetes.

In certain embodiments, the electrical impulse and the stimulation protocol are sufficient to modulate the vagus nerve to reduce a cortisol level within the patient, particularly the amount of circulating cortisol within the patient. Thus, devices and methods provided herein increase the ability of the parasympathetic nerve to adapt to upward regulation and stress. This not only provides a mechanism for stress control, but mitigates the impact of chronic stress by reducing the levels of circulating cortisol. Reducing these levels of cortisol deaccelerates telomere shortening and thus the ageing process.

In other embodiments, the electrical impulse is sufficient to reduce systemic inflammation. Similar to chronic stress, systemic inflammation has been linked to reduced telomerase effectiveness. The electrical impulse may be sufficient to suppress inflammatory cytokine levels via activation of the Cholinergic Anti-inflammatory Pathway (CAP). The CAP is believed to be the efferent vagus nerve-based arm of the inflammatory reflex, mediated through vagal efferent fibers that synapse onto enteric neurons, which release acetylcholine (Ach) at the synaptic junction with macrophages. Stimulation of the CAP leads to Ach binding to $\alpha$-7-nicotinic ACh receptors ($\alpha$7nAChR), resulting in reduced production of the inflammatory cytokines TNF-a, IL-1b, and IL-6, but not the anti-inflammatory cytokine, IL-10.

In other embodiments, the electrical impulse is sufficient to directly inhibit a release of a pro-inflammatory cytokine, such as necrosis factor (TNF)-alpha and IL-1$\beta$. These cytokines are typically elevated in certain patients suffering from chronic stress or anxiety.

In other embodiments, the electrical impulse is sufficient to increase the anti-inflammatory competence of certain cytokines to thereby offset or reduce the effect of pro-inflammatory cytokines.

In some embodiments, the doses are separated by a time frame of about 1 hour to about 12 hours. The stimulation protocol may comprise 2 to 12 treatments/day. In certain embodiments, the doses are separated by a time frame of about five to 15 minutes. In other embodiments, the method comprises administered two doses consecutively and then continuing to administer two doses multiple times/day. In still other embodiments, the doses may be separated by at least one hour, or between about four to about 12 hours. The stimulation protocol may comprise 2 to 12 treatments/day, preferably between about 2 to 4 treatments.

The device may comprise one or more electrodes that are adhered, or otherwise attached to, the outer skin surface of a neck of the patient. This allows the patient to be treated without direct intervention (i.e., holding a device or the electrodes against the patient's neck during stimulation). The system may further comprise an outer sheath or other wearable device, such as a insulating strip, a collar, or a garment, such as a turtleneck, a scarf or the like, that functions to adhere the electrodes to the neck of the patient. The electrodes may be housed within the wearable device, or positioned between the wearable device and the neck of the patient.

In some embodiments, the electrodes are coupled to a source via one or more leads such that the electrical impulse is transmitted to the electrodes from an energy source through the leads. In other embodiments, the method further comprises wirelessly transmitting the electrical impulse to the one or more electrodes. In yet another embodiment, the electrodes are part of a housing, such as a handheld device, that contains the energy source.

In an alternative embodiment, the device comprises a patch that includes at least one adhesive surface for attachment to the outer skin surface of the neck of the patient. The electrodes are housed within the patch. The patch may further comprise a signal generator and an energy source for applying the electrical impulses through the electrodes to the vagus nerve. Alternatively, the patch may include a wireless receiver and associated electronics for wirelessly receiving the electrical impulse and/or the energy from the energy source.

In certain embodiments, the electrical impulse comprises pulses having a frequency of about 1 kHz to about 20 kHz. The electrical impulse may comprise bursts of pulses, with each burst having a frequency of about 1 to about 100 bursts per second and each pulse has a duration of about 50 to about 1000 microseconds in duration. The bursts each comprise about 2 to 20 pulses and the bursts are separated by an inter-burst period that comprises zero pulses.

In another aspect, a device comprises one or more electrodes configured for contacting an outer skin surface of the patient. An energy source is coupled to the electrodes. The energy source is configured to generate at least one electrical impulse and to transmit the at least one electrical impulse transcutaneously from the electrodes through the outer skin surface of the patient to a vagus nerve in the patient according to a stimulation protocol. The stimulation protocol includes at least two 90 second to two minute doses administered each day for a plurality of days. The electrical impulse and the stimulation protocol are sufficient to modulate the vagus nerve to inhibit the reduction of telomere lengths in cellular DNA.

In certain embodiments, the one or more electrodes are configured for attachment to the outer skin surface of the neck of the patient such that the stimulation protocol may be administered to the patient without self-treatment. This allows for treatment to occur even when the patient is unable or unwilling to comply with the treatment regimen. The energy source may be wirelessly coupled to the one or more electrodes. Alternatively, the device further comprises one or more electrical connectors or lead wires coupling the energy source to the one or more electrodes.

In other embodiments, the device further comprises a housing, such as a handheld device, that may be operated by the patient. The energy source is housed within the housing and the electrodes are attached to, or incorporated into, the housing.

In other embodiments, the device comprises a patch having at least one adhesive surface for attachment to the outer skin surface of the neck of the patient. The electrodes are housed within the patch. The patch may further comprise a signal generator and an energy source for applying the electrical impulses through the electrodes to the vagus nerve. Alternatively, the patch may include a wireless receiver and associated electronics for wirelessly receiving the electrical impulse and/or the energy from the energy source.

The device may further comprise a controller coupled to the energy source and configured to transmit parameters for the stimulation protocol to the energy source. The controller and/or the energy source may be wirelessly coupled to the electrodes, or each other. Alternatively, the controller and the energy source may be housed within the patch or the handheld device.

In one embodiment, the electrical impulse is transmitted for at least 30 seconds within 4 hours of a commencement of symptoms in the patient. The electrical impulse may be applied in a single dose for a time period of about 30 seconds and about 3 minutes, preferably about 90-150 seconds, or it may be applied in a series of doses each having a time period of about 30 seconds to about 3 minutes, preferably about 90-150 seconds in each dose. The series of doses may be applied every 5 to 30 minutes, preferably every 10 to 20 minutes, and more preferably every 15 minutes, for a period of at least 1 hour, preferably at least 2 hours and more preferably about 3 hours. Each dose may be further applied every 6 to 10 hours for a period of at least 2 to 10 days, preferably about 2 to 5 days.

In another embodiment, the electrical impulse is applied in a first dose for a time period of about 30 seconds and about 3 minutes, preferably about 90-150 seconds and then a second dose for a time period of about 30 seconds and about 3 minutes, preferably about 90-150 seconds. The electrical impulse may be transmitted in a series of first and second doses, wherein the electrical impulse is applied for a time period of about 30 seconds to about 3 minutes (preferably about 90-150 seconds) in each of the first and second doses. The first and second doses may be applied every 10 to 30 minutes (preferably about every 15 minutes) for a period of at least at least 1 hour, preferably at least 2 hours and more preferably about 3 hours. Each dose may be further applied every 6 to 10 hours for a period of at least 2 to 10 days, preferably for about 2 to 5 days.

In certain embodiments, the energy source is wirelessly coupled to the one or more electrodes. In other embodiments, the energy source is coupled to the electrodes directly with electrical connectors. In yet other embodiments, the energy source and the electrodes are housing within a handheld device that can be placed or attached against the outer surface of the patient's neck.

In one such embodiment, the electrodes are adhered to the outer skin surface of the patient's neck with a suitable adhesive. This allows the patient to be treated without direct intervention (i.e., holding a device or the electrodes against the patient's neck during stimulation). The system may further comprise an outer sheath or other wearable device, such as a insulating strip, a collar, or a garment, such as a turtleneck, a scarf or the like, that functions to adhere the electrodes to the neck of the patient. The electrodes may be housed within the wearable device, or positioned between the wearable device and the neck of the patient.

In certain embodiments, the method may further comprise providing parameters for a stimulation protocol to the energy source. The parameters may include the treatment regimen described above, or they may include other parameters, such as the voltage, amplitude, duty cycle, frequency or duration of the electrical impulse or the overall electrical stimulation. Alternatively or additionally, the position and/or orientation of the stimulation device on the patient's neck may be adjusted based on the physiological parameter. In certain embodiments, the device may be alternated between the right and left side of the patient's neck to optimize the signal based on the measurement of physiological parameters.

In certain embodiments, the method further comprises measuring one or more physiological parameters of the patient associated with the electrical impulse and modifying the parameters of the electrical impulse based on the physiological parameter. Physiogical parameters may include, for example, blood flow associated with a nerve, such as vagal artery or cerebral blood flow, heart rate variability, selected biomarkers or other chemicals, a property of a voice of the patient, a laryngeal electromyographic signal, an electroglottographic signal, a property of the autonomic nervous system and the like. The one or more electrodes may comprise two electrodes that are either attached to each other, or separate from each other. In certain embodiments, the system comprises multiple sets of electrodes that can be positioned at different locations on a patient's neck. The controller is configured to determine, based on detection of a physiological response, which set or sets of electrodes produce optimal results, e.g., stimulation of the vagus nerve. In this embodiment, the controller is configured to direct the electrical impulses from the energy source to the optimally positioned electrodes on the neck of the patient.

In certain embodiments, the electrical impulse comprises pulses having a frequency of about 1 kHZ to about 10 kHz. The electrical impulse may comprise bursts of pulses, with each burst having a frequency of about 1 to about 100 bursts per second or about 15 to 50 bursts per second and each pulse has a duration of about 50 to about 1000 microseconds in duration. The bursts may comprise about 2 to 20 pulses and the bursts may be separated by an inter-burst period that comprises zero pulses, such that the inter-burst period has a constant electric field. The constant electric field may have a magnitude of zero.

Various technologies for preventing, diagnosing, monitoring, ameliorating, or treating medical conditions, diseases, or disorders, such as replicating pathogens, are more completely described in the following detailed description, with reference to the drawings provided herewith, and in claims appended hereto. Other aspects, features, advantages, etc. will become apparent to one skilled in the art when the description is taken in conjunction with the accompanying drawings.

INCORPORATION BY REFERENCE

Hereby, all issued patents, published patent applications, and non-patent publications that are mentioned in this specification are herein incorporated by reference in their entirety for all purposes as if copied and pasted herein, to the same extent as if each individual issued patent, published patent application, or non-patent publication were specifically and individually indicated to be incorporated by reference and copied and pasted into this disclosure.

DETAILED DESCRIPTION

Figure 1:
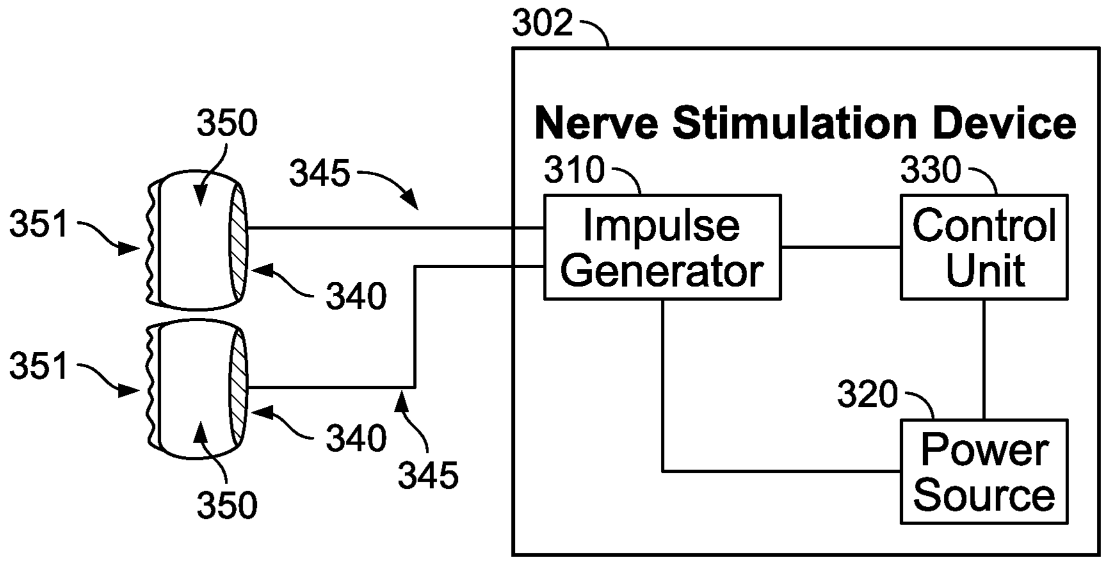
FIG. 1 illustrates a schematic view of one embodiment of a nerve modulating system according to the present disclosure.

Generally, this disclosure relates to the delivery of electrical impulses (and/or fields) to bodily tissues for therapeutic purposes, and more specifically to vagal nerve stimulation devices for treating patient's suffering from systemic inflammation or chronic stress, anxiety or other disorders that invoke a chronic stress response resulting from elevated cortisol levels. These elevated cortisol levels may contribute to accelerated shortening of telomere lengths in cellular DNA, such as chronic pain, tumors or other disorders of the pituitary gland, depression, mood disorders, fear, perceived threats to safety, status or well-being, fatigue, irritability, headache, intestinal problems, increased blood pressure, poor sleep and the like. Reduction of these telomere lengths may potentially shorten the overall longevity and/or healthspan of the patient.

Cortisol is a potent anti-inflammatory that functions to mobilize glucose reserves for energy and modulate inflammation. Cortisol also may facilitate the consolidation of fear-based memories for future survival and avoidance of danger. Although short-term stress may be adaptive, maladaptive responses (eg, magnification, rumination, helplessness) to pain or non-pain-related stressors may intensify cortisol secretion and condition a sensitized physiologic stress response that is readily recruited. Ultimately, a prolonged or exaggerated stress response may perpetuate cortisol dysfunction, widespread inflammation, and pain. Stress may be unavoidable in life, and challenges are inherent to success; however, humans have the capability to modify what they perceive as stressful and how they respond to it. Exaggerated psychological responses (eg, catastrophizing) following maladaptive cognitive appraisals of potential stressors as threatening may exacerbate cortisol secretion and facilitate the consolidation of fear-based memories of pain or non-pain-related stressors; however, coping, cognitive reappraisal, or confrontation of stressors may minimize cortisol secretion and prevent chronic, recurrent pain.

Studies have shown that heightened cortisol responsivity to psychological stress is associated with accelerated cellular aging as indexed by leukocyte telomere length. This indicates that heightened cortisol responsivity is not simply a consequence of more advanced cellular aging but may contribute to the cellular aging process. Cortisol also suppresses telomerase activation in immune system cells so that telomeres are no longer protected during cell division and become progressively shorter. This leads to early cell aging and distorted replicas of the original cell that could lead to cancer and other diseases.

Applying vagal nerve stimulation to a patient with a specific treatment protocols described herein may reduce the level of circulating cortisol in the patient. This reduction in chronic cortisol levels may alter the chronic stress response, alleviation the many symptoms associated with such response. In addition, vagal nerve stimulation with the specific stimulation methods and devices described herein may increase an activity of telomerase within the patient. Increasing telomerase activity protects the end of the chromosome from DNA damage or from fusion with neighboring chromosomes, thereby maintaining the length of the telomeres or at least inhibiting the natural reduction of teleomeres.

In certain embodiments, the electrical impulse and the stimulation protocol are sufficient to modulate the vagus nerve to reduce a cortisol level within the patient, particularly the amount of circulating cortisol within the patient. Thus, devices and methods provided herein increase the ability of the parasympathetic nerve to adapt to upward regulation and stress. This not only provides a mechanism for stress control, but mitigates the impact of chronic stress by reducing the levels of circulating cortisol. Reducing these levels of cortisol deaccelerates telomere shortening and thus the ageing process.

In some embodiments, various methods can use vagal nerve stimulation to suppress inflammation, thereby increasing the effectiveness of telomerase to maintain telomere lengths in cellular DNA. In some embodiments, some methods and devices involve the inhibition of pro-inflammatory cytokines, or more specifically, stimulation of the vagus nerve to inhibit and/or block the release of such pro-inflammatory cytokines. In some embodiments, some methods and devices use vagal nerve stimulation to increase the concentration or effectiveness of anti-inflammatory cytokines.

In some embodiments, the devices and methods of the present invention stimulate nerves by transmitting energy to nerves and tissue non-invasively. A medical procedure can be understood as being non-invasive when no break in the skin (or other surface of the body, such as a wound bed) is created through use of the method, and when there is no contact with an internal body cavity beyond a body orifice (e.g., beyond the mouth or beyond the external auditory meatus of the ear). In some ways, such non-invasive procedures can be distinguished from some invasive procedures (including minimally invasive procedures) in that the invasive procedures insert a substance or device into or through the skin (or other surface of the body, such as a wound bed) or into an internal body cavity beyond a body orifice.

Note though that this disclosure is now described more fully with reference to the set of accompanying illustrative drawings, in which example embodiments of this disclosure are shown. This disclosure can be embodied in many different forms and should not be construed as necessarily being limited to the example embodiments disclosed herein. Rather, the example embodiments are provided so that this disclosure is thorough and complete, and fully conveys various concepts of this disclosure to those skilled in a relevant art. For example, the energy impulses (and/or fields) that are used to treat those conditions comprise electrical and/or electromagnetic energy, can be delivered invasively or non-invasively to the patient, particularly to a vagus nerve of the patient.

For example, transcutaneous electrical stimulation of a nerve can be non-invasive because it involves attaching electrodes to the skin, or otherwise stimulating at or beyond the surface of the skin or using a form-fitting conductive garment, without breaking the skin [Thierry KELLER and Andreas Kuhn. Electrodes for transcutaneous (surface) electrical stimulation. Journal of Automatic Control, University of Belgrade 18 (2,2008):35-45, the disclosure of which is incorporated herein by reference for all purposes as if copied and pasted herein; Mark R. PRAUSNITZ. The effects of electric current applied to skin: A review for transdermal drug delivery. Advanced Drug Delivery Reviews 18 (1996)

395-425, the disclosure of which is incorporated herein by reference for all purposes as if copied and pasted herein]. In contrast, percutaneous electrical stimulation of a nerve can be minimally invasive because it involves the introduction of an electrode under the skin, via needle-puncture of the skin.

Another form of non-invasive electrical stimulation is magnetic stimulation. It involves the induction, by a time-varying magnetic field, of electrical fields and current within tissue, in accordance with Faraday's law of induction. Magnetic stimulation can be non-invasive because the magnetic field is produced by passing a time-varying current through a coil positioned outside the body. An electric field is induced at a distance, causing electric current to flow within electrically conducting bodily tissue. The electrical circuits for magnetic stimulators can be generally complex and expensive and use a high current impulse generator that may produce discharge currents of 5,000 amps or more, which is passed through the stimulator coil to produce a magnetic pulse. Some principles of electrical nerve stimulation using a magnetic stimulator, along with descriptions of medical applications of magnetic stimulation, are reviewed in: Chris HOVEY and Reza Jalinous, The Guide to Magnetic Stimulation, The Magstim Company Ltd, Spring Gardens, Whitland, Carmarthenshire, SA34 0HR, United Kingdom, 2006, the disclosure of which is incorporated herein by reference for all purposes as if copied and pasted herein. In contrast, the magnetic stimulators that are disclosed herein are relatively simpler devices that can use considerably smaller currents within the stimulator coils. Accordingly, they are intended to satisfy a need for simple-to-use and less expensive non-invasive magnetic stimulation devices.

Some advantages of some of such non-invasive medical methods and devices relative to comparable invasive procedures are as follows. The patient may be more psychologically prepared to experience a procedure that is non-invasive and may therefore be more cooperative, resulting in a better outcome. Non-invasive procedures may avoid damage of biological tissues, such as that due to bleeding, infection, skin or internal organ injury, blood vessel injury, and vein or lung blood clotting. Non-invasive procedures can be generally measurably painless and may be performed without some of the dangers and costs of surgery. They are ordinarily performed even without the need for local anesthesia. Less training may be required for use of non-invasive procedures by medical professionals. In view of the reduced risk ordinarily associated with non-invasive procedures, some such procedures may be suitable for use by the patient or family members at home or by first-responders at home or at a workplace. Furthermore, the cost of non-invasive procedures may be significantly reduced relative to comparable invasive procedures.

In co-pending, commonly assigned patent applications, the Applicant disclosed some noninvasive electrical vagus nerve stimulation devices, which are adapted, and for certain applications improved, in the present disclosure [application Ser. No. 13/183,765 and Publication US2011/0276112, entitled Devices and methods for non-invasive capacitive electrical stimulation and their use for vagus nerve stimulation on the neck of a patient, to SIMON et al, the disclosure of which is incorporated herein by reference for all purposes as if copied and pasted herein: application Ser. No. 12/964,050 and Publication No. US2011/0125203, entitled Magnetic Stimulation Devices and Methods of Therapy, to SIMON et al, the disclosure of which is incorporated herein by reference for all purposes as if copied and pasted herein; and other co-pending commonly assigned applications that are cited therein, the disclosure of which is incorporated herein by reference for all purposes as if copied and pasted herein]. At least some of the present disclosure elaborates on the electrical stimulation device, rather than the magnetic stimulation device that has similar functionality, with the understanding that unless it is otherwise indicated, the elaboration could apply to either the electrical or the magnetic nerve stimulation device. Because some properties of some of the earlier devices have already been disclosed, the present disclosure focuses on what is new with respect to the earlier disclosures.

The patient can apply the stimulator without the benefit of having a trained healthcare provider nearby. An advantage of the self-stimulation therapy is that it can be administered more or less immediately when symptoms occur, rather than having to visit the healthcare provider at a clinic or emergency room. A need for such a visit would only compound the aggravation that the patient is already experiencing. Another advantage of the self-stimulation therapy is the convenience of providing the therapy in the patient's home or workplace, which eliminates scheduling difficulties, for example, when the nerve stimulation is being administered for prophylactic reasons at odd hours of the day. Furthermore, the cost of the treatment may be reduced by not requiring the involvement of a trained healthcare provider.

The present disclosure discloses methods and devices for the non-invasive treatment of diseases and disorders, utilizing an energy source that transmits energy non-invasively to nervous tissue. In particular, the devices can transmit energy to, or in close proximity to, a nerve of the patient, such as the vagus nerve, in order to temporarily stimulate, block and/or modulate electrophysiological signals in that nerve. In some embodiments, some electrodes applied to the skin of the patient generate currents within the tissue of the patient. This may enable production and application of the electrical impulses so as to interact with the signals of one or more nerves, in order to achieve the therapeutic result.

As a preliminary matter, we first describe the vagus nerve itself and its most proximal connections, which are relevant to the disclosure below of the electrical waveforms that may be used to perform some of the stimulation. A fact that electrical stimulation of a vagus nerve can be used to treat many disorders may be understood as follows. The vagus nerve is composed of motor and sensory fibers. The vagus nerve leaves the cranium, passes down the neck within the carotid sheath to the root of the neck, then passes to the chest and abdomen, where it contributes to the innervation of the viscera. A human vagus nerve (tenth cranial nerve, paired left and right) comprises of over 100,000 nerve fibers (axons), mostly organized into groups. The groups are contained within fascicles of varying sizes, which branch and converge along the nerve. Under normal physiological conditions, each fiber conducts electrical impulses only in one direction, which is defined to be the orthodromic direction, and which is opposite the antidromic direction. However, external electrical stimulation of the nerve may produce action potentials that propagate in orthodromic and antidromic directions. Besides efferent output fibers that convey signals to the various organs in the body from the central nervous system, the vagus nerve conveys sensory (afferent) information about the state of the body's organs back to the central nervous system. Some 80-90% of the nerve fibers in the vagus nerve are afferent (sensory) nerves, communicating the state of the viscera to the central nervous system.

The largest nerve fibers within a left or right vagus nerve are approximately 20 μm in diameter and are heavily myelinated, whereas only the smallest nerve fibers of less than about 1 μm in diameter are completely unmyelinated. When the distal part of a nerve is electrically stimulated, a compound action potential may be recorded by an electrode located more proximally. A compound action potential contains several peaks or waves of activity that represent the summated response of multiple fibers having similar conduction velocities. The waves in a compound action potential represent different types of nerve fibers that are classified into corresponding functional categories, with approximate diameters as follows: A-alpha fibers (afferent or efferent fibers, 12-20 μm diameter), A-beta fibers (afferent or efferent fibers, 5-12 μm), A-gamma fibers (efferent fibers, 3-7 μm), A-delta fibers (afferent fibers, 2-5 μm), B fibers (1-3 μm) and C fibers (unmyelinated, 0.4-1.2 μm). The diameters of group A and group B fibers include the thickness of the myelin sheaths.

The vagus (or vagal) afferent nerve fibers arise from cell bodies located in the vagal sensory ganglia, which take the form of swellings near the base of the skull. Vagal afferents traverse the brainstem in the solitary tract, with some eighty percent of the terminating synapses being located in the nucleus of the tractus solitarius (or nucleus tractus solitarii, nucleus tractus solitarius, or NTS). The NTS projects to a wide variety of structures in the central nervous system, such as the amygdala, raphe nuclei, periaqueductal gray, nucleus paragigantocellurlais, olfactory tubercule, locus ceruleus, nucleus ambiguus and the hypothalamus. The NTS also projects to the parabrachial nucleus, which in turn projects to the hypothalamus, the thalamus, the amygdala, the anterior insula, and infralimbic cortex, lateral prefrontal cortex, and other cortical regions [JEAN A. The nucleus tractus solitarius: neuroanatomic, neurochemical and functional aspects. Arch Int Physiol Biochim Biophys 99 (5,1991):A3-A52 the disclosure of which is incorporated herein by reference for all purposes as if copied and pasted herein]. Thus, stimulation of vagal afferents can modulate the activity of many structures of the brain and brainstem through these projections.

With regard to vagal efferent nerve fibers, two vagal components have evolved in the brainstem to regulate peripheral parasympathetic functions. The dorsal vagal complex, consisting of the dorsal motor nucleus and its connections controls parasympathetic function primarily below the level of the diaphragm, while the ventral vagal complex, comprised of nucleus ambiguus and nucleus retrofacial, controls functions primarily above the diaphragm in organs such as the heart, thymus and lungs, as well as other glands and tissues of the neck and upper chest, and specialized muscles such as those of the esophageal complex. For example, the cell bodies for the preganglionic parasympathetic vagal neurons that innervate the heart reside in the nucleus ambiguus, which is relevant to potential cardiovascular side effects that may be produced by vagus nerve stimulation.

The vagus efferent fibers innervate parasympathetic ganglionic neurons that are located in or adjacent to each target organ. The vagal parasympathetic tone resulting from the activity of these fibers is balanced reflexively in part by sympathetic innervations. Consequently, electrical stimulation of a vagus nerve may result not only in modulation of parasympathetic activity in postganglionic nerve fibers, but also a reflex modulation of sympathetic activity. The ability of a vagus nerve to bring about widespread changes in autonomic activity, either directly through modulation of vagal efferent nerves, or indirectly via activation of brainstem and brain functions that are brought about by electrical stimulation of vagal afferent nerves, accounts for the fact that vagus nerve stimulation can treat many different medical conditions in many end organs. Selective treatment of particular conditions is possible because the parameters of the electrical stimulation (e.g. frequency, amplitude, pulse width, etc.) may selectively activate or modulate the activity of particular afferent or efferent A, B, and/or C fibers that result in a particular physiological response in each individual.

The electrodes used to stimulate a vagus nerve can be implanted about the nerve during open neck surgery. For many patients, this may be done with an objective of implanting permanent electrodes to treat epilepsy, depression, or other conditions [Arun Paul AMAR, Michael L. Levy, Charles Y. Liu and Michael L. J. Apuzzo. Chapter 50. Vagus nerve stimulation. pp. 625-638, the disclosure of which is incorporated herein by reference for all purposes as if copied and pasted herein. In: Elliot S. Krames, P. Hunber Peckham, Ali R. Rezai, eds. Neuromodulation. London: Academic Press, 2009, the disclosure of which is incorporated herein by reference for all purposes as if copied and pasted herein; KIRSE D J, Werle A H, Murphy J V, Eyen T P, Bruegger D E, Hornig G W, Torkelson R D. Vagus nerve stimulator implantation in children. Arch Otolaryngol Head Neck Surg 128 (11,2002):1263-1268, the disclosure of which is incorporated herein by reference for all purposes as if copied and pasted herein]. In that case, the electrode can be a spiral electrode, although other designs may be used as well [patent U.S. Pat. No. 4,979,511, entitled Strain relief tether for implantable electrode, to TERRY, Jr., the disclosure of which is incorporated herein by reference for all purposes as if copied and pasted herein; U.S. Pat. No. 5,095,905, entitled Implantable neural electrode, to KLEPINSKI, the disclosure of which is incorporated herein by reference for all purposes as if copied and pasted herein]. In other patients, a vagus nerve can be electrically stimulated during an open-neck thyroid surgery in order to confirm that the nerve has not been accidentally damaged during the surgery. In that case, a vagus nerve in the neck is surgically exposed, and a temporary stimulation electrode is clipped about the nerve [SCHNEIDER R, Randolph G W, Sekulla C, Phelan E, Thanh P N, Bucher M, Machens A, Dralle H, Lorenz K. Continuous intraoperative vagus nerve stimulation for identification of imminent recurrent laryngeal nerve injury. Head Neck. Nov. 20, 2012. doi: 10.1002/hed.23187 (Epub ahead of print, pp. 1-8), the disclosure of which is incorporated herein by reference for all purposes as if copied and pasted herein].

It is also possible to electrically stimulate a vagus nerve using a minimally invasive surgical approach, namely percutaneous nerve stimulation. In that procedure, a pair of electrodes (an active and a return electrode) are introduced through the skin of a patient's neck to the vicinity of a vagus nerve, and wires connected to the electrodes extend out of the patient's skin to a pulse generator [Publication number US20100241188, entitled Percutaneous electrical treatment of tissue, to J. P. ERRICO et al., the disclosure of which is incorporated herein by reference for all purposes as if copied and pasted herein; SEPULVEDA P, Bohill G, Hoffmann T J. Treatment of asthmatic bronchoconstriction by percutaneous low voltage vagal nerve stimulation: case report. Internet J Asthma Allergy Immunol 7(2009):e1 (pp 1-6), the disclosure of which is incorporated herein by reference for all purposes as if copied and pasted herein; MINER, J. R., Lewis, L. M., Mosnaim, G. S., Varon, J., Theodoro, D.

Hoffman, T. J. Feasibility of percutaneous vagus nerve stimulation for the treatment of acute asthma exacerbations. Acad Emerg Med 2012; 19: 421-429, the disclosure of which is incorporated herein by reference for all purposes as if copied and pasted herein].

Percutaneous nerve stimulation procedures has been somewhat described primarily for the treatment of pain, but not for a vagus nerve, which is ordinarily not considered to produce pain and which presents special challenges [HUNTOON M A, Hoelzer B C, Burgher A H, Hurdle M F, Huntoon E A. Feasibility of ultrasound-guided percutaneous placement of peripheral nerve stimulation electrodes and anchoring during simulated movement: part two, upper extremity. Reg Anesth Pain Med 33 (6,2008):558-565, the disclosure of which is incorporated herein by reference for all purposes as if copied and pasted herein; CHAN I, Brown A R, Park K, Winfree C J. Ultrasound-guided, percutaneous peripheral nerve stimulation: technical note. Neurosurgery 67 (3 Suppl Operative, 2010):ons136-139, the disclosure of which is incorporated herein by reference for all purposes as if copied and pasted herein; MONTI E. Peripheral nerve stimulation: a percutaneous minimally invasive approach. Neuromodulation 7 (3,2004):193-196, the disclosure of which is incorporated herein by reference for all purposes as if copied and pasted herein; Konstantin V SLAVIN. Peripheral nerve stimulation for neuropathic pain. U.S. Neurology 7 (2,2011):144-148, the disclosure of which is incorporated herein by reference for all purposes as if copied and pasted herein].

In some embodiments, a stimulation device is introduced through a percutaneous penetration in the patient to a target location within, adjacent to, or in close proximity with, the carotid sheath that contains the vagus nerve. Once in position, electrical impulses are applied through the electrodes of the stimulation device to one or more selected nerves (e.g., vagus nerve or one of its branches) to stimulate, block or otherwise modulate the nerve(s) and treat the patient's condition or a symptom of that condition. For some conditions, the treatment may be acute, meaning that the electrical impulse immediately begins to interact with one or more nerves to produce a response in the patient. In some cases, the electrical impulse will produce a response in the nerve(s) to improve the patient's condition or symptom in less than 3 hours, preferably less than 1 hour and more preferably less than 15 minutes. For other conditions, intermittently scheduled or as-needed stimulation of the nerve may produce improvements in the patient over the course of several hours, days, weeks, months or years. A more complete description of a suitable percutaneous procedure for vagal nerve stimulation can be found in commonly assigned, co-pending U.S. patent application titled "Percutaneous Electrical Treatment of Tissue", filed Apr. 13, 2009 (Ser. No. 12/422,483), the disclosure of which is incorporated herein by reference for all purposes as if copied and pasted herein.

In some embodiments, a time-varying magnetic field, originating and confined to the outside of a patient, generates an electromagnetic field and/or induces eddy currents within tissue of the patient. In some embodiments, electrodes applied to the skin of the patient generate currents within the tissue of the patient. In some embodiments, an objective may include an ability to produce and apply the electrical impulses so as to interact with the signals of one or more nerves, to treat patient's suffering post-operative symptoms following major surgery and/or for treating patients in critical or intensive care, such as those patient's suffering from stroke, transient ischemic attack (TIA), heart, kidney or respiratory failure, shock, sepsis, severe burns, severe illnesses (e.g., COVID-19) and the like.

Some of the disclosure is directed specifically to treatment of a patient by electromagnetic stimulation in or around a vagus nerve, with devices positioned non-invasively on or near a patient's neck. However, it will also be appreciated that some the devices and methods can be applied to other tissues and nerves of the body, including but not limited to other parasympathetic nerves, sympathetic nerves, spinal or cranial nerves. As recognized by those having skill in the art, the methods should be carefully evaluated prior to use in patients known to have preexisting cardiac issues. In addition, it will be recognized that some of the treatment paradigms can be used with a variety of different vagal nerve stimulators, including implantable and/or percutaneous stimulation devices, such as the ones described herein.

In some embodiments, broadly speaking, the Applicant has determined that there are several components to the effects of nVNS on the brain. For example, the strongest effect occurs during the acute stimulation and results in significant changes in brain function that can be clearly seen as acute changes in autonomic function (e.g. measured using pupillometry, heart rate variability, galvanic skin response, or evoked potential) and activation and inhibition of various brain regions as shown in fMRI imaging studies. For example, the second effect of moderate intensity, lasts for 15 to 180 minutes after stimulation. Animal studies have shown changes in neurotransmitter levels in various parts of the brain that persist for several hours. For example, the third effect of mild intensity, lasts up to 8 hours and is responsible for the long lasting alleviation of symptoms seen clinically and, for example, in animal models of migraine headache and autoimmune diseases, such as Sjôgren's syndrome and Rheumatoid arthritis or RA.

Treatment Paradigms

Thus, depending on the medical indication, whether it is a chronic or acute treatment, and the natural history of the disease, different treatment protocols may be used. In particular, applicant has discovered that it is not necessary to "continuously stimulate" the vagus nerve (or to in order to provide clinically efficacious benefits to patients with certain disorders. The term "continuously stimulate" as defined herein means stimulation that follows a certain On/Off pattern continuously 24 hours/day. For example, existing implantable vagal nerve stimulators "continuously stimulate" the vagus nerve with a pattern of 30 seconds ON/5 minutes OFF (or the like) for 24 hours/day and seven days/week. Applicant has determined that this continuous stimulation is not necessary to provide the desired clinical benefit for many disorders.

The present invention contemplates three types of interventions involving stimulation of a vagus nerve: prophylactic, acute and compensatory (rehabilitative). Among these, the acute treatment involves the fewest administrations of vagus nerve stimulations, which begin upon the appearance of symptoms. It is intended primarily to enlist and engage the autonomic nervous system to inhibit excitatory neurotransmissions that accompany the symptoms. The prophylactic treatment resembles the acute treatment in the sense that it is administered as though acute symptoms had just occurred (even though they have not) and is repeated at regular intervals, as though the symptoms were reoccurring (even though they are not). The rehabilitative or compensatory treatments, on the other hand, seek to promote long-term adjustments in the central nervous system, compensating for deficiencies that arose as the result of the patient's disease by making new neural circuits.

A vagus nerve stimulation treatment according to the present invention is conducted for continuous period of thirty seconds to five minutes, preferably about 90 seconds to about three minutes and more preferably about two minutes (each defined as a single dose). After a dose has been completed, the therapy is stopped for a period of time (depending on the treatment as described below). For prophylactic treatments, such as a treatment to reduce cortisol or other stress hormone levels, the therapy preferably comprises multiple doses/day over a period of time that may last from one day to a number of months or even years. In certain embodiments, the treatment will comprise multiple doses at predetermined times during the day and/or at predetermined intervals throughout the day. In exemplary embodiments, the treatment comprises one of the following: (1) 3 doses/day at predetermined intervals or times; (2) two doses, either consecutively, or separated by 5 min at predetermined intervals or times, preferably two or three times/day; (3) 3 doses, either consecutively or separated by 5 min again at predetermined intervals or times, such as 2 or 3 times/day; or (4) 1-3 doses, either consecutively or separated by 5 min, 4-6 times per day.

In exemplary embodiments, the treatment comprises one of the following: (1) 2-12 doses/day, preferably about 2-4 doses, at predetermined intervals or times; (2) two doses, either consecutively, or separated by 5 min at predetermined intervals or times, preferably two to four times/day; (3) 3 doses, either consecutively or separated by 5 min again at predetermined intervals or times, such as 2 or 3 times/day; or (4) 1-3 doses, either consecutively or separated by 5 min, 4-6 times per day.

For certain disorders, the time of day can be more important than the time interval between treatments. For example, the locus correleus has periods of time during a 24 hour day wherein it has inactive periods and active periods. Typically, the inactive periods can occur in the late afternoon or in the middle of the night when the patient is asleep. It is during the inactive periods that the levels of inhibitory neurotransmitters in the brain that are generated by the locus correleus are reduced. This may have an impact on certain disorders. For example, patients suffering from migraines or cluster headaches often receive these headaches after an inactive period of the locus correleus. For these types of disorders, the prophylactic treatment is optimal during the inactive periods such that the amounts of inhibitory neurotransmitters in the brain can remain at a higher enough level to mitigate or abort an acute attack of the disorder.

In these embodiments, the prophylactic treatment may comprise multiple doses/day timed for periods of inactivity of the locus correleus. In one embodiment, a treatment according to the present invention comprises one or more doses administered 2-3 times per day or 2-3 "treatment sessions" per day. The treatment sessions preferably occur during the late afternoon or late evening, in the middle of the night and again in the morning when the patient wakes up. In an exemplary embodiment, each treatment session comprises 1-4 doses, preferably 2-3 doses, with each dose lasting for about 60 seconds to about 5 minutes, preferably about 90 seconds to about three minutes.

For other disorders, the intervals between treatment sessions may be the most important as applicant has determined that stimulation of the vagus nerve can have a prolonged effect on the inhibitor neurotransmitters levels in the brain, e.g., at least one hour, up to 3 hours and sometimes up to 8 hours. In one embodiment, a treatment according to the present invention comprises one or more doses (i.e., treatment sessions) administered at intervals during a 24 hour period. In a preferred embodiment, there are 1-5 such treatment sessions, preferably 2-4 treatment sessions. Each treatment session preferably comprises 1-3 doses, each "dose" lasting between about 60 seconds to about five minutes, preferably about 90 seconds to about 150 seconds, more preferably about 2 minutes.

For all of the treatments listed above, one may alternate treatment between left and right sides, or in the case of stroke or migraine that occur in particular brain hemispheres, one may treat ipsilateral or contralateral to the stroke-hemisphere or headache side, respectively. Or for a single treatment, one may treat one minute on one side followed by one minute on the opposite side. Variations of these treatment paradigms may be chosen on a patient-by-patient basis. However, it is understood that parameters of the stimulation protocol may be varied in response to heterogeneity in the symptoms of patients. Different stimulation parameters may also be selected as the course of the patient's condition changes. In preferred embodiments, the disclosed methods and devices do not produce clinically significant side effects, such as agitation or anxiety, or changes in heart rate or blood pressure.

The prophylactic treatments may be most effective when the patient is in a prodromal, high-risk bistable state. In that state, the patient is simultaneously able to remain normal or exhibit symptoms, and the selection between normal and symptomatic states depends on the amplification of fluctuations by physiological feedback networks. For example, a thrombus may exist in either a gel or fluid phase, with the feedback amplification of fluctuations driving the change of phase and/or the volume of the gel phase. Thus, a thrombus may form or not, depending on the nonlinear dynamics exhibited by the network of enzymes involved in clot formation, as influenced by blood flow and inflammation that may be modulated by vagus nerve stimulation [PANTELEEV M A, Balandina A N, Lipets E N, Ovanesov M V, Ataullakhanov F I. Task-oriented modular decomposition of biological networks: trigger mechanism in blood coagulation. Biophys J 98 (9,2010):1751-1761; Alexey M SHIBEKO, Ekaterina S Lobanova, Mikhail A Panteleev and Fazoil I Ataullakhanov. Blood flow controls coagulation onset via the positive feedback of factor VII activation by factor Xa. BMC Syst Biol 2010; 4(2010):5, pp. 1-12]. Consequently, the mechanisms of vagus nerve stimulation treatment during prophylaxis are generally different than what occurs during an acute treatment, when the stimulation inhibits excitatory neurotransmission that follows the onset of ischemia that is already caused by the thrombus. Nevertheless, the prophylactic treatment may also inhibit excitatory neurotransmission so as to limit the excitation that would eventually occur upon formation of a thrombus, and the acute treatment may prevent the formation of another thrombus.

Description of Various Nerve Stimulating/Modulating Devices

Some devices that are used to stimulate a vagus nerve are now described. An embodiment is shown in FIG. 1, which is a schematic diagram of an electrode-based nerve stimulating and/or modulating device 302 for delivering impulses of energy to nerves for the treatment of medical conditions. As shown, device 302 may include an impulse generator 310; an energy or power source 320 coupled to the impulse generator 310; a control unit 330 in communication with the impulse generator 310 and coupled to the energy source 320; and electrodes 340 coupled via wires 345 to impulse generator 310. In some embodiments, the same impulse generator 310, energy source 320, and control unit 330 may be used for either a magnetic stimulator or the electrode-based stimulator 302, allowing the user to change parameter settings depending on whether magnetic coils or the electrodes 340 are attached.

Although a pair of electrodes 340 is shown in FIG. 1C, in practice the electrodes may also comprise three or more distinct electrode elements, each of which is connected in series or in parallel to the impulse generator 310. Thus, the electrodes 340 that are shown in FIG. 1C represent some, most, many, or all electrodes of the device collectively.

In certain embodiments, device 302 may also include is a volume, contiguous with an electrode 340, that is filled with electrically conducting medium 350. The conducting medium in which the electrode 340 is embedded need not completely surround or extend about an electrode. The volume 350 is electrically connected to the patient at a target skin surface in order to shape the current density passed through an electrode 340 that is needed to accomplish stimulation of the patient's nerve or tissue. The electrical connection to the patient's skin surface is through an interface 351. In some embodiments, the interface is made of an electrically insulating (dielectric) material, such as a thin sheet of Mylar. In that case, electrical coupling of the stimulator to the patient is capacitive. In some embodiments, the interface comprises electrically conducting material, such as the electrically conducting medium 350 itself, an electrically conducting or permeable membrane, or a metal piece. In that case, electrical coupling of the stimulator to the patient is ohmic. As shown, the interface may be deformable such that it is form fitting when applied to the surface of the body. Thus, the sinuousness or curvature shown at the outer surface of the interface 351 corresponds also to sinuousness or curvature on the surface of the body, against which the interface 351 is applied, so as to make the interface and body surface contiguous.

The control unit 330 controls the impulse generator 310 to generate a signal for each of the device's electrodes (or magnetic coils). The signals are selected to be suitable for amelioration of a particular medical condition when the signals are applied non-invasively to a target nerve or tissue via the electrodes 340. It is noted that nerve stimulating/modulating device 302 may be referred to by its function as a pulse generator. Patent application publications US2005/0075701 and US2005/0075702, both to SHAFER, the disclosure of which is incorporated herein by reference for all purposes as if copied and pasted herein, contain descriptions of pulse generators that may be applicable to this disclosure. By way of example, a pulse generator is also commercially available, such as Agilent 33522A Function/Arbitrary Waveform Generator, Agilent Technologies, Inc., 5301 Stevens Creek Blvd Santa Clara CA 95051.

The control unit 330 may comprise a general purpose computer, comprising one or more CPU, computer memories for the storage of executable computer programs (including the system's operating system) and the storage and retrieval of data, disk storage devices, communication devices (such as serial and USB ports) for accepting external signals from a keyboard, computer mouse, and touchscreen, as well as any externally supplied physiological signals, analog-to-digital converters for digitizing externally supplied analog signals, communication devices for the transmission and receipt of data to and from external devices such as printers and modems that comprise part of the system, hardware for generating the display of information on monitors or display screens that comprise part of the system, and busses to interconnect the above-mentioned components. Thus, the user may operate the system by typing or otherwise providing instructions for the control unit 330 at a device such as a keyboard or touch-screen and view the results on a device such as the system's computer monitor or display screen, or direct the results to a printer, modem, and/or storage disk. Control of the system may be based upon feedback measured from externally supplied physiological or environmental signals. Alternatively, the control unit 330 may have a compact and simple structure, for example, wherein the user may operate the system using only an on/off switch and energy control wheel or knob, or their touchscreen equivalent. In a section below, an embodiment is also described wherein the stimulator housing has a simple structure, but other components of the control unit 330 are distributed into other devices (see FIG. 5).

Parameters for the nerve or tissue stimulation include energy level, frequency and train duration (or pulse number). The stimulation characteristics of each pulse, such as depth of penetration, strength and selectivity, depend on the rise time and peak electrical energy transferred to the electrodes, as well as the spatial distribution of the electric field that is produced by the electrodes. The rise time and peak energy are governed by the electrical characteristics of the stimulator and electrodes, as well as by the anatomy of the region of current flow within the patient. In some embodiments, pulse parameters are set in such a way as to account for the detailed anatomy surrounding the nerve that is being stimulated [Bartosz SAWICKI, Robert Szmurlo, Przemyslaw Plonecki, Jacek Starzyński, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008, the disclosure of which is incorporated herein by reference for all purposes as if copied and pasted herein]. Pulses may be monophasic, biphasic or polyphasic. In some embodiments, some devices include those that are fixed frequency, where each pulse in a train has the same inter-stimulus interval, and those that have modulated frequency, where the intervals between each pulse in a train can be varied.

Figure 2A:
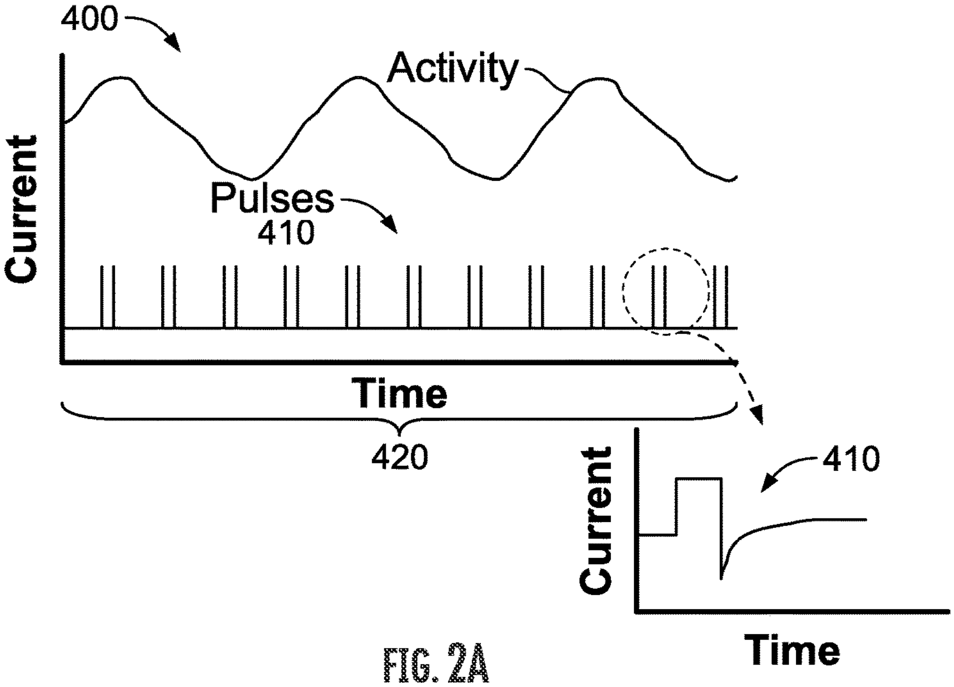
FIG. 2A shows an embodiment of an electrical voltage/current profile for stimulating and/or modulating impulses that are applied to a nerve according to this disclosure.

FIG. 2A illustrates an example of an electrical voltage/current profile for a stimulating, blocking and/or modulating impulse applied to a portion or portions of selected nerves in accordance with an embodiment of this disclosure. For some embodiments, the voltage and current refer to those that are non-invasively produced within the patient by the electrodes (or magnetic coils). As shown, a suitable electrical voltage/current profile 400 for the blocking and/or modulating impulse 410 to the portion or portions of a nerve may be achieved using pulse generator 310. In some embodiments, the pulse generator 310 may be implemented using an energy source 320 and a control unit 330 having, for instance, a processor, a clock, a memory, etc., to produce a pulse train 420 to the electrodes 340 that deliver the stimulating, blocking and/or modulating impulse 410 to the nerve. Nerve stimulating/modulating device 302 may be externally energized and/or recharged or may have its own energy source 320. The parameters of the modulation signal 400, such as the frequency, amplitude, duty cycle, pulse width, pulse shape, etc., can be programmable, non-programmable, modifiable, locally or remotely updateable, or others. An external communication device may modify the pulse generator programming to improve treatment.

In addition, or as an alternative to some of the devices to implement the modulation unit for producing the electrical voltage/current profile of the stimulating, blocking and/or modulating impulse to the electrodes, the device disclosed in U.S. Patent Application Publication No. US2005/0216062, the disclosure of which is incorporated herein by reference for all purposes as if copied and pasted herein, may be employed. That patent publication discloses a multifunctional electrical stimulation (ES) system adapted to yield output signals for effecting electromagnetic or other forms of electrical stimulation for a broad spectrum of different biological and biomedical applications, which produce an electric field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004), the disclosure of which is incorporated herein by reference for all purposes as if copied and pasted herein]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated, as well as the outputs of various sensors which sense prevailing conditions prevailing in this substance, whereby the user of the system can manually adjust the signal, or have it automatically adjusted by feedback, to provide an electrical stimulation signal of whatever type the user wishes, who can then observe the effect of this signal on a substance being treated.

The stimulating and/or modulating impulse signal 410 preferably has a frequency, an amplitude, a duty cycle, a pulse width, a pulse shape, etc. selected to influence the therapeutic result, namely, stimulating and/or modulating some or all of the transmission of the selected nerve. For example, the frequency may be about 1 Hz or greater, such as between about 15 Hz to 100 Hz, preferably between about 15-50 Hz and more preferably between about 15-35 Hz. In some embodiments, the frequency is 25 Hz. The modulation signal may have a pulse width selected to influence the therapeutic result, such as about 1 microseconds to about 1000 microseconds, preferably about 100-400 microseconds and more preferably about 200-400 microseconds. For example, the electric field induced or produced by the device within tissue in the vicinity of a nerve may be about 5 to 600 V/m, preferably less than 100 V/m, and even more preferably less than 30 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz. The modulation signal may have a peak voltage amplitude selected to influence the therapeutic result, such as about 0.2 volts or greater, such as about 0.2 volts to about 40 volts, preferably between about 1-20 volts and more preferably between about 2-12 volts.

Figure 2B:
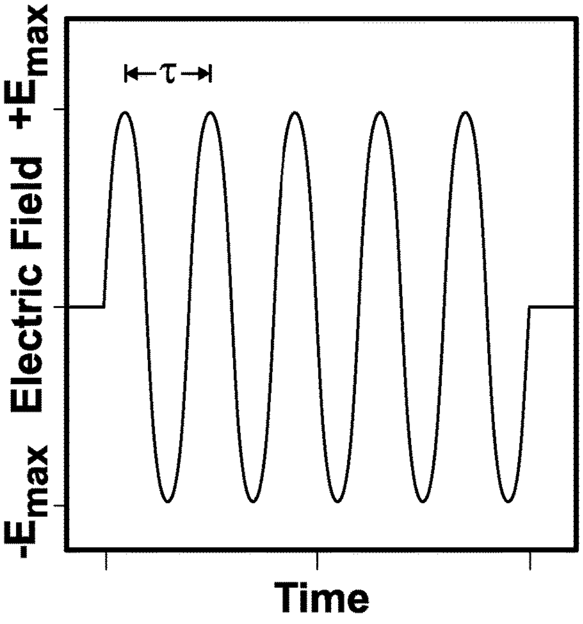
FIG. 2B illustrates an embodiment of a bursting electrical waveform for stimulating and/or modulating a nerve according to this disclosure.
Figure 2C:
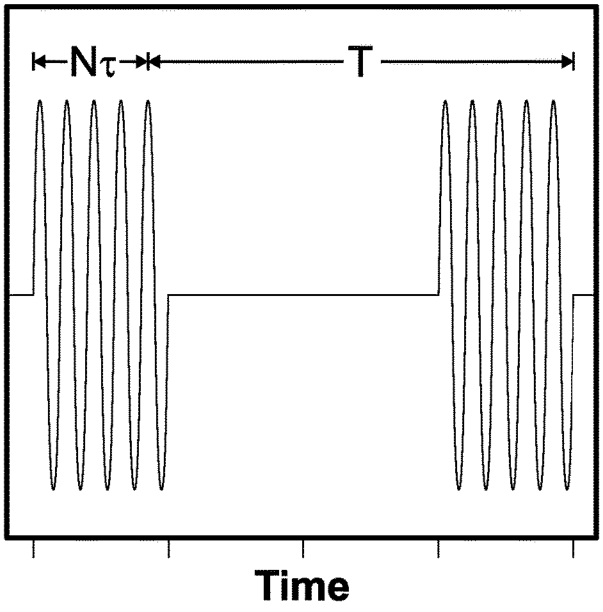
FIG. 2C illustrates an embodiment of two successive bursts of the waveform of FIG. 2B according to this disclosure.

In an exemplary embodiment, the waveform comprises bursts of sinusoidal pulses, as shown in FIGS. 2B and 2C. As seen there, individual sinusoidal pulses have a period of T, and a burst consists of N such pulses. This is followed by a period with no signal (the inter-burst period). The pattern of a burst followed by silent inter-burst period repeats itself with a period of T. For example, the sinusoidal period T may be between about 50-1000 microseconds with a frequency of about 1-20 kHz), preferably between about 100-400 microseconds with a frequency of about 2.5-10 kHz, more preferably about 133-400 microseconds with a frequency of about 2.5-7.5 kHz and even more preferably about 200 microseconds with a frequency of about 5 kHz; the number of pulses per burst may be N=1-20, preferably about 2-10 and more preferably about 5; and the whole pattern of burst followed by silent inter-burst period may have a period T comparable to about 5-100 Hz, preferably about 15-50 Hz, more preferably about 25-35 Hz and even more preferably about 25 Hz (a much smaller value of T is shown in FIG. 2E to make the bursts discernable). When these exemplary values are used for T and T, the waveform contains significant Fourier components at higher frequencies (1/200 microseconds=5000/sec), as compared with those contained in transcutaneous nerve stimulation waveforms, as currently practiced.

The above waveform is essentially a 1-20 kHz signal that includes bursts of pulses with each burst having a frequency of about 5-100 Hz and each pulse having a frequency of about 1-20 kHz. Another way of thinking about the waveform is that it is a 1-20 kHz waveform that repeats itself at a frequency of about 5-100 Hz.

In some embodiments, an objective of some of the disclosed stimulators is to provide both nerve fiber selectivity and spatial selectivity. Spatial selectivity may be achieved in part through the design of the electrode (or magnetic coil) configuration, and nerve fiber selectivity may be achieved in part through the design of the stimulus waveform, but designs for the two types of selectivity are intertwined. This is because, for example, a waveform may selectively stimulate only one of two nerves whether they lie close to one another or not, obviating the need to focus the stimulating signal onto only one of the nerves [GRILL W and Mortimer J T. Stimulus waveforms for selective neural stimulation. IEEE Eng. Med. Biol. 14 (1995): 375-385, the disclosure of which is incorporated herein by reference for all purposes as if copied and pasted herein]. These methods complement others that are used to achieve selective nerve stimulation, such as the use of local anesthetic, application of pressure, inducement of ischemia, cooling, use of ultrasound, graded increases in stimulus intensity, exploiting the absolute refractory period of axons, and the application of stimulus blocks [John E. SWETT and Charles M. Bourassa. Electrical stimulation of peripheral nerve. In: Electrical Stimulation Research Techniques, Michael M. Patterson and Raymond P. Kesner, eds. Academic Press. (New York, 1981) pp. 243-295, the disclosure of which is incorporated herein by reference for all purposes as if copied and pasted herein].

For some devices, to date, some of the selection of stimulation waveform parameters for nerve stimulation has been highly empirical, in which the parameters are varied about some initially successful set of parameters, in an effort to find an improved set of parameters for each patient. A more efficient approach to selecting stimulation parameters might be to select a stimulation waveform that mimics electrical activity in the anatomical regions that one is attempting stimulate indirectly, in an effort to entrain the naturally occurring electrical waveform, as suggested in patent number U.S. Pat. No. 6,234,953, entitled Electrotherapy device using low frequency magnetic pulses, to THOMAS et al; the disclosure of which is incorporated herein by reference for all purposes as if copied and pasted herein, and application number US20090299435, entitled Systems and methods for enhancing or affecting neural stimulation efficiency and/or efficacy, to GLINER et al, the disclosure of which is incorporated herein by reference for all purposes as if copied and pasted herein. One may also vary stimulation parameters iteratively, in search of an optimal setting [patent U.S. Pat. No. 7,869,885, entitled Threshold optimization for tissue stimulation therapy, to BEGNAUD et al, the disclosure of which is incorporated herein by reference for all purposes as if copied and pasted herein]. However, some stimulation waveforms, such as those described herein, are discovered by trial and error, and then deliberately improved upon.

Invasive nerve stimulation typically uses square wave pulse signals. However, Applicant found that square waveforms are not ideal for non-invasive stimulation, as they produce excessive pain, but still can be used. Prepulses and similar waveform modifications have been suggested as methods to improve selectivity of nerve stimulation waveforms, but Applicant also did not find them ideal, although they still can be used [Aleksandra VUCKOVIC, Marco Tosato and Johannes J Struijk. A comparative study of three techniques for diameter selective fiber activation in the vagal nerve: anodal block, depolarizing prepulses and slowly rising pulses. J. Neural Eng. 5 (2008): 275-286, the disclosure of which is incorporated herein by reference for all purposes as if copied and pasted herein; Aleksandra VUCKOVIC, Nico J. M. Rijkhoff, and Johannes J. Struijk. Different Pulse Shapes to Obtain Small Fiber Selective Activation by Anodal Blocking—A Simulation Study. IEEE Transactions on Biomedical Engineering 51 (5,2004):698-706, the disclosure of which is incorporated herein by reference for all purposes as if copied and pasted herein; Kristian HENNINGS. Selective Electrical Stimulation of Peripheral Nerve Fibers: Accommodation Based Methods. Ph.D. Thesis, Center for Sensory-Motor Interaction, Aalborg University, Aalborg, Denmark, 2004, the disclosure of which is incorporated herein by reference for all purposes as if copied and pasted herein].

In some embodiments, the use of feedback to generate the modulation signal 400 may result in a signal that is not periodic, particularly if the feedback is produced from sensors that measure naturally occurring, time-varying aperiodic physiological signals from the patient. In fact, the absence of significant fluctuation in naturally occurring physiological signals from a patient is ordinarily considered to be an indication that the patient is in ill health. This is because a pathological control system that regulates the patient's physiological variables may have become trapped around only one of two or more possible steady states and is therefore unable to respond normally to external and internal stresses. Accordingly, even if feedback is not used to generate the modulation signal 400, it may be useful to artificially modulate the signal in an aperiodic fashion, in such a way as to simulate fluctuations that would occur naturally in a healthy individual. Thus, the noisy modulation of the stimulation signal may cause a pathological physiological control system to be reset or undergo a non-linear phase transition, through a mechanism known as stochastic resonance [B. SUKI, A. Alencar, M. K. Sujeer, K. R. Lutchen, J. J. Collins, J. S. Andrade, E. P. Ingenito, S. Zapperi, H. E. Stanley, Life-support system benefits from noise, Nature 393 (1998) 127-128, the disclosure of which is incorporated herein by reference for all purposes as if copied and pasted herein; W Alan C MUTCH, M Ruth Graham, Linda G Girling and John F Brewster. Fractal ventilation enhances respiratory sinus arrhythmia. Respiratory Research 2005, 6:41, pp. 1-9, the disclosure of which is incorporated herein by reference for all purposes as if copied and pasted herein].

In some embodiments, the modulation signal 400, with or without feedback, will stimulate the selected nerve fibers in such a way that one or more of the stimulation parameters (e.g., energy, frequency, and others mentioned herein) are varied by sampling a statistical distribution having a mean corresponding to a selected, or to a most recent running-averaged value of the parameter, and then setting the value of the parameter to the randomly sampled value. The sampled statistical distributions will comprise Gaussian and 1/f, obtained from recorded naturally occurring random time series or by calculated formula. Parameter values will be so changed periodically, or at time intervals that are themselves selected randomly by sampling another statistical distribution, having a selected mean and coefficient of variation, where the sampled distributions comprise Gaussian and exponential, obtained from recorded naturally occurring random time series or by calculated formula.

In some embodiments, some devices, as disclosed herein, are provided in a "pacemaker" type form, in which electrical impulses 410 are generated to a selected region of the nerve by a stimulator device on an intermittent basis, to create in the patient a lower reactivity of the nerve.

Embodiments of the Stimulators

The electrodes of the some of the devices, as disclosed herein, are applied to the surface of the neck, or to some other surface of the body, and are used to deliver electrical energy non-invasively to a nerve. Embodiments may differ with regard to the number of electrodes that are used, the distance between electrodes, and whether disk, ring or other shapes of electrodes are used. In some embodiments, one selects the electrode configuration for individual patients, in such a way as to optimally focus electric fields and currents onto the selected nerve, without generating excessive currents on the surface of the skin.

Figure 3A:
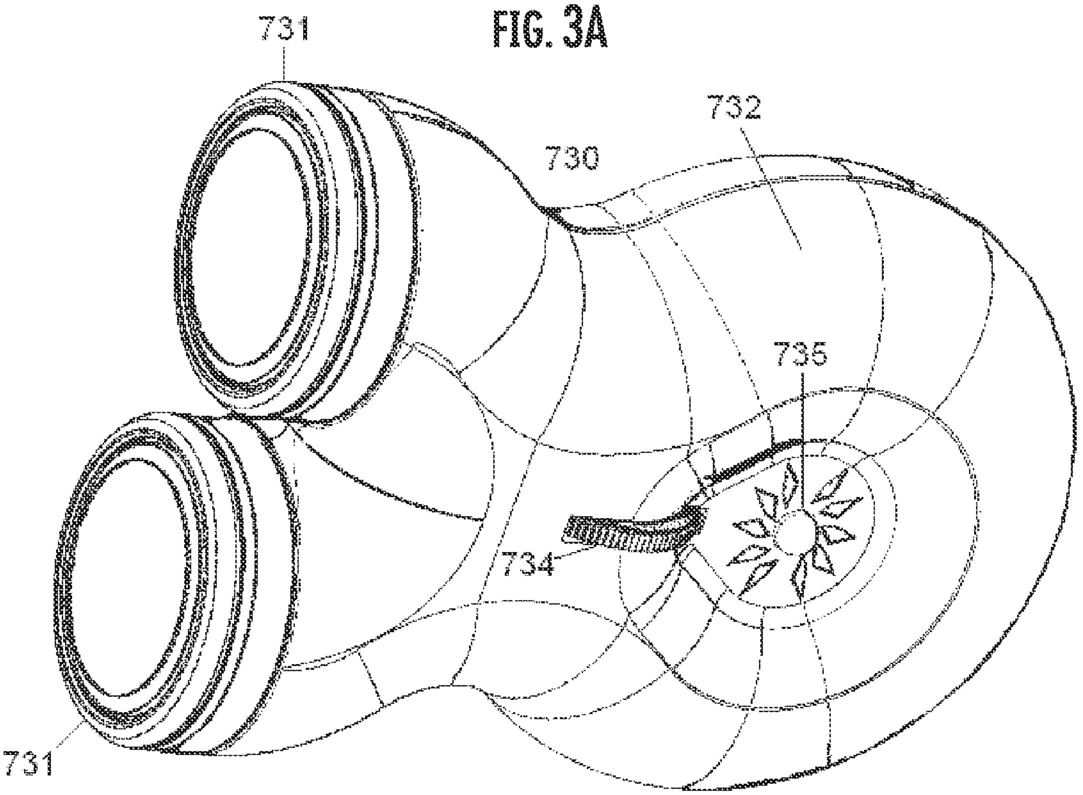
FIG. 3A is a perspective view of a stimulator according to another embodiment of the present invention.
Figure 3B:
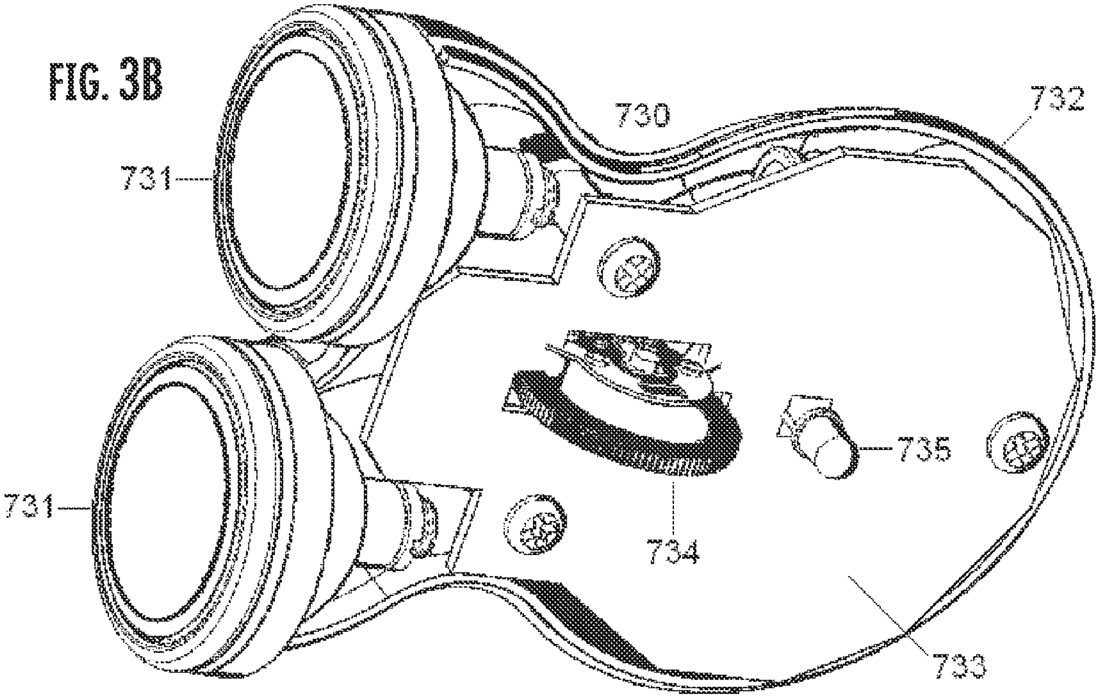
FIG. 3B is a cut-a-way view of the stimulator of FIG. 3A.

One embodiment of an electrode-based stimulator is shown in FIG. 3A. A cross-sectional view of the stimulator along its long axis is shown in FIG. 3B. As shown, the stimulator (730) comprises two heads (731) and a body (732) that joins them. Each head (731) contains a stimulating electrode. The body of the stimulator (732) contains the electronic components and battery (not shown) that are used to generate the signals that drive the electrodes, which are located behind the insulating board (733) that is shown in FIG. 3B. However, in other embodiments of the invention, the electronic components that generate the signals that are applied to the electrodes may be separate, but connected to the electrode head (731) using wires. Furthermore, other embodiments of the invention may contain a single such head or ore than two heads.

Heads of the stimulator (731) are applied to a surface of the patient's body, during which time the stimulator may be held in place by straps or frames or collars, or the stimulator may be held against the patient's body by hand. In either case, the level of stimulation energy may be adjusted with a wheel (734) that also serves as an on/off switch. A light (735) is illuminated when energy is being supplied to the stimulator. An optional cap may be provided to cover each of the stimulator heads (731), to protect the device when not in use, to avoid accidental stimulation, and to prevent material within the head from leaking or drying. Thus, in this embodiment of the invention, mechanical and electronic components of the stimulator (impulse generator, control unit, and energy source) are compact, portable, and simple to operate.

Figure 3C:
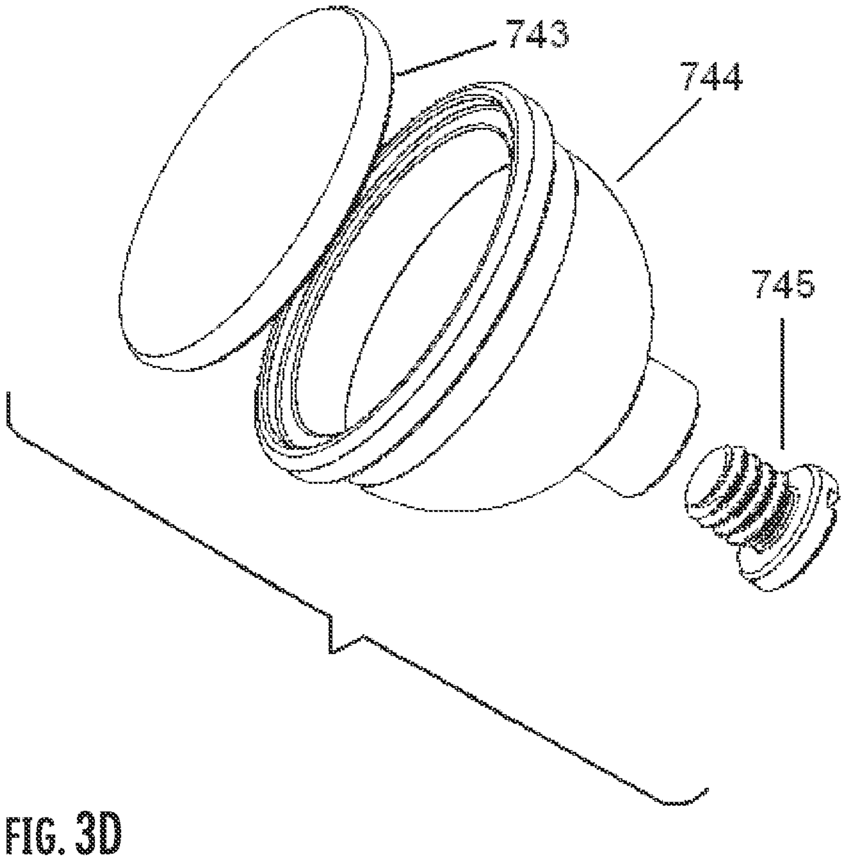
FIG. 3C is an exploded view of one of the electrode assemblies of the stimulator of FIG. 3A.
Figure 3D:
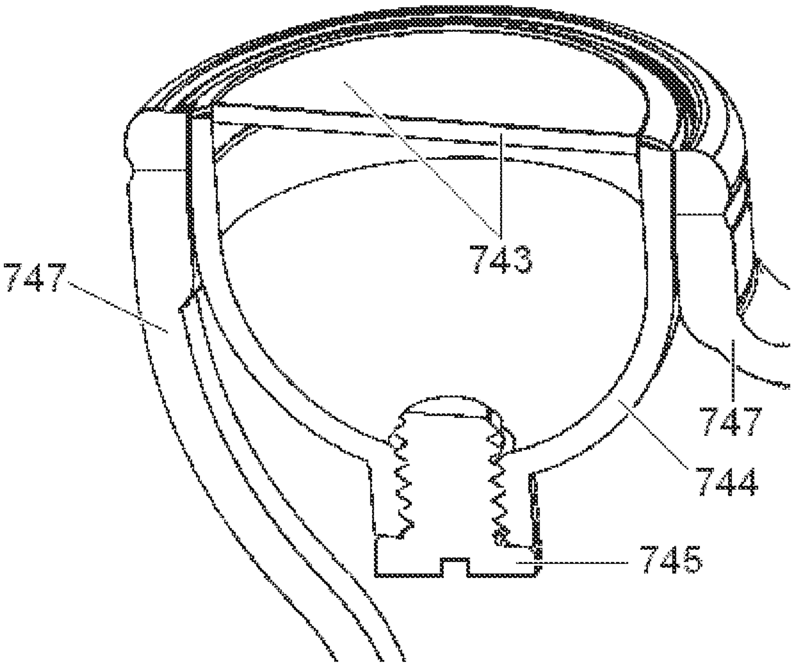
FIG. 3D is a cut-a-way view of the electrode assembly of FIG. 3C.

Details of one embodiment of the stimulator head are shown in FIGS. 3C and 3D. The electrode head may be assembled from a disc without fenestration (743), or alternatively from a snap-on cap that serves as a tambour for a dielectric or conducting membrane, or alternatively the head may have a solid fenestrated head-cup. The electrode may also be a screw (745). The preferred embodiment of the disc (743) is a solid, ordinarily uniformly conducting disc (e.g., metal such as stainless steel), which is possibly flexible in some embodiments. An alternate embodiment of the disc is a non-conducting (e.g., plastic) aperture screen that permits electrical current to pass through its apertures, e.g., through an array of apertures (fenestration). The electrode (745, also 340 in FIG. 3B) seen in each stimulator head may have the shape of a screw that is flattened on its tip. Pointing of the tip would make the electrode more of a point source, such that the equations for the electrical potential may have a solution corresponding more closely to a far-field approximation. Rounding of the electrode surface or making the surface with another shape will likewise affect the boundary conditions that determine the electric field. Completed assembly of the stimulator head is shown in FIG. 3D, which also shows how the head is attached to the body of the stimulator (747).

If a membrane is used, it ordinarily serves as the interface shown as 351 in FIG. 3B. For example, the membrane may be made of a dielectric (non-conducting) material, such as a thin sheet of Mylar (biaxially-oriented polyethylene terephthalate, also known as BoPET). In other embodiments, it may be made of conducting material, such as a sheet of Tecophlic material from Lubrizol Corporation, 29400 Lakeland Boulevard, Wickliffe, Ohio 44092. In one embodiment, apertures of the disc may be open, or they may be plugged with conducting material, for example, KM10T hydrogel from Katecho Inc., 4020 Gannett Ave., Des Moines IA 50321. If the apertures are so-plugged, and the membrane is made of conducting material, the membrane becomes optional, and the plug serves as the interface 351 shown in FIG. 2B.

The head-cup (744) may be filled with conducting material (350 in FIG. 1), for example, SIGNAGEL Electrode Gel from Parker Laboratories, Inc., 286 Eldridge Rd., Fairfield NJ 07004. The head-cup (744) and body of the stimulator are made of a non-conducting material, such as acrylonitrile butadiene styrene. The depth of the head-cup from its top surface to the electrode may be between one and six centimeters. The head-cup may have a different curvature than what is shown in FIG. 3D, or it may be tubular or conical or have some other inner surface geometry that will affect the Neumann boundary conditions that determine the electric field strength.

In certain embodiments, the disc interface 743 actually functions as the electrode and the screw 745 is simply the output connection to the signal generator electronics. In this embodiment, electrically conductive fluid or gel is positioned between the signal generator and the interface or electrode 745. In this embodiment, the conductive fluid filters out or eliminates high frequency components from the signal to smooth out the signal before it reaches the electrode (s) 745. When the signal is generated, energy switching and electrical noise typically add unwanted high frequency spikes back into the signal. In addition, the pulsing of the sinusoidal bursts may induce high frequency components in the signal. By filtering the signal just before it reaches the electrodes 745 with the conductive fluid, a smoother, cleaner signal is applied to the patient, thereby reducing the pain and discomfort felt by the patient and allowing a higher amplitude to be applied to the patient. This allows a sufficiently strong signal to be applied to reach a deeper nerve, such as the vagus nerve, without causing too much pain and discomfort to the patient at the surface of their skin.

In other embodiments, a low-pass filter may be used instead of the electrically conductive fluid to filter out the undesirable high frequency components of the signal. The low-pass filter may comprise a digital or analog filter or simply a capacitor placed in series between the signal generator and the electrode/interface.

If an outer membrane is used and is made of conducting materials, and the disc (743) in FIG. 3C is made of solid conducting materials such as stainless steel, then the membrane becomes optional, in which case the disc may serve as the interface 351 shown in FIG. 1. Thus, an embodiment without the membrane is shown in FIGS. 3C and 3D. This version of the device comprises a solid (but possibly flexible in some embodiments) conducting disc that cannot absorb fluid, the non-conducting stimulator head (744) into or onto which the disc is placed, and the electrode (745), which is also a screw. It is understood that the disc (743) may have an anisotropic material or electrical structure, for example, wherein a disc of stainless steel has a grain, such that the grain of the disc should be rotated about its location on the stimulator head, in order to achieve optimal electrical stimulation of the patient. As seen in FIG. 3D, these items are assembled to become a sealed stimulator head that is attached to the body of the stimulator (747). The disc (743) may screw into the stimulator head (744), it may be attached to the head with adhesive, or it may be attached by other methods that are known in the art. The chamber of the stimulator head-cup is filled with a conducting gel, fluid, or paste, and because the disc (743) and electrode (745) are tightly sealed against the stimulator head-cup (744), the conducting material within the stimulator head cannot leak out. In addition, this feature allows the user to easily clean the outer surface of the device (e.g., with isopropyl alcohol or similar disinfectant), avoiding potential contamination during subsequent uses of the device.

In some embodiments, the interface comprises a fluid permeable material that allows for passage of current through the permeable portions of the material. In these embodiments, a conductive medium (such as a gel) is preferably situated between the electrode(s) and the permeable interface. The conductive medium provides a conductive pathway for electrons to pass through the permeable interface to the outer surface of the interface and to the patient's skin.

In other embodiments of the present invention, the interface is made from a very thin material with a high dielectric constant, such as material used to make capacitors. For example, it may be Mylar having a submicron thickness (preferably in the range about 0.5 to about 1.5 microns) having a dielectric constant of about 3. Because one side of Mylar is slick, and the other side is microscopically rough, the present invention contemplates two different configurations: one in which the slick side is oriented towards the patient's skin, and the other in which the rough side is so-oriented. Thus, at stimulation Fourier frequencies of several kilohertz or greater, the dielectric interface will capacitively couple the signal through itself, because it will have an impedance comparable to that of the skin. Thus, the dielectric interface will isolate the stimulator's electrode from the tissue, yet allow current to pass. In one embodiment of the present invention, non-invasive electrical stimulation of a nerve is accomplished essentially substantially capacitively, which reduces the amount of ohmic stimulation, thereby reducing the sensation the patient feels on the tissue surface. This would correspond to a situation, for example, in which at least 30%, preferably at least 50%, of the energy stimulating the nerve comes from capacitive coupling through the stimulator interface, rather than from ohmic coupling. In other words, a substantial portion (e.g., 50%) of the voltage drop is across the dielectric interface, while the remaining portion is through the tissue.

In certain exemplary embodiments, the interface and/or its underlying mechanical support comprise materials that will also provide a substantial or complete seal of the interior of the device. This inhibits any leakage of conducting material, such as gel, from the interior of the device and also inhibits any fluids from entering the device. In addition, this feature allows the user to easily clean the surface of the dielectric material (e.g., with isopropyl alcohol or similar disinfectant), avoiding potential contamination during subsequent uses of the device. One such material is a thin sheet of Mylar, supported by a stainless steel disc, as described above.

The selection of the material for the dielectric constant involves at least two important variables: (1) the thickness of the interface; and (2) the dielectric constant of the material. The thinner the interface and/or the higher the dielectric constant of the material, the lower the voltage drop across the dielectric interface (and thus the lower the driving voltage required). For example, with Mylar, the thickness could be about 0.5 to about 5 microns (preferably about 1 micron) with a dielectric constant of about 3. For a piezoelectric material like barium titanate or PZT (lead zirconate titanate), the thickness could be about 100-400 microns (preferably about 200 microns or 0.2 mm) because the dielectric constant is >1000.

Figure 5A:
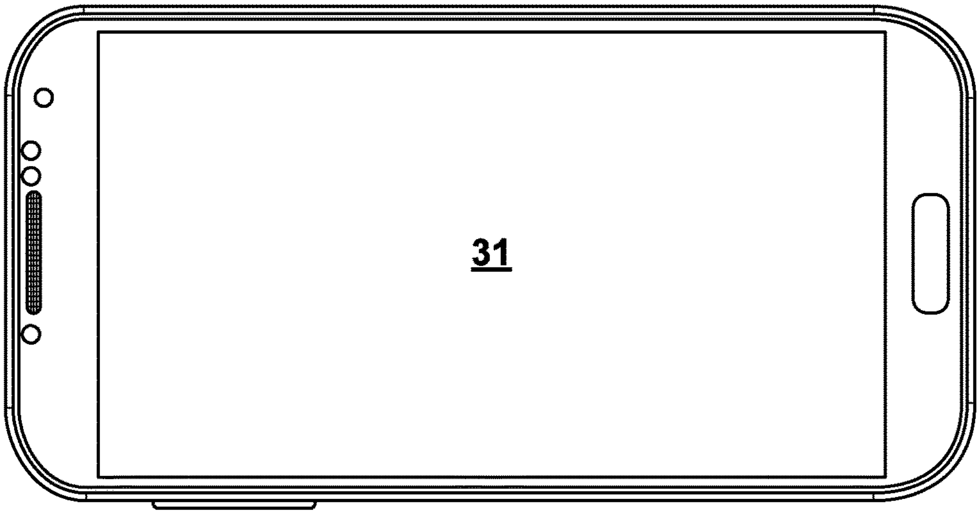
FIG. 5A is a front view of another embodiment of a stimulator according to this disclosure.
Figure 5B:
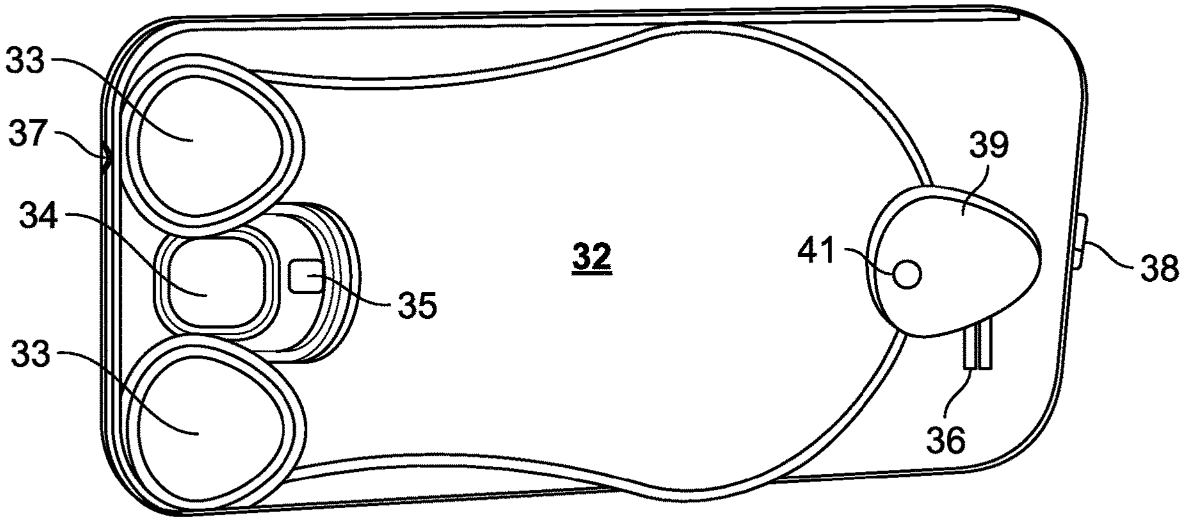
FIG. 5B is a back view of an embodiment of the stimulator shown in FIG. 5A according to this disclosure.
Figure 5C:
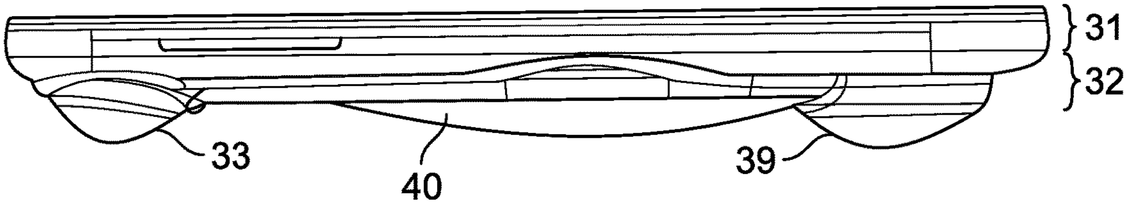
FIG. 5C is a side view of an embodiment of the stimulator shown in FIG. 5A according to this disclosure.

Another embodiment of the electrode-based stimulator is shown in FIG. 5, showing a device in which electrically conducting material is dispensed from the device to the patient's skin. In this embodiment, the interface (351 in FIG. 2B) is the conducting material itself. FIGS. 5A and 5B respectively provide top and bottom views of the outer surface of the electrical stimulator 50. FIG. 5C provides a bottom view of the stimulator 50, after sectioning along its long axis to reveal the inside of the stimulator.

Figure 4A:
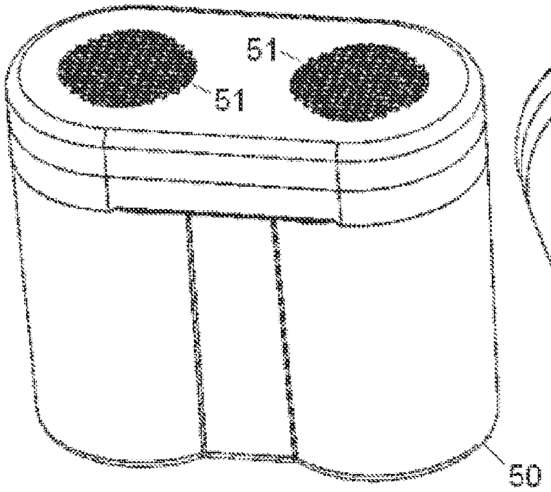
FIG. 4A is perspective view of the top of an alternative embodiment of a stimulator according to the present invention.
Figure 4B:
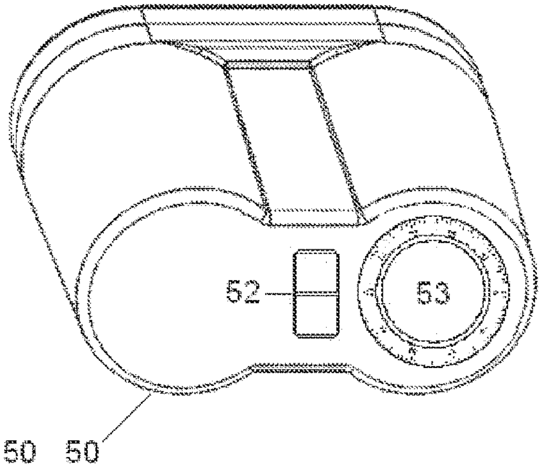
FIG. 4B is a perspective view of the bottom of the stimulator of FIG. 4A.

FIGS. 4A-4D show a mesh 51 with openings that permit a conducting gel to pass from inside of the stimulator to the surface of the patient's skin at the position of nerve or tissue stimulation. Thus, the mesh with openings 51 is the part of the stimulator that is applied to the skin of the patient, through which conducting material may be dispensed. In any given stimulator, the distance between the two mesh openings 51 in FIG. 4A is constant, but it is understood that different stimulators may be built with different inter-mesh distances, in order to accommodate the anatomy and physiology of individual patients. Alternatively, the inter-mesh distance may be made variable as in the eyepieces of a pair of binoculars. A covering cap (not shown) is also provided to fit snugly over the top of the stimulator housing and the mesh openings 51, in order to keep the housing's conducting medium from leaking or drying when the device is not in use.

Figure 4C:
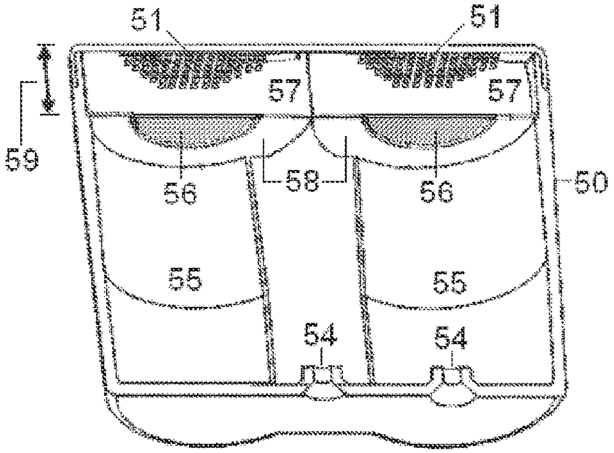
FIG. 4C is a cut-a-way view of the stimulator of FIG. 4A.
Figure 4D:
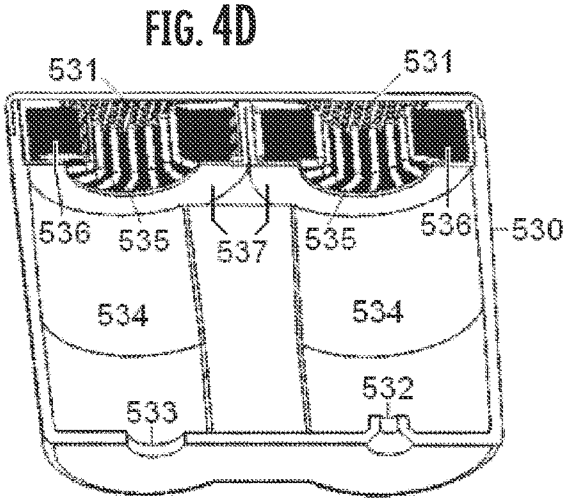
FIG. 4D is another cut-a-way view of the stimulator of FIG. 4A.

FIGS. 4C and 4D show the bottom of the self-contained stimulator 50. An on/off switch 52 is attached through a port 54, and an energy-level controller 53 is attached through another port 54. The switch is connected to a battery energy source (320 in FIG. 1), and the energy-level controller is attached to the control unit (330 in FIG. 1) of the device. The energy source battery and energy-level controller, as well as the impulse generator (310 in FIG. 1) are located (but not shown) in the rear compartment 55 of the housing of the stimulator 50.

Individual wires (not shown) connect the impulse generator 310 to the stimulator's electrodes 56. The two electrodes 56 are shown here to be elliptical metal discs situated between the head compartment 57 and rear compartment 55 of the stimulator 50. A partition 58 separates each of the two head compartments 57 from one another and from the single rear compartment 55. Each partition 58 also holds its corresponding electrode in place. However, each electrode 56 may be removed to add electrically conducting gel 350 to each head compartment 57. An optional non-conducting variable-aperture iris diaphragm may be placed in front of each of the electrodes within the head compartment 57, in order to vary the effective surface area of each of the electrodes. Each partition 58 may also slide towards the head of the device in order to dispense conducting gel through the mesh apertures 51. The position of each partition 58 therefore determines the distance 59 between its electrode 56 and mesh openings 51, which is variable in order to obtain the optimally uniform current density through the mesh openings 51. The outside housing of the stimulator 50, as well as each head compartment 57 housing and its partition 58, are made of electrically insulating material, such as acrylonitrile butadiene styrene, so that the two head compartments are electrically insulated from one another. Although the embodiment in FIG. 4 is shown to be a non-capacitive stimulator, it is understood that it may be converted into a capacitive stimulator by replacing the mesh openings 51 with a dielectric material, such as a sheet of Mylar, or by covering the mesh openings 51 with a sheet of such dielectric material.

In preferred embodiments of the electrode-based stimulator shown in FIG. 4, electrodes are made of a metal, such as stainless steel, platinum, or a platinum-iridium alloy. However, in other embodiments, the electrodes may have many other sizes and shapes, and they may be made of other materials [Thierry KELLER and Andreas Kuhn. Electrodes for transcutaneous (surface) electrical stimulation. Journal of Automatic Control, University of Belgrade, 18 (2,2008): 35-45; G. M. LYONS, G. E. Leane, M. Clarke-Moloney, J. V. O'Brien, P. A. Grace. An investigation of the effect of electrode size and electrode location on comfort during stimulation of the gastrocnemius muscle. Medical Engineering & Physics 26 (2004) 873-878; Bonnie J. FORRESTER and Jerrold S. Petrofsky. Effect of Electrode Size, Shape, and Placement During Electrical Stimulation. The Journal of Applied Research 4, (2, 2004): 346-354; Gad ALON, Gideon Kantor and Henry S. Ho. Effects of Electrode Size on Basic Excitatory Responses and on Selected Stimulus Parameters. Journal of Orthopaedic and Sports Physical Therapy. 20 (1,1994):29-35].

For example, the stimulator's conducting materials may be nonmagnetic, and the stimulator may be connected to the impulse generator by long nonmagnetic wires (345 in FIG. 2B), so that the stimulator may be used in the vicinity of a strong magnetic field, possibly with added magnetic shielding. As another example, there may be more than two electrodes; the electrodes may comprise multiple concentric rings; and the electrodes may be disc-shaped or have a non-planar geometry. They may be made of other metals or resistive materials such as silicon-rubber impregnated with carbon that have different conductive properties [Stuart F. COGAN. Neural Stimulation and Recording Electrodes.

Annu. Rev. Biomed. Eng. 2008. 10:275-309; Michael F. NOLAN. Conductive differences in electrodes used with transcutaneous electrical nerve stimulation devices. Physical Therapy 71 (1991):746-751].

The electrode-based stimulator designs shown in FIGS. 3 and 4 situate the electrode remotely from the surface of the skin within a chamber. Such a chamber design had been used prior to the availability of flexible, flat, disposable electrodes [patent U.S. Pat. No. 3,659,614, entitled Adjustable headband carrying electrodes for electrically stimulating the facial and mandibular nerves, to Jankelson; U.S. Pat. No. 3,590,810, entitled Biomedical body electrode, to Kopecky; U.S. Pat. No. 3,279,468, entitled Electrotherapeutic facial mask apparatus, to Le Vine; U.S. Pat. No. 6,757,556, entitled Electrode sensor, to Gopinathan et al; U.S. Pat. No. 4,383, 529, entitled Iontophoretic electrode device, method and gel insert, to Webster; U.S. Pat. No. 4,220,159, entitled Electrode, to Francis et al. U.S. Pat. Nos. 3,862,633, 4,182,346, and 3,973,557, entitled Electrode, to Allison et al; U.S. Pat. No. 4,215,696, entitled Biomedical electrode with pressurized skin contact, to Bremer et al; and U.S. Pat. No. 4,166,457, entitled Fluid self-sealing bioelectrode, to Jacobsen et al.] The stimulator designs shown in FIGS. 4 and 5 are also self-contained units, housing the electrodes, signal electronics, and energy supply. Portable stimulators are also known in the art, for example, U.S. Pat. No. 7,171,266, entitled Electro-acupuncture device with stimulation electrode assembly, to Gruzdowich. One of the novelties of the designs shown in FIGS. 3 and 4 is that the stimulator, along with a correspondingly suitable stimulation waveform, shapes the electric field, producing a selective physiological response by stimulating that nerve, but avoiding substantial stimulation of nerves and tissue other than the target nerve, particularly avoiding the stimulation of nerves that produce pain. The shaping of the electric field is described in terms of the corresponding field equations in commonly assigned application US20210230938 (application Ser. No. 13/075, 746) entitled Devices and methods for non-invasive electrical stimulation and their use for vagal nerve stimulation on the neck of a patient, to SIMON et al., which is hereby incorporated by reference.

As seen in FIG. 4D, a mesh 531 has openings that permit a conducting gel within 351 to pass from the inside of the stimulator to the surface of the patient's skin at the location of nerve or tissue stimulation. Thus, the mesh with openings 531 is the part of the magnetic stimulator that is applied to the skin of the patient.

Another embodiment of an electrode-based stimulator is shown in FIGS. 5A-5C. As shown, the stimulator comprises a smartphone (31) with its back cover removed and joined to a housing (32) that comprises a pair of electrode surfaces (33) along with circuitry to control and energy the electrodes and interconnect with the smartphone. The electrode surface (33) in FIGS. 5A-5C corresponds to item 351 in FIG. 1. FIG. 5A shows the side of the smartphone (31) with a touch-screen. FIG. 5B shows the housing of the stimulator (32) joined to the back of the smartphone. Portions of the housing lie flush with the back of the smartphone, with windows to accommodate smartphone components that are found on the original back of the smartphone. Such components may also be used with the stimulator, e.g., the smartphone's rear camera (34), flash (35) and speaker (36). Other original components of the smartphone may also be used, such as the audio headset jack socket (37) and multi-purpose jack (38). Note that the original components of the smartphone shown in FIG. 5 correspond to a Samsung Galaxy smartphone, and their locations may be different for embodiments that use different smartphone models by different smartphone manufacturers. Note that tablets can be used as well.

FIG. 5C shows that several portions of the housing (32) protrude towards the back. The two electrode surfaces (33) protrude so that they may be applied to the skin of the patient. The stimulator may be held in place by straps or frames or collars, or the stimulator may be held against the patient's body by hand. In some embodiments, the neurostimulator may comprise a single such electrode surface or more than two electrode surfaces.

A dome (39) also protrudes from the housing, so as to allow the device to lie more or less flat on a table when supported also by the electrode surfaces. The dome also accommodates a relatively tall component that may lie underneath it, such as a battery. Alternatively, the stimulation device may be energized by the smartphone's battery. If the battery under the dome is rechargeable, the dome may contain a socket (41) through which the battery is recharged using a jack that is inserted into it, which is, for example, attached to a energy cable from a base station (described below). The belly (40) of the housing protrudes to a lesser extent than the electrodes and dome. The belly accommodates a printed circuit board that contains electronic components within the housing (not shown), as described below.

Electronics and Software of the Stimulator

In some embodiments, the signal waveform (FIG. 2) that is to be applied to electrodes of the stimulator is initially generated in a component of the impulse generator 310 that is exterior to, and remote from, the mobile phone housing. The mobile phone preferably includes a software application that can be downloaded (e.g., mobile app store, USB cable, memory stick, Bluetooth connection) into the phone to receive, from the external control component, a wirelessly transmitted waveform, or to receive a waveform that is transmitted by cable, e.g., via the multi-purpose jack 38 in FIG. 5. If the waveforms are transmitted in compressed form, they are preferably compressed in a lossless manner, e.g., making use of FLAC (Free Lossless Audio Codec). Alternatively, the downloaded software application may itself be coded to generate a particular waveform that is to be applied to the electrodes (340 in FIG. 1C) and subsequently conveyed to the external interface of the electrode assembly (351 in FIGS. 1C and 33 in FIG. 5). In some embodiments, the software application is not downloaded from outside the device, but is instead available internally, for example, within read-only-memory that is present within the housing of the stimulator (32 in FIGS. 3B and 3C).

In some embodiments, the waveform is first conveyed by the software application to contacts within the phone's speaker output or the earphone jack socket (37 in FIG. 3B), as though the waveform signal were a generic audio waveform. That pseudo-audio waveform will generally be a stereo waveform, representing signals that are to be applied to the "left" and "right" electrodes. The waveform will then be conveyed to the housing of the stimulator (32 in FIGS. 3B and 3C), as follows. The housing of the stimulator may have an attached dangling audio jack that is plugged into the speaker output or the earphone jack socket 37 whenever electrical stimulation is to be performed, or the electrical connection between the contacts of the speaker output or the earphone jack socket and the housing of the stimulator may be hard-wired. In either case, electrical circuits on a printed circuit board located under the belly of the housing (40 in FIG. 3C) of the stimulator may then shape, filter, and/or amplify the pseudo-audio signal that is received via the speaker output or earphone jack socket. An energy amplifier within the housing of the stimulator may then drive the signal onto the electrodes, in a fashion that is analogous to the use of an audio energy amplifier to drive loudspeakers. Alternatively, the signal processing and amplification may be implemented in a separate device that can be plugged into sockets on the phone and/or housing of the stimulator (32 in FIGS. 3B and 3C), to couple the software application and the electrodes.

In addition to passing the stimulation waveform from the smartphone to the stimulator housing as described herein, the smartphone may also pass control signals to the stimulator housing. Thus, the stimulation waveform may generally be regarded as a type of analog, pseudo-audio signal, but if the signal contains a signature series of pulses signifying that a digital control signal is about to be sent, logic circuitry in the stimulator housing may then be set to decode the series of digital pulses that follows the signature series of pulses, analogous to the operation of a modem.

Many of the steps that direct the waveform to the electrodes, including steps that may be controlled by the user via the touchscreen (31 in FIG. 3A), are implemented in the above-mentioned software application. By way of example, the software application may be written for a phone that uses the Android operating system. Such applications are typically developed in the Java programming language using the Android Software Development Kit (SDK), in an integrated development environment (IDE), such as Eclipse [Mike WOLFSON. Android Developer Tools Essentials. Sebastopol, Calif.: O'Reilly Media Inc., 2013; Ronan SCHWARZ, Phil Duston, James Steele, and Nelson To. The Android Developer's Cookbook. Building Applications with the Android SDK, Second Edition. Upper Saddle River, NJ: Addison-Wesley, 2013, the disclosure of which is incorporated herein by reference for all purposes as if copied and pasted herein; Shane CONDER and Lauren Darcey. Android Wireless Application Development, Second Edition. Upper Saddle River, NJ: Addison-Wesley, 2011; Jerome F. DIMARZIO. Android—A Programmer's Guide. New York: McGraw-Hill. 2008. pp. 1-319, the disclosure of which is incorporated herein by reference for all purposes as if copied and pasted herein]. Application programming interfaces (APIs) that are particularly relevant to the audio features of such an Android software application (e.g., MediaPlayer APIs) are described by: Android Open Source Project of the Open Handset Alliance. Media Playback, at web domain developer.android.com with subdomain/guide/topics/media/, Jul. 18, 2014, the disclosure of which is incorporated herein by reference for all purposes as if copied and pasted herein. Those APIs can be relevant to a use of the smartphone camera capabilities, as described below. Additional components of the software application are available from device manufacturers [Samsung Mobile SDK, at web domain developer.samsung.com with subdomain/samsung-mobile-sdk, Jul. 18, 2014, the disclosure of which is incorporated herein by reference for all purposes as if copied and pasted herein].

In some embodiments, the stimulator and/or smartphone will include a user control, such as a switch or button, that disables/enables the stimulator. Preferably, the switch will automatically disable some, many, most, or all smartphone functions when the stimulator is enabled (and vice versa). This ensures that the medical device functionality of the smartphone is completely segregated from the rest of the phone's functionality. In some embodiments, the switch will be password-controlled such that only the patient/owner of the stimulator/phone will be able to enable the stimulator functionality. In one such embodiment, the switch will be controlled by a biometric scan (e.g., fingerprint, optical scan or the like) such that the stimulator functionality can only be used by the patient. This ensures that only the patient will be able to use the prescribed therapy in the event the phone is lost or stolen.

The stimulator and/or phone can also include software that allows the patient to order more therapy doses over the internet (discussed in more detail below in connection with the docking station). The purchase of such therapy doses will require physician authorization through a prescription or the like. To that end, the software can include an authorization code for entry in order for the patient to download authorization for more therapies. In some embodiments, without such authorization, the stimulator will be disabled and will not deliver therapy.

Although the device shown in FIG. 5 is an adapted commercially available smartphone, it is understood that in some embodiments, the housing of the stimulator may also be joined to and/or energized by a wireless device that is not a phone (e.g., Wi-Fi enabled device, wearable, tablet). Alternatively, the stimulator may be coupled to a phone or other Wi-Fi enabled device through a wireless connection for exchanging data at short distances, such as Bluetooth or the like. In this embodiment, the stimulator housing is not attached to the smartphone and, therefore, may comprise a variety of other shapes and sizes that are convenient for the patient to carry in his or her purse, wallet or pocket.

In some embodiments, the stimulator housing may be designed as part of a protective or decorative case for the phone that can be attached to the phone, similar to standard phone cases. In one such embodiment, the stimulator/case may also include additional battery life for the phone and may include an electrical connection to the phone's battery to recharge the battery (e.g., part of a Mophie® or the like). This electrical connection may also be used to couple the smartphone to the stimulator.

Embodiments with Distributed Controllers

In some embodiments, significant portions of the control of the vagus nerve stimulation reside in controller components that are physically separate from the housing of the stimulator. In these embodiment, separate components of the controller and stimulator housing generally communicate with one another wirelessly, although wired or waveguide communication is possible. Thus, the use of wireless technology avoids the inconvenience and distance limitations of interconnecting cables. Additional reasons in the present disclosure for physically separating many components of the controller from the stimulator housing are as follows.

First, the stimulator may be constructed with the minimum number of components needed to generate the stimulation pulses, with the remaining components placed in parts of the controller that reside outside the stimulator housing, resulting in a lighter and smaller stimulator housing. In fact, the stimulator housing may be made so small that it could be difficult to place, on the stimulator housing's exterior, switches and knobs that are large enough to be operated easily. Instead, for the present disclosure, the user may generally operate the device using the smartphone touchscreen.

Second, the controller 330 may be given additional functions when free from the limitation of being situated within or near the stimulator housing. For example, one may add to the controller a data logging component that records when and how stimulation has been applied to the patient, for purposes of medical recordkeeping and billing. The complete electronic medical record database for the patient may be located far from the stimulator (e.g., somewhere on the internet), and the billing system for the stimulation services that are provided may also be elsewhere, so it would be useful to integrate the controller into that recordkeeping and billing system, using a communication system that includes access to the internet or telephone networks.

Third, communication from the databases to the controller would also be useful for purposes of metering electrical stimulation of the patient, when the stimulation is self-administered. For example, if the prescription for the patient only permits only a specified amount of stimulation energy to be delivered during a single session of vagus nerve stimulation, followed by a wait-time before allowing the next stimulation, the controller can query the database and then permit the stimulation only when the prescribed wait-time has passed. Similarly, the controller can query the billing system to assure that the patient's account is in order, and withhold the stimulation if there is a problem with the account.

Fourth, as a corollary of the previous considerations, the controller may be constructed to include a computer program separate from the stimulating device, in which the databases are accessed via cell phone or internet connections.

Fifth, in some applications, it may be desired that the stimulator housing and parts of the controller be physically separate. For example, when the patient is a child, one wants to make it impossible for the child to control or adjust the vagus nerve stimulation. The best arrangement in that case is for the stimulator housing to have no touchscreen elements, control switches or adjustment knobs that could be activated by the child. Alternatively, any touchscreen elements, switches and knobs on the stimulator can be disabled, and control of the stimulation then resides only in a remote controller with a child-proof operation, which would be maintained under the control of a parent or healthcare provider.

Sixth, in some applications, the particular control signal that is transmitted to the stimulator by the controller will depend on physiological and environmental signals that are themselves transmitted to and analyzed by the controller. In such applications, many of the physiological and environmental signals may already be transmitted wirelessly, in which case it is most convenient to design an external part of the controller as the hub of all such wireless activity, including any wireless signals that are sent to and from the stimulator housing.

With these considerations in mind, an embodiment of can include a base station 332 (FIG. 6) that may send/receive data to/from the stimulator, and may send/receive data to/from databases and other components of the system, including those that are accessible via the internet (or another network such as local area, wide area, satellite, cellular). Typically, the base station will be a laptop computer attached to additional components needed for it to accomplish its function. Thus, prior to any particular stimulation session, the base station may load into the stimulator parameters of the session, including waveform parameters, or the actual waveform.

In some embodiments, the base station is also used to limit the amount of stimulation energy that may be consumed by the patient during the session, by charging the stimulator's rechargeable battery with only a specified amount of releasable electrical energy, which is different than setting a parameter to restrict the duration of a stimulation session. Thus, the base station may comprise a energy supply that may be connected to the stimulator's rechargeable battery, and the base station meters the recharge. As a practical matter, the stimulator may therefore use two batteries, one for applying stimulation energy to the electrodes (the charge of which may be limited by the base station) and the other for performing other functions. Methods for evaluating a battery's charge or releasable energy can be as disclosed in U.S. Pat. No. 7,751,891, entitled Energy supply monitoring for an implantable device, to ARMSTRONG et al, the disclosure of which is incorporated herein by reference for all purposes as if copied and pasted herein. Alternatively, some control components within the stimulator housing may monitor the amount of electrode stimulation energy that has been consumed during a stimulation session and stop the stimulation session when a limit has been reached, irrespective of the time when the limit has been reached.

Figure 6:
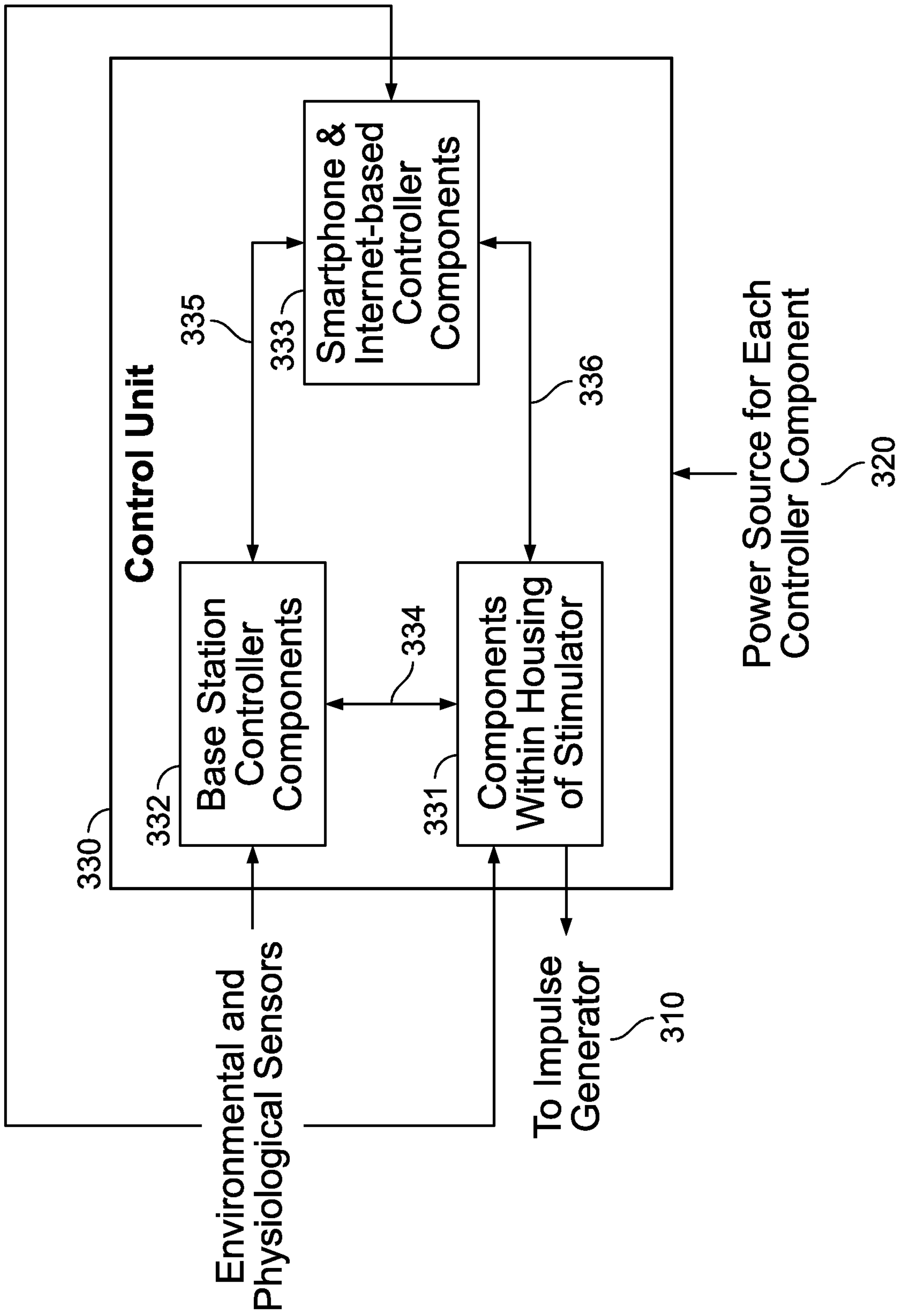
FIG. 6 shows an expanded diagram of an embodiment of a control unit according to the present disclosure.

The communication connections between different components of the stimulator's controller are shown in FIG. 6, which is an expanded representation of the control unit 330 in FIG. 1. Connection between the base station controller components 332 and components within the stimulator housing 331 is denoted in FIG. 6 as 334. Connection between the base station controller components 332 and internet-based (or network based) or smartphone components 333 is denoted as 335. Connection between the components within the stimulator housing 331 and internet-based or smartphone components 333 is denoted as 336. For example, control connections between the smartphone and stimulator housing via the audio jack socket would fall under this category, as would any wireless communication directly between the stimulator housing itself and a device situated on the internet. In principle, the connections 334, 335 and 336 in FIG. 6 may be either wired or wireless or waveguide-based. Different embodiments may lack one or more of the connections.

Although infrared or ultrasound wireless control might be used to communicate between components of the controller, they are not preferred because of line-of-sight limitations. Instead, in the present disclosure, the communication between devices preferably makes use of radio communication within unlicensed ISM frequency bands (260-470 MHz, 902-928 MHz, 2400-2.4835 GHz). Components of the radio frequency system in devices in 331, 332, and 333 typically comprise a system-on-chip transceiver with an integrated microcontroller; a crystal; associated balun & matching circuitry, and an antenna [Dag GRINI. RF Basics, RF for Non-RF Engineers. Texas Instruments, Post Office Box 655303, Dallas, Tex. 75265, 2006, the disclosure of which is incorporated herein by reference for all purposes as if copied and pasted herein].

Transceivers based on 2.4 GHz offer high data rates (greater than 1 Mbps) and a smaller antenna than those operating at lower frequencies, which makes them suitable for with short-range devices. Furthermore, a 2.4 GHz wireless standard (e.g., Bluetooth, Wi-Fi, and ZigBee) may be used as the protocol for transmission between devices. Although the ZigBee wireless standard operates at 2.4 GHz in most jurisdictions worldwide, it also operates in the ISM frequencies 868 MHz in Europe, and 915 MHz in the USA and Australia. Data transmission rates vary from 20 to 250 kilobits/second with that standard. Because many commercially available health-related sensors may operate using ZigBee, its use may be recommended for applications in which the controller uses feedback and feedforward methods to adjust the patient's vagus nerve stimulation based on the sensors' values, as described below in connection with FIG. 11 [ZigBee Wireless Sensor Applications for Health, Wellness and Fitness. ZigBee Alliance 2400 Camino Ramon Suite 375 San Ramon, CA 94583].

A 2.4 GHz radio has higher energy consumption than radios operating at lower frequencies, due to reduced circuit efficiencies. Furthermore, the 2.4 GHz spectrum is crowded and subject to significant interference from microwave ovens, cordless phones, 802.11b/g wireless local area networks, Bluetooth devices, etc. Sub-GHz radios enable lower energy consumption and can operate for years on a single battery. These factors, combined with lower system cost, make sub-GHz transceivers ideal for low data rate applications that need maximum range and multi-year operating life.

The antenna length needed for operating at different frequencies is 17.3 cm at 433 MHz, 8.2 cm at 915 MHz, and 3 cm at 2.4 GHz. Therefore, unless the antenna is included in a neck collar that supports the device shown in FIG. 3, the antenna length may be a disadvantage for 433 MHz transmission. The 2.4 GHz band has the advantage of enabling one device to serve in all major markets worldwide since the 2.4 GHz band is a global spectrum standard. However, 433 MHz is a viable alternative to 2.4 GHz for most of the world, and designs based on 868 and 915 MHz radios can serve the U.S. and European markets with a single product.

Range is determined by the sensitivity of the transceiver and its output energy. A primary factor affecting radio sensitivity is the data rate. Higher data rates reduce sensitivity, leading to a need for higher output energy to achieve sufficient range. For many applications that require only a low data rate, the preferred rate is 40 Kbps where the transceiver can still use a standard off-the-shelf 20 parts per million crystal.

A signal waveform that might be transmitted wirelessly to the stimulator housing was shown in FIGS. 2B and 2C. As seen there, individual sinusoidal pulses have a period of tau, and a burst consists of N such pulses. This is followed by a period with no signal (the inter-burst period). The pattern of a burst followed by silent inter-burst period repeats itself with a period of T. For example, the sinusoidal period tau may be 200 microseconds; the number of pulses per burst may be N=5; and the whole pattern of burst followed by silent inter-burst period may have a period of T=40000 microseconds, which is comparable to 25 Hz stimulation (a much smaller value of T is shown in FIG. 2C to make the bursts discernable). When these exemplary values are used for T and tau, the waveform contains significant Fourier components at higher frequencies (1/200 microseconds=5000/sec). Such a signal may be easily transmitted using 40 Kbps radio transmission. Compression of the signal is also possible, by transmitting only the signal parameters tau, N, T, Emax, etc., but in that case the stimulator housing's control electronics would then have to construct the waveform from the transmitted parameters, which would add to the complexity of components of the stimulator housing.

However, because it is contemplated that sensors attached to the stimulator housing may also be transmitting information, the data transfer requirements may be substantially greater than what is required only to transmit the signal shown in FIG. 2. Therefore, the present disclosure may make use of any frequency band, not limited to the ISM frequency bands, as well as techniques known in the art to suppress or avoid noise and interferences in radio transmission, such as frequency hopping and direct sequence spread spectrum.

Applications of Stimulators to the Patient

Selected nerve fibers are stimulated in different embodiments of methods that make use of the disclosed electrical stimulation devices, including stimulation of the vagus nerve at a location in the patient's neck. At that location, the vagus nerve is situated within the carotid sheath, near the carotid artery and the interior jugular vein. The carotid sheath is located at the lateral boundary of the retropharyngeal space on each side of the neck and deep to the sternocleidomastoid muscle. The left vagus nerve is sometimes selected for stimulation because stimulation of the right vagus nerve may produce undesired effects on the heart, but depending on the application, the right vagus nerve or both right and left vagus nerves may be stimulated instead.

Of course, it will be recognized that the vagus nerve may be stimulated through other mechanisms. For example, auricular vagal nerve stimulation involves stimulation of the auricular branch of the vagus nerve, often termed the Alderman's nerve or Arnold's nerve. This nerve may be stimulated through the transcutaneous systems and methods described herein by transmitting electrical impulses through the outer skin surface of the patient's ear to the auricular branch of the vagus nerve.

The three major structures within the carotid sheath are the common carotid artery, the internal jugular vein and the vagus nerve. The carotid artery lies medial to the internal jugular vein, and the vagus nerve is situated posteriorly between the two vessels. Typically, the location of the carotid sheath or interior jugular vein in a patient (and therefore the location of the vagus nerve) will be ascertained in any manner known in the art, e.g., by feel or ultrasound imaging. Proceeding from the skin of the neck above the sternocleidomastoid muscle to the vagus nerve, a line may pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein might be preferred for non-invasive stimulation of the vagus nerve. The magnetic stimulator coil may be centered on such a point, at the level of about the fifth to sixth cervical vertebra shows an embodiment of a location of a stimulation as "Vagus Nerve Stimulation," relative to its connections with other anatomical structures that are potentially affected by the stimulation. In some embodiments, various brain and brainstem structures are modulated by the stimulation. These structures are described in sections of the disclosure that follow, along with some rationale for modulating their activity as a prevention, prophylaxis, diagnosis, monitoring, amelioration, or treatment of various medical conditions, diseases or disorders.

Figure 7:
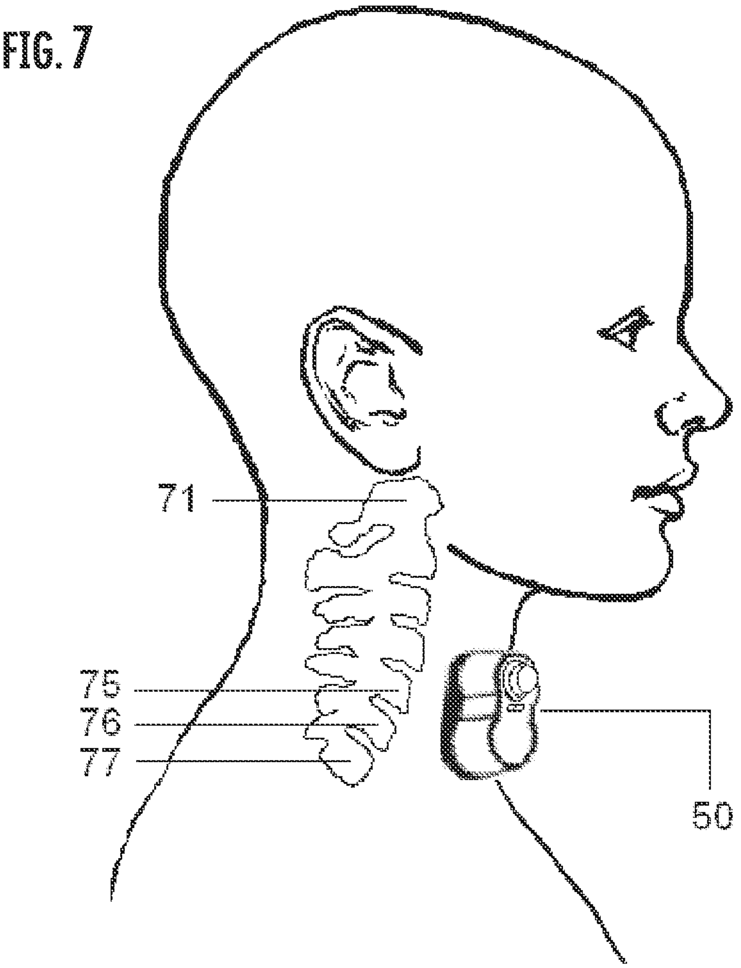
FIG. 7 illustrates an embodiment of an approximate position of a stimulator according to this disclosure, when used to stimulate a right vagus nerve in a neck of an adult patient.

FIG. 7 illustrates use of the device 50 to stimulate the vagus nerve at that location in the neck, in which the stimulator device 50 is shown to be applied to the target location on the patient's neck as described herein. For reference, FIG. 7 shows the locations of the following vertebrae: first cervical vertebra 71, the fifth cervical vertebra 75, the sixth cervical vertebra 76, and the seventh cervical vertebra 77.

Figure 8:
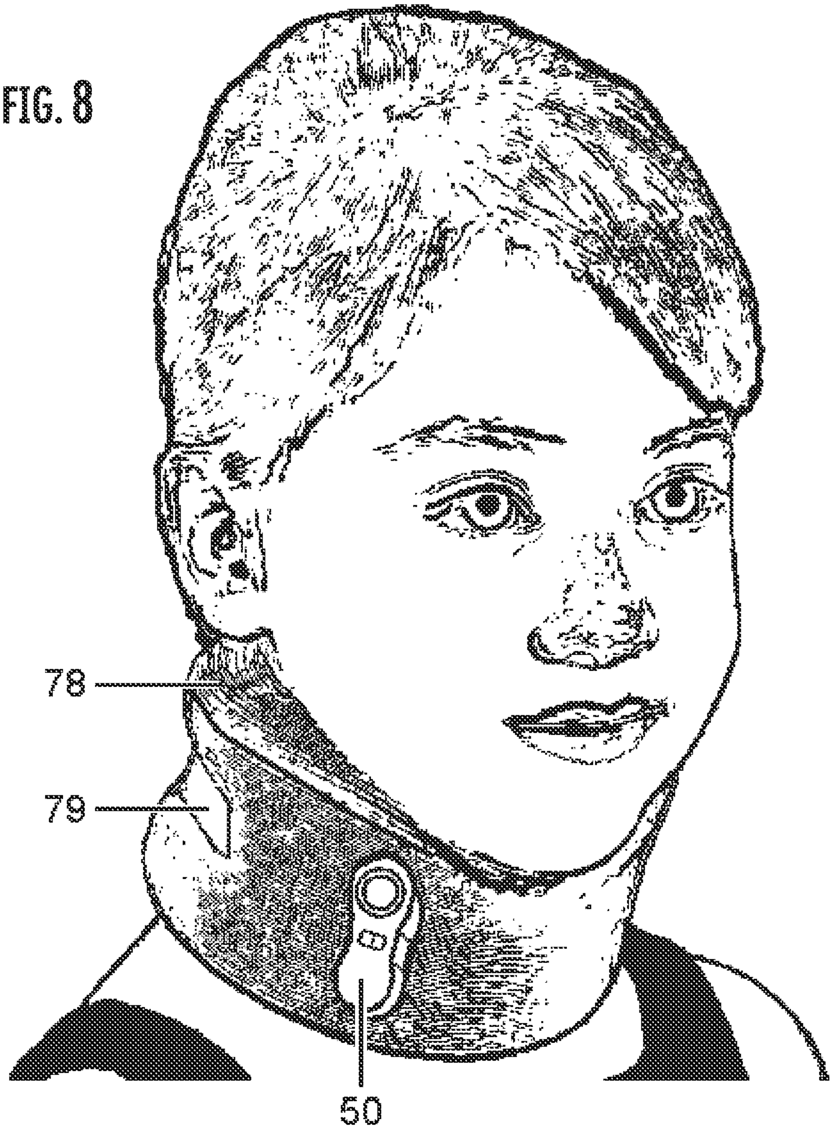
FIG. 8 illustrates an embodiment of an approximate position of a stimulator according to this disclosure, when used to stimulate a right vagus nerve in a neck of a child who wears a collar to hold the stimulator.

FIG. 8 shows the stimulator 30 applied to the neck of a child, which is partially immobilized with a foam cervical collar 78 that is similar to ones used for neck injuries and neck pain. The collar is tightened with a strap 79, and the stimulator is inserted through a hole in the collar to reach the child's neck surface. In such applications, the stimulator may be turned on and off remotely, using a wireless controller that may be used to adjust the stimulation parameters of the controller (e.g., on/off, stimulation amplitude, frequency, etc.).

Figure 9:
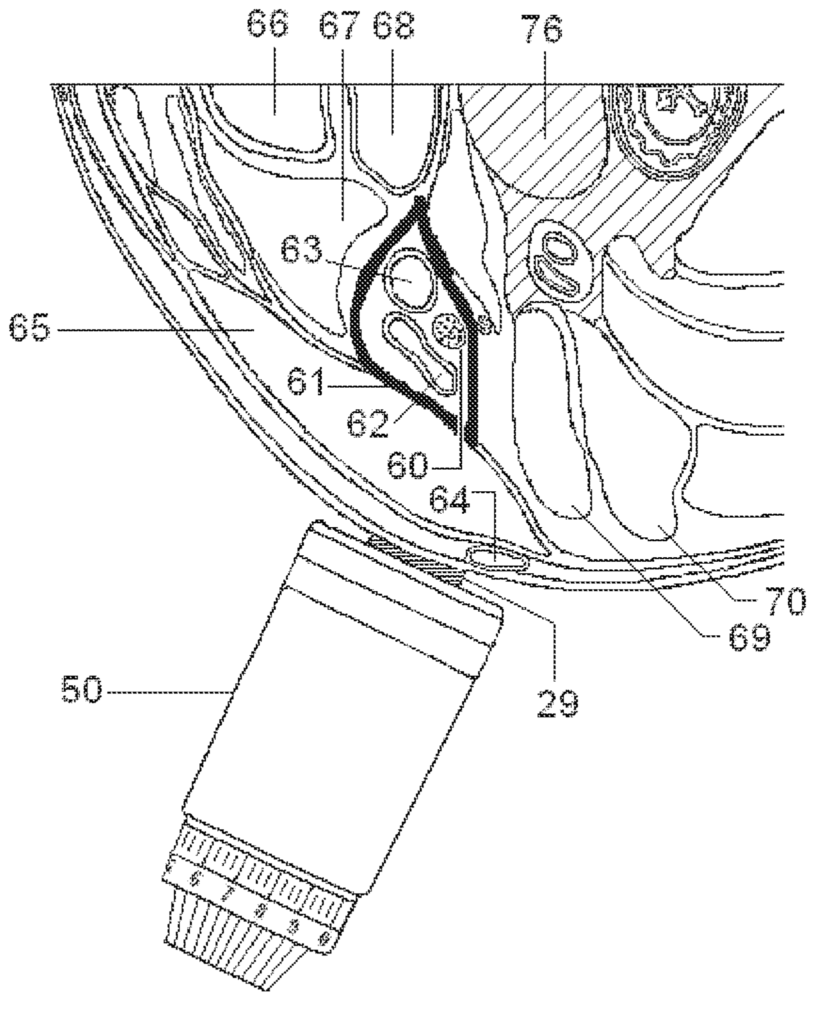
FIG. 9 illustrates an embodiment of a stimulator according to this disclosure, when positioned to stimulate a vagus nerve in a patient's neck, wherein the stimulator is applied to a surface of the neck in a vicinity of various identified anatomical structures.

FIG. 9 provides a more detailed view of use of the electrical stimulator 30, when positioned to stimulate the vagus nerve at the neck location. The anatomy shown in FIG. 9 is a cross-section of half of the neck at vertebra level C6. The vagus nerve 60 is identified in FIG. 9, along with the carotid sheath 61 that is identified there in bold peripheral outline. The carotid sheath encloses not only the vagus nerve, but also the internal jugular vein 62 and the common carotid artery 63. Structures that may be identified near the surface of the neck include the external jugular vein 64 and the sternocleidomastoid muscle 65, which protrudes when the patient turns his or her head. Additional organs in the vicinity of the vagus nerve include the trachea 66, thyroid gland 67, esophagus 68, *Scalenus anterior* muscle 69, *Scalenus medius* muscle 70, levator scapulae muscle 71, splenius colli muscle 72, semispinalis capitis muscle 73, semispinalis colli muscle 74, longus colli muscle and longus capitis muscle 75. The sixth cervical vertebra 76 is shown with bony structure indicated by hatching marks. Additional structures shown in the figure are the phrenic nerve 77, sympathetic ganglion 78, brachial plexus 79, vertebral artery and vein 80, prevertebral fascia 81, platysma muscle 82, omohyoid muscle 83, anterior jugular vein 84, sternohyoid muscle 85, sternothyroid muscle 86, and skin with associated fat 87.

Stimulation may be performed on the left or right vagus nerve or on both of them simultaneously and alternately. The position and angular orientation of the device are adjusted about that location until the patient perceives stimulation when current is passed through the stimulator electrodes. The applied current is increased gradually, first to a level wherein the patient feels sensation from the stimulation. The energy is then increased, but is set to a level that is less than one at which the patient first indicates any discomfort. Straps, harnesses, or frames may be used to maintain the stimulator in position. The stimulator signal may have a frequency and other parameters that are selected to produce a therapeutic result in the patient, i.e., stimulation parameters for each patient are adjusted on an individualized basis. Ordinarily, the amplitude of the stimulation signal is set to the maximum that is comfortable for the patient, and then the other stimulation parameters are adjusted.

The stimulation is then performed with a sinusoidal burst waveform like that shown in FIG. 2. As seen there, individual sinusoidal pulses have a period of T, and a burst consists of N such pulses. This is followed by a period with no signal (the inter-burst period). The pattern of a burst followed by silent inter-burst period repeats itself with a period of T. For example, the sinusoidal period T may be between about 50-1000 microseconds and a frequency of about 1-20 kHz, preferably between about 100-400 microseconds and a frequency of about 2.5-10 kHz, more preferably about 133-400 microseconds and a frequency of about 2.5-7.5 kHz and even more preferably about 200 microseconds and a frequency of about 5 kHz; the number of pulses per burst may be N=1-20, preferably about 2-10 and more preferably about 5; and the whole pattern of burst followed by silent inter-burst period may have a period T comparable to about 5-100 Hz, preferably about 15-50 Hz, more preferably about 25-35 Hz and even more preferably about 25 Hz (a much smaller value of T is shown in FIG. 2C to make the bursts discernable). When these example values are used for T and T, the waveform contains significant Fourier components at higher frequencies (1/200 microseconds=5000/sec), as compared with those contained in transcutaneous nerve stimulation waveforms.

When a patient is using the stimulation device to perform self-stimulation therapy, e.g., at home or at a workplace, he or she will follow the steps that are now described. It is assumed that the optimal stimulation position has already been marked on the patient's neck, as described above and that a reference image of the fluorescent spots has already been acquired. The previous stimulation session will ordinarily have discharged the rechargeable batteries of the stimulator housing, and between sessions, the base station will have been used to recharge the stimulator at most only up to a minimum level. If the stimulator's batteries had charge remaining from the previous stimulation session, the base station will discharge the stimulator to a minimum level that will not support stimulation of the patient.

The patient can initiate the stimulation session using the mobile phone or base station (e.g., laptop computer) by invoking a computer program (on the laptop computer or through an app on the mobile phone) that is designed to initiate use of the stimulator. The programs in the smartphone and base station may initiate and interact with one another wirelessly, so in what follows, reference to the program (app) in the smartphone may also apply to the program in the base station, because both may be operating in tandem. For security reasons, the program would begin with the request for a user name and a password, and that user's demographic information and any data from previous stimulator experiences would already be associated with it in the login account. The smartphone may also be used to authenticate the patient using a fingerprint or voice recognition app, or other reliable authentication methods. If the patient's physician has not authorized further treatments, the base station will not charge the stimulator's batteries, and instead, the computer program will call or otherwise communicate with the physician's computer requesting authorization. After authorization by the physician is received, the computer program (on the laptop computer or through an app on the mobile phone) may also query a database that is ordinarily located somewhere on the internet to verify that the patient's account is in order. If it is not in order, the program may then request prepayment for one or more stimulation sessions, which would be paid by the patient using a credit card, debit card, PayPal, cryptocurrency, bitcoin, or the like. The computer program will also query its internal database or that of the base station to determine that sufficient time has elapsed between when the stimulator was last used and the present time, to verify that any required wait-time has elapsed.

Having received authorization to perform a nerve stimulation session, the patient interface computer program will then ask the patient questions that are relevant to the selection of parameters that the base station will use to make the stimulator ready for the stimulation session. The questions that the computer program asks are dependent on the condition for which the patient is being treated, which for present purposes is considered to be treatment for an autoimmune disease or disorder. The questions may be things like (1) is this an acute or prophylactic treatment? (2) if acute, then how severe is your pain and in what locations, how long have you had it, (3) has anything unusual or noteworthy occurred since the last stimulation? etc.

Having received such preliminary information from the patient, the computer programs will perform instrument diagnostic tests and make the stimulator ready for the stimulation session. In general, the algorithm for setting the stimulator parameters will have been decided by the physician and will include the extent to which the stimulator batteries should be charged, which the vagus nerve should be stimulated (right or left), and the time that the patient should wait after the stimulation session is ended until initiation of a subsequent stimulation session. The computer will query the physician's computer to ascertain whether there have been any updates to the algorithm, and if not, will use the existing algorithm. The patient will also be advised of the stimulation session parameter values by the interface computer program, so as to know what to expect.

Once the base station has been used to charge the stimulator's batteries to the requisite charge, the computer program (or smartphone app) will indicate to the patient that the stimulator is ready for use. At that point, the patient would clean the electrode surfaces, and make any other preliminary adjustments to the hardware. The stimulation parameters for the session will be displayed, and any options that the patient is allowed to select may be made. Once the patient is ready to begin, he or she will press a "start" button on the touchscreen and may begin the vagus nerve stimulation.

Multiple methods may be used to test whether the patient is properly attempting to stimulate the vagus nerve (or another nerve or organ or muscle or bone) on the intended side of the neck (or another portion of a human body). For example, accelerometers and gyroscopes within the smartphone may be used to determine the position and orientation of the smartphone's touch screen relative to the patient's expected view of the screen, and a decision by the stimulator's computer program as to which hand is being used to hold the stimulator may be made by measuring capacitance on the outside of the stimulator body, which may distinguish fingers wrapped around the device versus the ball of a thumb [Raphael WIMMER and Sebastian Boring. HandSense: discriminating different ways of grasping and holding a tangible user interface. Proceedings of the 3rd International Conference on Tangible and Embedded Interaction, pp. 359-362. ACM New York, NY, 2009, the disclosure of which is incorporated herein by reference for all purposes as if copied and pasted herein]. Pressing of the electrodes against the skin will result in a resistance drop across the electrodes, which can initiate operation of the rear camera. A fluorescent image should appear on the smartphone screen only if the device is applied to the side of the neck in the vicinity of the fluorescent spots that had been applied as a tattoo earlier. If the totality of these data indicates to the computer program that the patient is attempting to stimulate the wrong vagus nerve or that the device is being held improperly, the stimulation will be withheld, and the stimulator may then communicate with the patient via the interface computer program (in the mobile phone or laptop computer) to alert the patient of that fact. T Before logging off of the interface computer program, the patient may also review database records and summaries about all previous treatment sessions, so as to make his or her own judgment about treatment progress. If the stimulation was part of a prophylactic treatment regimen that was prescribed by the patient's physician, the patient interface computer program will remind the patient about the schedule for the upcoming self-treatment sessions and allow for a rescheduling if necessary.

For some patients, the stimulation may be performed for as little as 60 seconds, but it may also be for up to 30 minutes or longer. The treatment is generally performed once or twice daily or several times a week, for 12 weeks or longer before a decision is made as to whether to continue the treatment. For patients experiencing intermittent symptoms, the treatment may be performed only when the patient is symptomatic. However, it is understood that parameters of the stimulation protocol may be varied in response to heterogeneity in the pathophysiology of patients. Different stimulation parameters may also be used as the course of the patient's condition changes.

In some embodiments, various methods can use vagal nerve stimulation to suppress inflammation, thereby increasing the effectiveness of telomerase to maintain telomere lengths in cellular DNA. In some embodiments, some methods and devices involve the inhibition of pro-inflammatory cytokines, or more specifically, stimulation of the vagus nerve to inhibit and/or block the release of such pro-inflammatory cytokines. In some embodiments, some methods and devices use vagal nerve stimulation to increase the concentration or effectiveness of anti-inflammatory cytokines. TRACEY et al do not consider the modulation of anti-inflammatory cytokines to be part of the cholinergic anti-inflammatory pathway that their method of vagal nerve stimulation is intended to activate. Thus, they explain that "activation of vagus nerve cholinergic signaling inhibits TNF (tumor necrosis factor) and other proinflammatory cytokine overproduction through 'immune' a7 nicotinic receptor-mediated mechanisms" [V. A. PAVLOV and K. J. Tracey. Controlling inflammation: the cholinergic anti-inflammatory pathway. Biochemical Society Transactions 34, (2006, 6): 1037-1040, the disclosure of which is incorporated herein by reference for all purposes as if copied and pasted herein]. In contrast, anti-inflammatory cytokines are said to be part of a different "diffusible anti-inflammatory network, which includes glucocorticoids, anti-inflammatory cytokines, and other humoral mediators" [CZURA C J, Tracey K J. Autonomic neural regulation of immunity. J Intern Med. 257 (2005, 2): 156-66, the disclosure of which is incorporated herein by reference for all purposes as if copied and pasted herein]. Others make a similar distinction between vagal and humoral mediation [GUYON A, Massa F, Rovére C, Nahon J L. How cytokines can influence the brain: a role for chemokines? J Neuroimmunol 2008; 198: 46-55, the disclosure of which is incorporated herein by reference for all purposes as if copied and pasted herein].

The disclaiming by TRACEY and colleagues of a role for anti-inflammatory cytokines as mediators of inflammation following stimulation of the vagus nerve may be due to a recognition that anti-inflammatory cytokines (e.g., TGF-ß) are usually produced constitutively, while pro-inflammatory cytokines (e.g., TNF-alpha) are not produced constitutively, but are instead induced. However, anti-inflammatory cytokines are inducible as well as constitutive, so that for example, an increase in the concentrations of potentially anti-inflammatory cytokines such as transforming growth factor-beta (TGF-ß) can in fact be accomplished through stimulation of the vagus nerve [R A BAUMGARTNER, V A Deramo and M A Beaven. Constitutive and inducible mechanisms for synthesis and release of cytokines in immune cell lines. The Journal of Immunology 157 (1996, 9): 4087-4093, the disclosure of which is incorporated herein by reference for all purposes as if copied and pasted herein; CORCORAN, Ciaran; Connor, Thomas J; O'Keane, Veronica; Garland, Malcolm R. The effects of vagus nerve stimulation on pro- and anti-inflammatory cytokines in humans: a preliminary report. Neuroimmunomodulation 12 (5, 2005): 307-309, the disclosure of which is incorporated herein by reference for all purposes as if copied and pasted herein].

An example of a pro-anti-inflammatory mechanism that is particularly relevant to the treatment of multiple sclerosis is as follows. TGF-ß converts undifferentiated T cells into regulatory T (Treg) cells that block the autoimmunity that causes demyelination in multiple sclerosis. However, in the presence of interleukin-6, TGF-ß also causes the differentiation of T lymphocytes into proinflammatory IL-17 cytokine-producing T helper 17 (TH17) cells, which promote autoimmunity and inflammation. Thus, it is conceivable that an increase of TGF-ß levels might actually cause or exacerbate inflammation, rather than suppress it. Accordingly, a step in an embodiment of the methods that are disclosed herein is to deter TGF-ß from realizing its pro-inflammatory potential, by selecting nerve stimulation parameters that bias the potential of TGF-ß towards anti-inflammation, and/or by treating the patient with an agent such as the vitamin A metabolite retinoic acid that is known to promote such an anti-inflammatory bias [MUCIDA D, Park Y, Kim G, Turovskaya O, Scott I, Kronenberg M, Cheroutre H. Reciprocal TH17 and regulatory T cell differentiation mediated by retinoic acid. Science 317 (2007, 5835): 256-60, the disclosure of which is incorporated herein by reference for all purposes as if copied and pasted herein; Sheng XIAO, Hulin Jin, Thomas Korn, Sue M. Liu, Mohamed Oukka, Bing Lim, and Vijay K. Kuchroo. Retinoic acid increases Foxp3+ regulatory T cells and inhibits development of Th17 cells by enhancing TGF-ß-driven Smad3 signaling and inhibiting IL-6 and IL-23 receptor expression. J Immunol. 181 (2008, 4): 2277-2284, the disclosure of which is incorporated herein by reference for all purposes as if copied and pasted herein]. Retinoic acid is a member of a class of compounds known as retinoids, comprising three generations: (1) retinol, retinal, retinoic acid (tretinoin, Retin-A), isotretinoin and alitretinoin; (2) etretinate and acitretin; (3) tazarotene, bexarotene and Adapalene.

In some embodiments, endogenous retinoic acid that is released by neurons themselves is used to produce the anti-inflammatory bias. Thus, vagal nerve stimulation may induce differentiation through release of retinoic acid that is produced in neurons from retinaldehyde by retinaldehyde dehydrogenases, and some embodiments disclosed herein can promote anti-inflammatory regulatory T cell (Treg) differentiation by this type of mechanism [van de PAVERT S A, Olivier B J, Goverse G, Vondenhoff M F, Greuter M, Beke P, Kusser K, Höpken U E, Lipp M, Niederreither K, Blomhoff R, Sitnik K, Agace W W, Randall T D, de Jonge W J, Mebius R E. Chemokine CXCL13 is essential for lymph node initiation and is induced by retinoic acid and neuronal stimulation. Nat Immunol. 10 (11, 2009): 1193-1199, the disclosure of which is incorporated herein by reference for all purposes as if copied and pasted herein].

The retinoic acid so released might also directly inhibit the release or functioning of proinflammatory cytokines, which would be an anti-pro-inflammatory mechanism that is distinct from the one proposed by TRACEY and colleagues [Malcolm Maden. Retinoic acid in the development, regeneration and maintenance of the nervous system. Nature Reviews Neuroscience 8 (2007), 755-765, the disclosure of which is incorporated herein by reference for all purposes as if copied and pasted herein]. However, if the proinflammatory cytokine that is blocked is TNF-alpha, its inhibition in multiple sclerosis patients might be counterproductive. This is because blocking TNF-alpha with the drug lenercept promotes and exacerbates multiple sclerosis attacks rather than delaying them, which might be attributable to the fact that TNF-alpha promotes remyelination and the proliferation of oligodendrocytes that perform the myelination. [ANONYMOUS. TNF neutralization in MS: Results of a randomized, placebo controlled multicenter study. Neurology 1999, 53:457, the disclosure of which is incorporated herein by reference for all purposes as if copied and pasted herein; ARNETT H A, Mason J, Marino M, Suzuki K, Matsushima G K, Ting J P. TNF alpha promotes proliferation of oligodendrocyte progenitors and remyelination. Nat Neurosci 2001, 4:1116-1122, the disclosure of which is incorporated herein by reference for all purposes as if copied and pasted herein].

In this example, the competence of anti-inflammatory cytokines may be modulated by the retinoic acid (RA) signaling system of the nervous system. The most important mechanism of RA activity is the regulation of gene expression. This is accomplished by its binding to nuclear retinoid receptors that are ligand-activated transcription factors. Thus, RA acts as a transcriptional activator for a large number of other, downstream regulatory molecules, including enzymes, transcription factors, cytokines, and cytokine receptors. Retinoic acid is an essential morphogen in vertebrate development and participates in tissue regeneration in the adult [Jorg M E Y and Peter MdCaffery. Retinoic Acid Signaling in the Nervous System of Adult Vertebrates. The Neuroscientist 10 (5, 2004): 409-421, the disclosure of which is incorporated herein by reference for all purposes as if copied and pasted herein]. RA also increases synaptic strength in a homeostatic response (synaptic scaling) to neuronal inactivity through a mechanism involving protein synthesis that requires the participation of TNF-alpha. RA is also intimately involved in the control of the rhythmic electrical activity of the brain. More generally, all-trans retinoic acid, 9-cis retinoic acid, and 13-cis retinoic acid are some of a very small number of entrainment factors that regulate the natural rhythmicity of metabolic processes in many types of individual cells [Mehdi Tafti, Norbert B. Ghyselinck. Functional Implication of the Vitamin A Signaling Pathway in the Brain. Arch Neurol. 64 (12,2007): 1706-1711, the disclosure of which is incorporated herein by reference for all purposes as if copied and pasted herein].

The potentially anti-inflammatory cytokine TGF-beta is a member of the TGF-beta superfamily of neurotrophic factors. Neurotrophic factors serve as growth factors for the development, maintenance, repair, and survival of specific neuronal populations, acting via retrograde signaling from target neurons by paracrine and autocrine mechanisms. Other neurotrophic factors also promote the survival of neurons during neurodegeneration. These include members of the nerve growth factor (NGF) superfamily, the glial-cell-line-derived neurotrophic factor (GDNF) family, the neurokine superfamily, and non-neuronal growth factors such as the insulin-like growth factors (IGF) family. However, major problems in using such neurotrophic factors for therapy are their inability to cross the blood-brain-barrier, adverse effects resulting from binding to the receptor in other organs of the body and their low diffusion rate [Yossef S. Levy, Yossi Gilgun-Sherki, Eldad Melamed and Daniel Offen. Therapeutic Potential of Neurotrophic Factors in Neurodegenerative Diseases. Biodrugs 2005; 19 (2): 97-127, the disclosure of which is incorporated herein by reference for all purposes as if copied and pasted herein].

Figure 10:
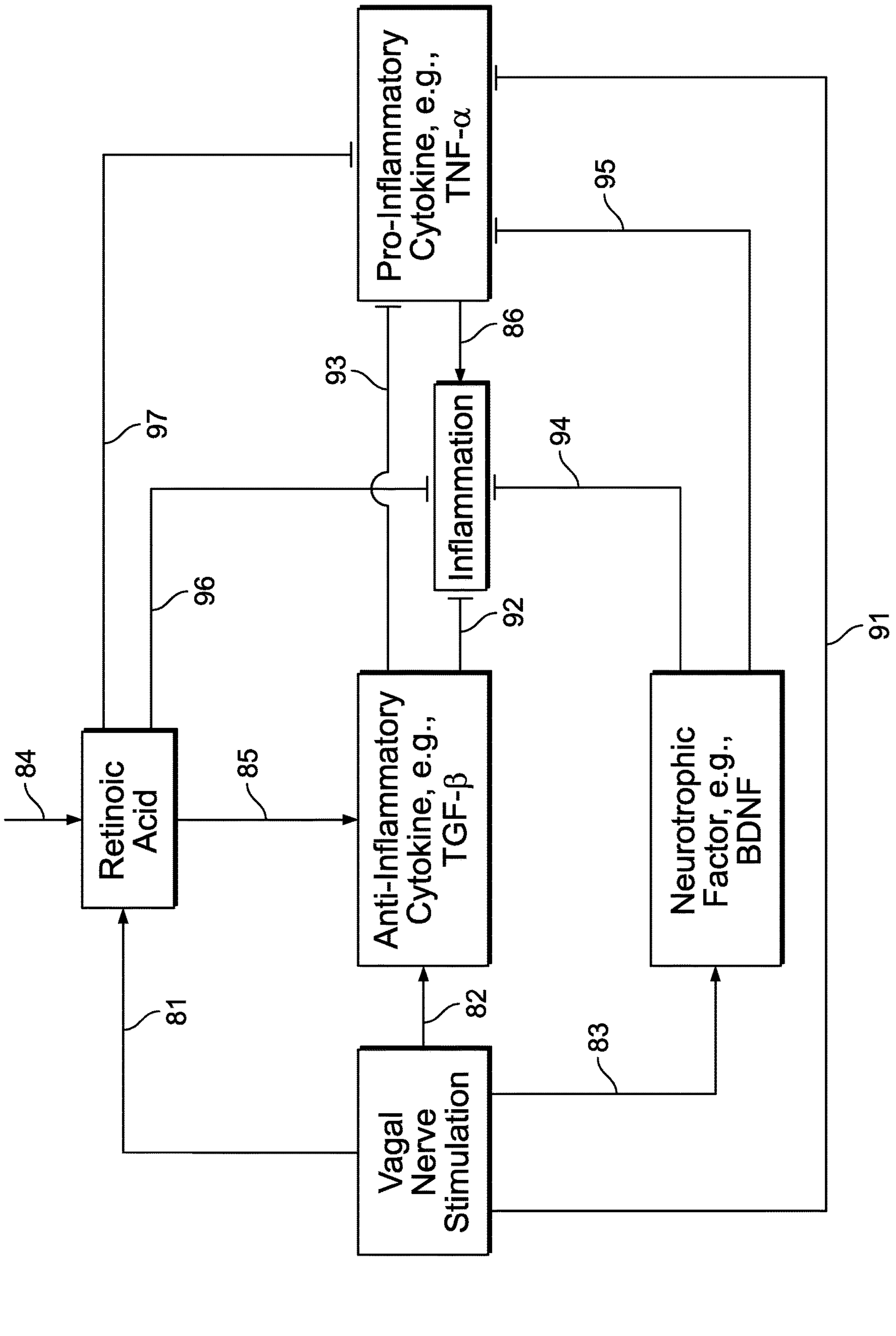
FIG. 10 illustrates an embodiment of mechanisms or pathways through which stimulation of the vagus nerve may reduce inflammation in patients with neurodegenerative or autoimmune disorders according to this disclosure.

FIG. 10 illustrates mechanisms or pathways through which stimulation of the vagus nerve may be used to reduce inflammation in patients. In what follows, it is understood that not all of the pathways or mechanisms may be used in the treatment of a particular patient and that pathways or mechanisms that are not shown in FIG. 10 may also be used. Thus, particular pathways or mechanisms are invoked by the selection of particular stimulation parameters, such as current, frequency, pulse width, duty cycle, etc. Nevertheless, as an aid to understanding the applications that follow, it is useful to consider at once all the mechanisms shown in FIG. 10.

Two types of pathways are shown in FIG. 10. The pathways that stimulate or upregulate are indicated with an arrow ( ) The pathways that inhibit or downregulate are indicated with a blockage bar ( ) Pathways resulting from stimulation of the vagus nerve are shown to stimulate retinoic acid 81, anti-inflammatory cytokines 82 such as TGF-beta, and neurotrophic factors 83 such as BDNF. The patient may also be treated with retinoic acid or some other retinoid by administering it as a drug 84. For cytokines that may have both anti-inflammatory and pro-inflammatory capabilities, the retinoic acid biases such cytokines to exhibit their anti-inflammatory potential, as shown in the pathway labeled as 85. Pro-inflammatory cytokines, on the other hand, promote inflammation by pathways labeled as 86. Stimulation of the vagus nerve inhibits the release of pro-inflammatory cytokines 91 directly through pathways that have been described by TRACEY and colleagues. The other pathways shown in FIG. 8 to inhibit inflammation following stimulation of the vagus nerve are novel to this disclosure, and include inhibition of inflammation via anti-inflammatory cytokine pathways 92 including those that inhibit the release of pro-inflammatory cytokines 93, inhibition via neurotrophic factors 94 including those that inhibit the release of pro-inflammatory cytokines 95, and inhibition via retinoic acid pathways 96 including those that inhibit the release of pro-inflammatory cytokines 97.

It is understood that the labels in FIG. 10 that are used for simplicity to describe the pathways actually refer to a large set of related pathways. For example, the box labeled as "retinoic acid" actually refers to not only retinoic acid but also to a larger class of retinoids, as well as to retinaldehyde dehydrogenases, retinoic acid receptors (RAR), retinoid X receptors (RXR), retinoic acid response elements (RAREs), and more generally to the retinoic acid signaling system of the nervous system and related pathways.

Furthermore, it is understood that the box labeled "Anti-Inflammatory Cytokine, e.g., TGF-beta" can actually be placed within the box entitled "Neurotrophic Factor", because TFG-beta is a member of the superfamily of TGF-beta neurotrophic factors [Yossef S. Levy, Yossi Gilgun-Sherki, Eldad Melamed and Daniel Offen. Therapeutic Potential of Neurotrophic Factors in Neurodegenerative Diseases. Biodrugs 2005; 19 (2): 97-127, the disclosure of which is incorporated herein by reference for all purposes as if copied and pasted herein]. However, because TGF-beta is ordinarily referred to simply as a cytokine, and because its anti-inflammatory competence is known to be influenced by retinoic acid, it was placed in a separate box to avoid undue confusion.

The role of the sympathetic nervous system (SNS) in the regulation of the immune system has been long appreciated through the activity of the hypothalamic pituitary-adrenal axis (HPA) and through which corticosteroids (cortisol) and other naturally occurring immunosuppressive compounds are released (Rook, 1999). In parallel with this understanding, beginning in the 1930s and 1940s, it was observed that a splenectomy could provide relief from severe inflammatory conditions such as Rheumatoid arthritis (Bach, 1946). It was a natural extension of these two lines of thinking, therefore, to attempt to modulate the splenic nerve (an element of the SNS) and identify how the immune system was impacted. The effects of stimulating these neural inputs to the spleen began to be reported as early as the 1960s (Davies et al., 1968) (FIG. 132.1).

Besedovsky et al. (1979) described the SNS as playing an important role in a feedback loop that coupled lymphoid organ activity to the CNS. In this model, the efferent arm of the SNS projects to immune system organs, releasing NE from sympathetic nerve terminals in these organs (Elenkov et al., 2000). The role of NE in modulating macrophages and other immune cells in an anti-inflammatory direction has been well established (Hu et al., 1991). Both endogenous, tonic expression, and volume transmission through extra synaptic means, i.e., varicosities, have been proposed as a means for maintaining a baseline level of suppression over immune activity (Straub et al., 1998). With respect to the afferent arm of this feedback loop, it has been suggested that peripheral cytokine levels are able to modulate the CNS to alter sympathetic outflow. In fact, two separate groups reported, in 1989 and 1991, that infusion of IL-1! or IFN-" into the ventricles of the brain causes rapid, significant reductions in peripheral and splenic immune cell activity (Sunder et al., 1989; Brown et al., 1991). To facilitate this activation within the CNS, afferent vagal fibers were proposed as a functional pathway for peripheral cytokine modulation of the CNS (Maier et al., 1998).

Further evidence of VN involvement with splenic immune function came when Bernik et al. (2001) studied the significant peripheral, anti-inflammatory effects of semapimod (a compound formerly known as CNI-1493), which, at one point, was believed to inhibit inflammation through inhibition of p38 MAP kinase. Minute quantities of semapimod, were administered intracerebral-ventricular (ICV), just as IL-1 # and IFN-$ had been used previously. However, unlike the prior thesis of sympathetic pathway involvement, Bernik et al. reversed the assumption of efferent signaling from sympathetic to the parasympathetic (vagus), when it was found that severing of the VN abolished the anti-inflammatory effects. Their conclusion was that semapimod was a potent activator of efferent, vagal outflow (Oke et al., 2007). Borovikova et al. (2000) had previously demonstrated that electrical stimulation of the distal remains of the severed VN, i.e., the efferent vagal component, was able to trigger anti-inflammatory effects, even in the absence of ICV administration of semapimod, IL-1 #, or IFN-$. (As will be discussed later, additional studies showed that electrical stimulation of the afferent arms, post vagotomy, were also able to affect the same immune modulation.)

A review of the available literature on this subject strongly suggests that there is broad, albeit not universal, agreement that stimulation of the VN (using appropriate stimulation, signal parameters) generates a splenic nerve-mediated, anti-inflammatory effect. Initial proposals to explain the pathway suggest a simple efferent model that is based solely on acetylcholine release (the primary neurotransmitter released by efferent vagal fibers), whereby direct release of acetylcholine and binding to receptors on macrophages suppresses the production of inflammatory cytokines. The specific, efferent pathway was hypothesized to be through a binding of acetylcholine to the $7-nicotinic, acetylcholine receptor ($7nAChR), since the anti-inflammatory effect of efferent (post vagotomy) stimulation was lost in $7nAChR knockout animals (de Jonge et al., 2007).

Figure 11:
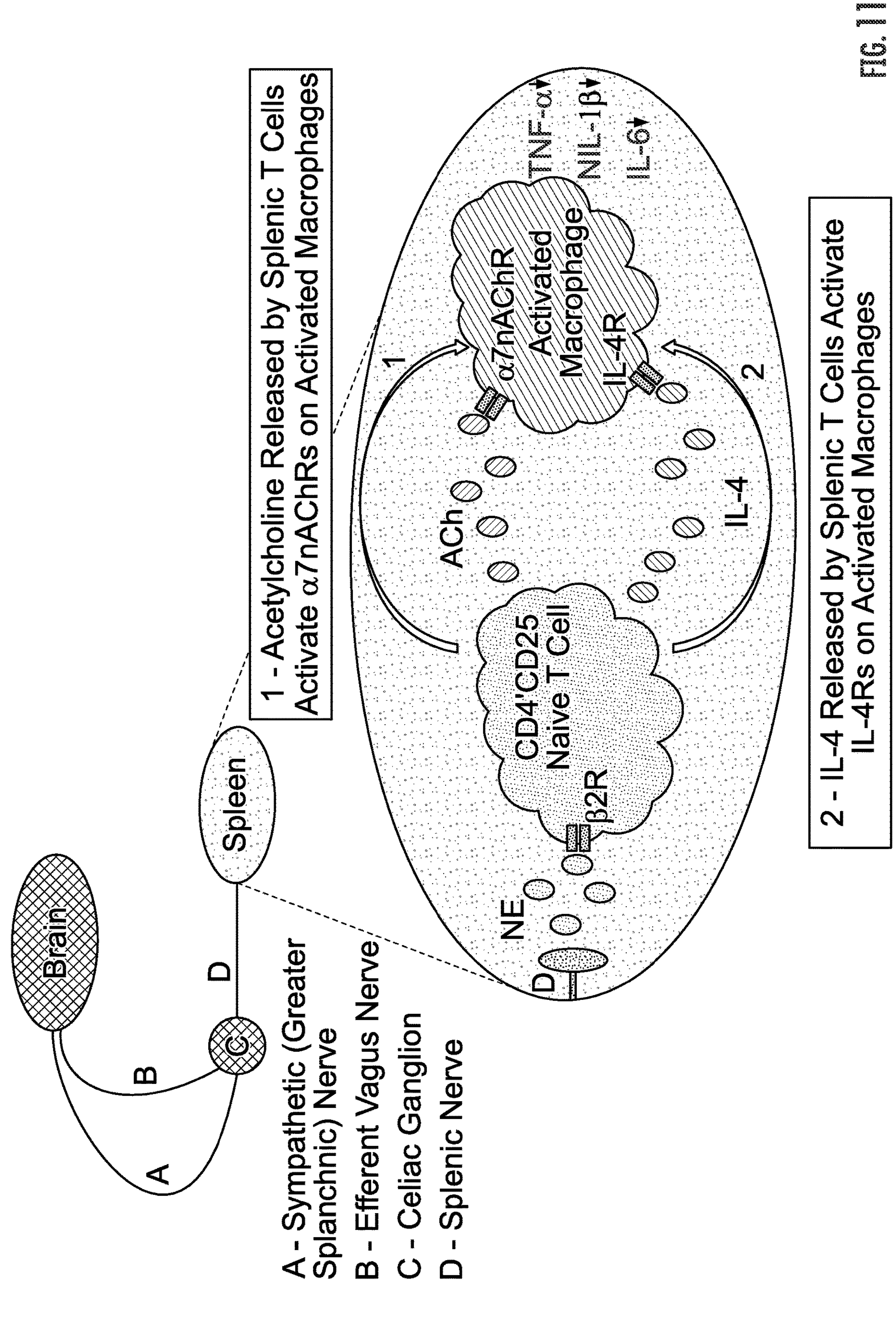
FIG. 11 illustrates an embodiment of another mechanism of action of a medical device in which sympathetic fibers release norepinephrine into a spleen in close proximity to a specialized group of immune cells that release acetylcholine, or ACh according to this disclosure.

In some embodiments, the systemic anti-inflammatory effects of VNS are believed to result from the activation of sympathetic fibers in the splenic nerve, through a connection at the celiac ganglion. These sympathetic fibers release norepinephrine into the spleen in close proximity to a specialized group of immune cells that release acetylcholine, or ACh. This release of ACh activates a receptor, the alpha 7 nicotinic ACh receptor, or 7nAChR, on cytokine-releasing immune cells called macrophages. Activation of these receptors is believed to function by blocking transcription factors that promote inflammatory cytokine expression. Based on the role of ACh in activating this pathway, which is shown in FIG. 11 below, it has been termed the cholinergic anti-inflammatory pathway, or CAP.

Stimulation of the Vagus Nerve to Treat Conditions

Example 1

Systems of the Present Disclosure

Figure 12:
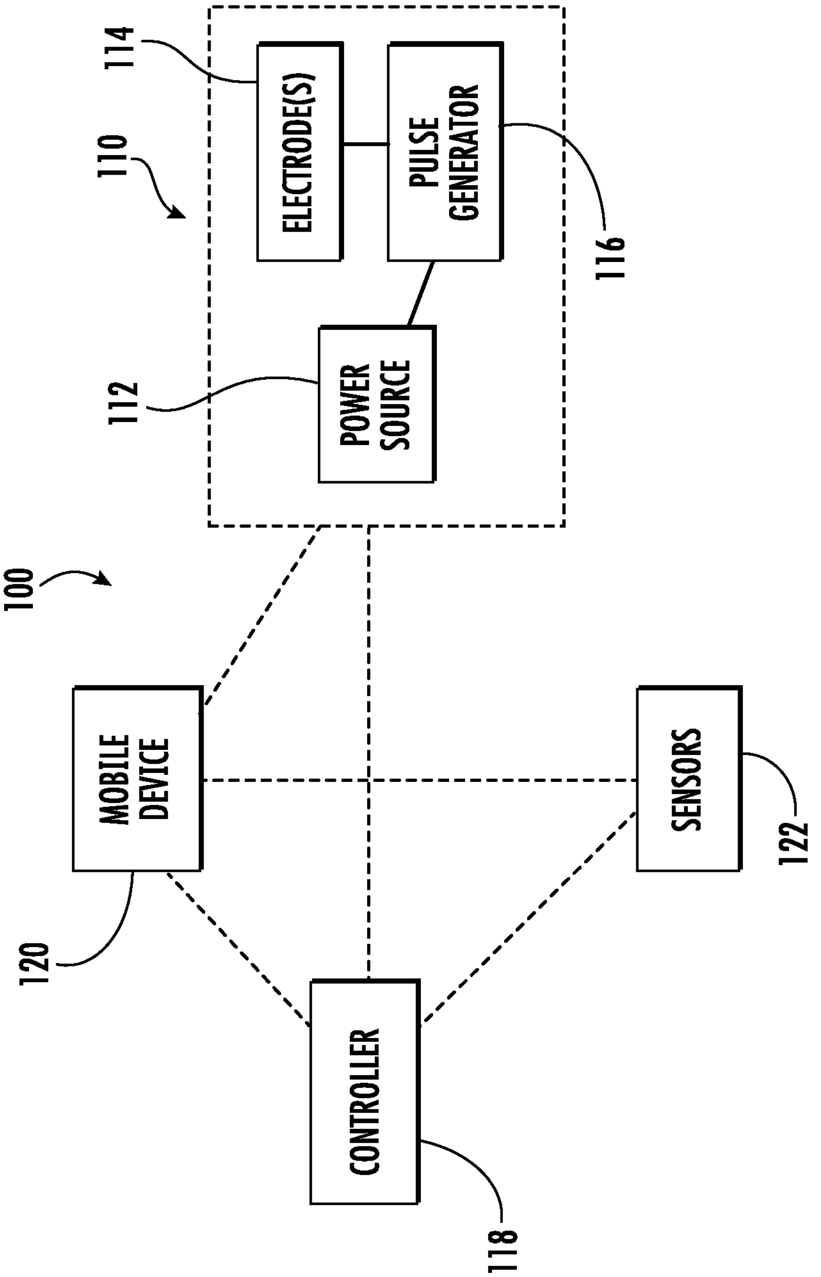
FIG. 12 illustrates a system for modulating the vagus nerve according to the present disclosure.

Referring now to FIG. 12, a system 100 for stimulating a nerve in a patient, such as the vagus nerve, according to the present disclosure will not be described is a control theory representation of the disclosed vagus nerve stimulation methods. As shown, system 100 includes a stimulator 210, which may include one or more electrodes 114, a pulse generator 116 and an energy source 112. Electrodes 114, pulse generator 116 and energy source 112 may all be housed in a single housing, as described in detail above. In an alternative embodiment, electrodes 114 are disposed separately from energy source 112 and pulse generator 116. Electrodes 114 may be coupled to these components via wired connections or wirelessly. In the latter configuration, electrodes 114 may include suitable electronic components coupled thereto to receive the electrical impulse(s) from pulse generator 116 and to apply those electrical impulse(s) through electrodes 114 to the patient. Such electronic components may include, for example, a wireless receiver or similar component that receives the signal from a wireless transmitter coupled to pulse generator 116.

In still another embodiment, pulse generator 116 and energy source 112 are coupled to each other, either wirelessly, via wired connections, or directly in a housing that contains both components. This housing may, for example, include a wireless transmitter and may be worn by the patient in manners known to those skilled in the art, so that the signal can be transmitted from the housing to electrodes 114.

System 100 further includes a controller 118 that is coupled to stimulator 210 and may be used to select or set parameters for the stimulation protocol (amplitude, frequency, pulse width, burst number, electrode positioning etc.), the treatment regimen discussed above (i.e., duration and number of doses, etc.) or alert the patient as to the need to use or adjust the stimulator (i.e., an alarm). Controller 118 may be directly coupled to stimulator 210 via wired connectors or within the same housing, or it may be wirelessly coupled to stimulator 210.

Significant portions of the control of the vagus nerve stimulation may reside in controller components that are physically separate from stimulator 210. In this embodiment, separate components of the controller 118 and stimulator 210 generally communicate with one another wirelessly. Thus, the use of wireless technology avoids the inconvenience and distance limitations of interconnecting cables.

In certain embodiments, system 100 may further include a mobile device 120 that either couples controller 118 to stimulator 210 or vice versa. Mobile device 120 may comprise a mobile phone, such as a smartphone, a smartwatch, iPad, laptop computer or any other mobile device having a computing function and wireless transmission technology.

System 100 may further include one or more sensors 122 used for detecting certain physiological parameters of the patient based on the stimulation of the nerve. The preferred sensors will include ones ordinarily used for ambulatory monitoring. For example, the sensors may comprise those used in conventional Holter and bedside monitoring applications, for monitoring heart rate and variability, ECG, respiration depth and rate, core temperature, hydration, blood pressure, brain function, oxygenation, skin impedance, and skin temperature. The sensors may be embedded in garments or placed in sports wristwatches, as currently used in programs that monitor the physiological status of soldiers [G. A. SHAW, A. M. Siegel, G. Zogbi, and T. P. Opar. Warfighter physiological and environmental monitoring: a study for the U.S. Army Research Institute in Environmental Medicine and the Soldier Systems Center. MIT Lincoln Laboratory, Lexington Mass. Nov. 1, 2004, pp. 1-141]. The ECG sensors should be adapted to the automatic extraction and analysis of particular features of the ECG, for example, indices of P-wave morphology, as well as heart rate variability indices of parasympathetic and sympathetic tone. Measurement of respiration using noninvasive inductive plethysmography, mercury in silastic strain gauges or impedance pneumography is particularly advised, in order to account for the effects of respiration on the heart. A noninvasive accelerometer may also be included among the ambulatory sensors, in order to identify motion artifacts. An event marker may also be included in order for the patient to mark relevant circumstances and sensations.

For brain monitoring, the sensors may comprise ambulatory EEG sensors [CASSON A, Yates D, Smith S, Duncan J, Rodriguez-Villegas E. Wearable electroencephalography. What is it, why is it needed, and what does it entail? IEEE Eng Med Biol Mag. 29 (3,2010):44-56] or optical topography systems for mapping prefrontal cortex activation [Atsumori H, Kiguchi M, Obata A, Sato H, Katura T, Funane T, Maki A. Development of wearable optical topography system for mapping the prefrontal cortex activation. Rev Sci Instrum. 2009 April; 80(4):043704]. Signal processing methods, comprising not only the application of conventional linear filters to the raw EEG data, but also the nearly real-time extraction of non-linear signal features from the data, may be considered to be a part of the EEG monitoring [D. Puthankattil SUBHA, Paul K. Joseph, Rajendra Acharya U, and Choo Min Lim. EEG signal analysis: A survey. J Med Syst 34 (2010):195-212]. In the present application, the features would include EEG bands (e.g., delta, theta, alpha, beta).

For any given position of the stimulator relative to the vagus nerve, it is also possible to infer the amplitude of the electric field that it produces in the vicinity of the vagus nerve. This is done by calculation or by measuring the electric field that is produced by the stimulator as a function of depth and position within a phantom that simulates the relevant bodily tissue [Francis Marion MOORE. Electrical Stimulation for pain suppression: mathematical and physical models. Thesis, School of Engineering, Cornell University, 2007; Bartosz SAWICKI, Robert Szmurlo, Przemyslaw Plonecki, Jacek Starzynski, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. Thus, in order to compensate for movement, the controller may increase or decrease the amplitude of the output from the stimulator (u) in proportion to the inferred deviation of the amplitude of the electric field in the vicinity of the vagus nerve, relative to its desired value.

In some cases, it may be difficult, or impossible for patients to may reflect self-administer the device, such as immediately after surgery or, whilst the latter may reflect a lack of motivation once bowel function has returned.

Figure 13:
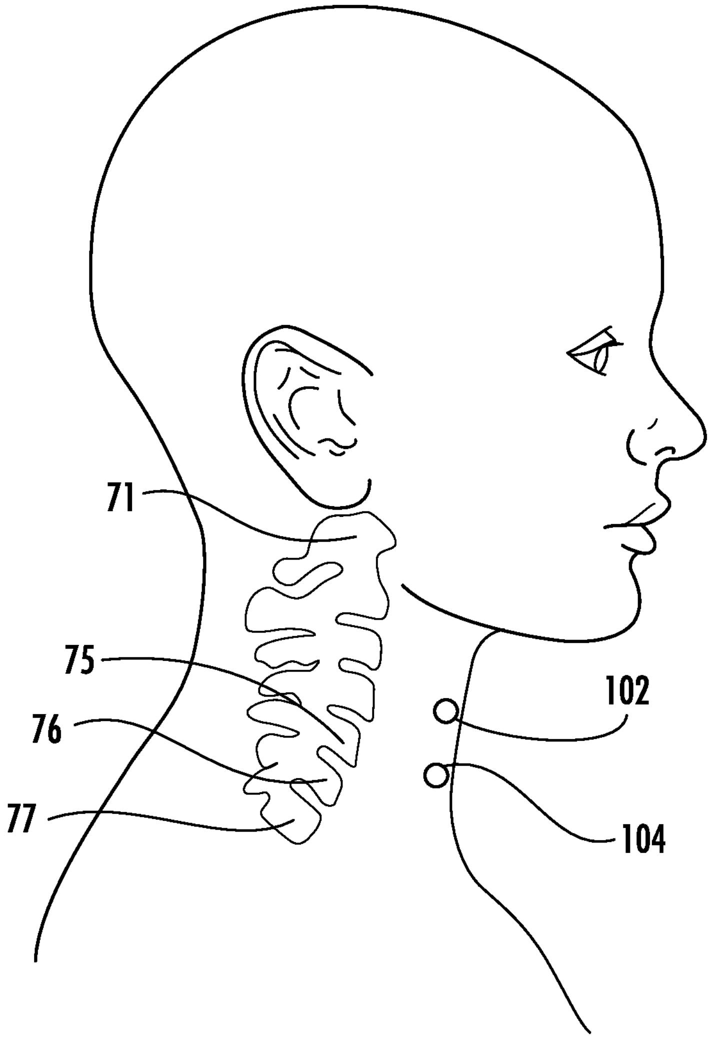
FIG. 13 illustrates another embodiment of the present disclosure, wherein first and second electrodes are positioned on an outer surface of the patient's neck.

Referring now to FIG. 13, another embodiment of the present disclosure includes first and second electrodes 102, 104 configured for attachment to an outer skin surface of the patient, such as the neck. Electrodes 102, 104 may include a suitable adhesive that secured them to a skin surface. Suitable adhesive electrodes for use with the present invention may include electrode pads, self-adhesive electrodes or the like. Electrodes 102, 104 may be coupled to pulse generator 116 and/or energy supply 112 via wires or wirelessly. In a preferred embodiment, electrodes 102, 104 will include a wireless receiver and suitable electronic components (not shown) for receiving a wireless signal from pulse generator 116 to apply an electrical impulse through the outer skin surface of the patient.

In this embodiment, electrodes 102, 104 may be placed in a suitable location on the patient's neck and adhered thereto. Electrodes 102, 104 receive electrical impulses from pulse generator 116. The duration, amplitude, frequency and treatment paradigm for the electrical impulses may be controlled by controller 118, mobile device 120, or via another electronic device coupled to pulse generator 116. This embodiment allows, for example, a physician to secure electrodes 102, 104 to the patient's neck such that the treatment paradigm may be followed without patient involvement. This is particularly useful for treating patients that are unable or unwilling to self-treat. For example, in some cases, patients recovering from surgery, such as major colorectal surgery may be either incapable of self-treatment, or their compliance with the treatment protocol may not be complete. In another example, older patients may not have suitable mental faculties for self-treatment.

Figure 14A:
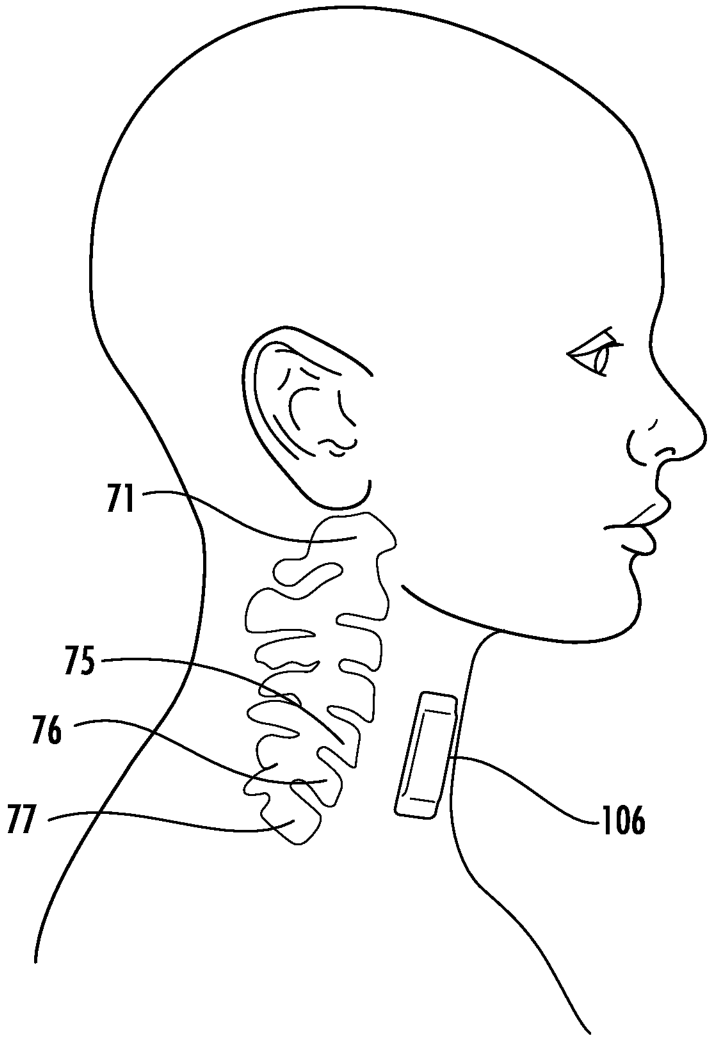
FIG. 14A illustrates yet another embodiment of the present disclosure, wherein a wearable device is positioned on an outer surface of the patient's neck.

Referring now to FIG. 14A, another embodiment of the present invention comprises a stimulator (not shown) that may be secured to the outer skin surface of the patient's neck. Stimulator may be housed in an outer covering or patch 106 to protect stimulator from the environment. The patch 106 may include a suitable adhesive strip or pad on one surface for adhering the patch 106 and stimulator to the outer skin surface of the patient.

The stimulator in this embodiment includes one or more electrodes. The stimulator may also include a power source such as a battery, and a signal generator for applying the electrical impulses to the electrodes. Alternatively, the power source and/or the signal generator may be wirelessly coupled to the electrodes, as discussed above. An external controller may be wirelessly coupled to the stimulator to provide a stimulation protocol to the signal generator and to control other key functions of the signal, such as power, amplitude, duration frequency and the like.

The stimulator may reside in a housing that is removably coupled to the patch via a snap-fitting, Velcro, or other suitable attachment means. In this embodiment, the patch may be adhered to the patient and the stimulator may be removed and reattached without removing the patch. This allows the healthcare professions to, for example, recharge the battery, troubleshoot the device and/or control the stimulation therapy on the device.

The stimulator may also include a conductive fluid, such as a gel pad, disposed between the electrode(s) and the patient's outer skin surface to enhance conductivity of the electrical impulses through the outer skin surface to the nerve.

Alternatively, outer covering 106 may comprise any wearable material that may include the stimulator. For example, depending on the location of the target nerve on the patient's body, the stimulator may be attached to, or embedded within, a wearable garment, such as a shirt, scarf, watch, hat, gloves, pants, shoes, boots, socks, underwear, belt, dress, jacket, sweater, ear muffs, or the like. The wearable garment may also comprise an accessory, such as a wristband, ankle or wrist bracelet, necklace, earrings, a compression garment, an ankle or knee brace or the like.

In yet another embodiment, the garment itself is the stimulator. For example, the garment may comprise an electronic textile or e-textile that includes fabrics that enable digital components, such as electrodes, pulse generators, batteries wireless receivers and other electronic components to be embedded therein. Electronic textiles are distinct from wearable garments because the emphasis is placed on the seamless integration of textiles with electronic elements like microcontrollers, sensors, and actuators. In one embodiment, the electronic textile may comprise an organic electronics material that is conducting and has insulated electrical components that allows the garment to be washed without damaging the electronic components.

The stimulator of this embodiment includes one or more electrodes for applying electrical impulses to a nerve within the patient, as discussed above. The electrodes may include a wireless receiver and suitable electronics to receive the electrical impulses from pulse generator 116. Alternatively, the stimulator may also include pulse generator 116 and/or energy supply 112. In this embodiment, the stimulator may be, for example, wireless coupled to controller 118, mobile device 120 or another suitable control device.

The stimulator may also include an array of electrodes. The electrode array may include multiple sets of electrodes with each set of electrodes configured to apply electrical impulses through the outer skin surface of the patient, as discussed above. Each of the sets of electrodes may be individually coupled to the pulse generator, either directly, through wires, or wireless as described above. The electrode array may have multiple patterns. For example, the array may be linear, square, circular or any other suitable shape.

In certain embodiments, the electrode array comprises two or more sets of electrodes, each spaced apart from each other between about 2 mm to about 25 mm, preferably between about 4 mm to about 10 mm. The electrode array preferably comprises a shape that substantially corresponds to a target area of the patient's neck. In one embodiment, the target area is the area on the neck that allows for electrical impulses to be passed through the skin to the vagus nerve (discussed in detail below).

The electrode sets may each be individually coupled to pulse generator 116 such that electrical impulses can be applied to all of the electrode sets, some of the electrode sets or only one of the electrode sets.

Figure 14B:
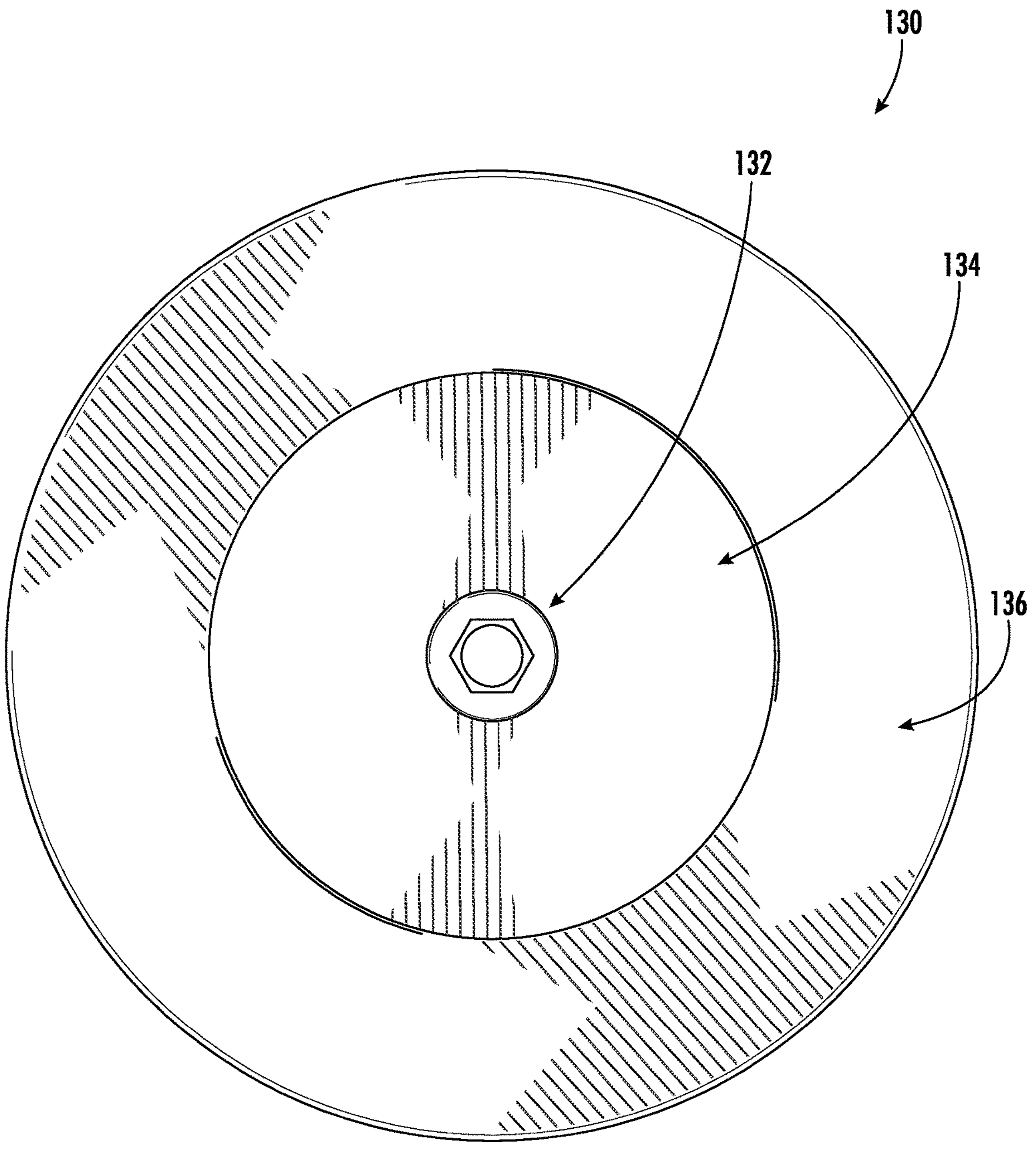
FIG. 14B illustrates a representative electrode of the embodiments of FIGS. 13 and 14A.
Figure 14C:
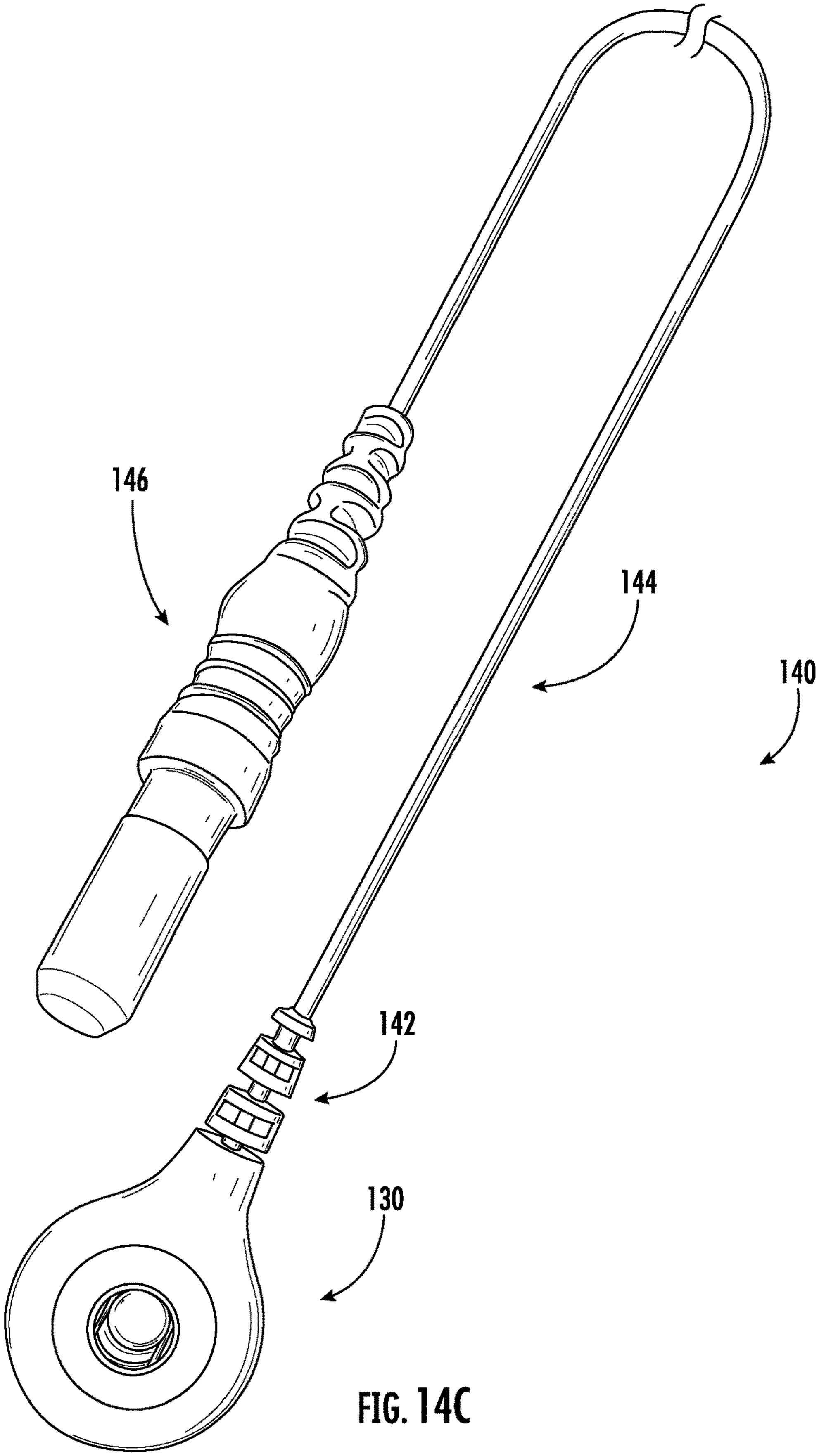
FIG. 14C illustrates a representative electrode and a representative lead of the embodiments of FIGS. 13 and 14A.

FIG. 14B illustrates a representative electrode 130 that includes an electrically conductive surface 132 for contacting the outer skin surface of the patient. Electrode 130 may further include an adhesive pad 136 for attaching electrode 130 to the outer skin surface, and an insulating material 134 for electrically isolating conductive surface 132.

FIG. 14B illustrates a representative electrode 130 and a representative lead 140 for use with one of the embodiments of the present disclosure. As shown, lead 140 may include a distal connector 142 for coupling to electrode 130, an insulated electrical wire or other connection 144 and a proximal connector 146 for coupling electrode 130 to a suitable power source and signal generator (now shown).

In this embodiment, the system may further include one or more sensors 122, such as those described above, for detecting whether the nerve has been stimulated, the amplitude of the stimulation, or whether the nerve has been stimulated with sufficient amplitude and other parameters to fire an action potential. The sensors may detect a physiological parameter of the patient. Alternatively, the sensors may be coupled to the electrodes and may sense one or more parameters of the electrodes, such as impedance, amplitude, voltage or the like.

The sensors may also be coupled to the controller 118. In this embodiment, the controller is configured to receive input from the sensors and to direct the pulse generator 116 to apply electrical impulses to one or more sets of the electrodes 114 based on this input. For example, the sensors may provide data that suggests that one or more of the sets of electrodes is not positioned properly to stimulate the nerve, or to stimulate the nerve at the optimal signal strength to cause the nerve to fire an action potential. The controller is configured to shift the electrical impulse to the set or sets of electrodes that provide a sufficient electrical impulse to the nerve to cause it to fire an action potential. In this manner, the controller can optimize the application of the electrical impulses to the nerve.

This embodiment is particularly useful for applying electrical impulses through an outer skin surface of a patient to a deeper nerve, such as the vagus nerve. The optimal positioning of the electrodes can be challenging in such an application. If the electrodes are placed incorrectly on the neck, the electrical signals may not pass through to the nerve, or they may only pass through at limited strength that is not sufficient to cause the nerve to fire an action potential. With this embodiment, an array of electrodes may be placed over a broader area of the outer skin surface. The controller may direct the pulse generator to selectively apply electrical impulses to each set of electrodes. The sensors will then provide feedback to the controller, as discussed above, and the controller will determine the optimal set or sets of electrodes in which to apply the electrical impulses.

Embodiments of Reusable Neurostimulators

Figure 15:
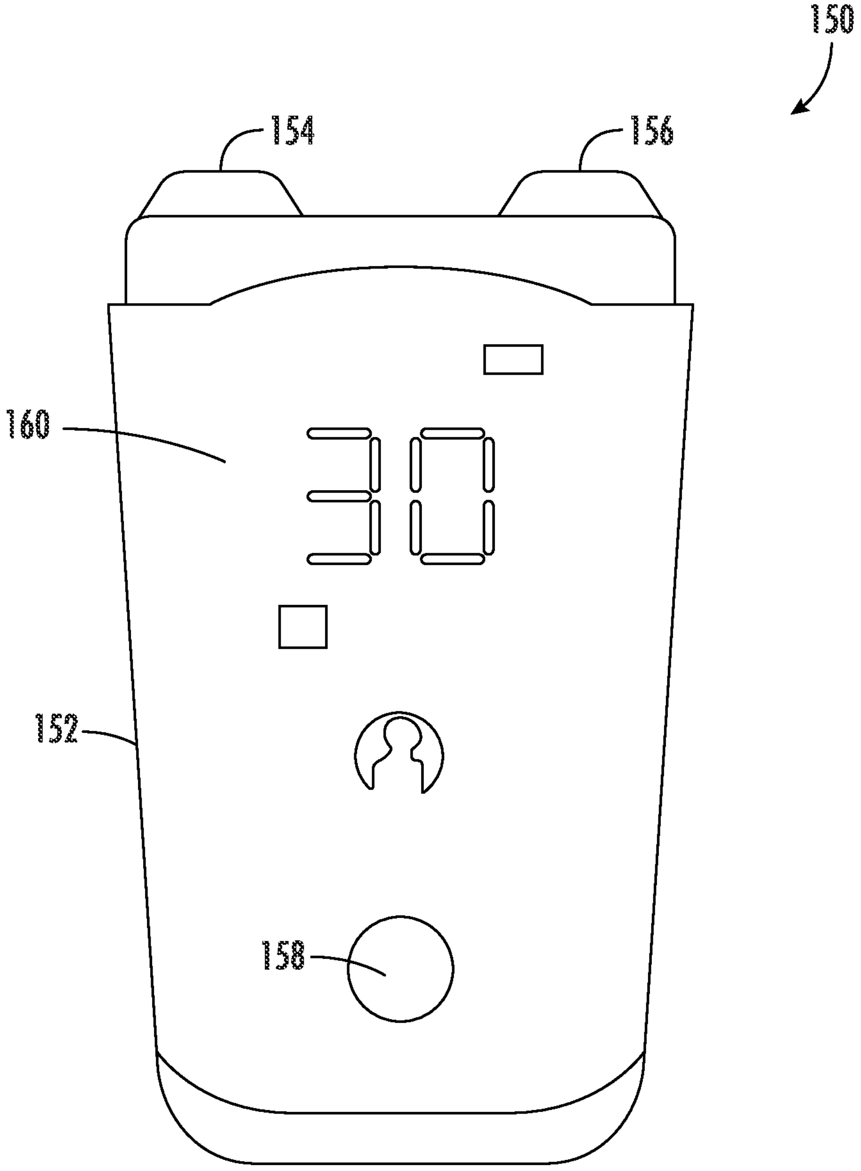
FIG. 15 illustrates another embodiment of a stimulator device according to the present disclosure.

Referring now to FIGS. 15 and 16A-16C, systems and methods for refilling neurostimulator devices, such as the ones portrayed above, will now be described. FIG. 15 illustrates another embodiment of a stimulator device 150 according to the present disclosure. Device 150 includes a housing 152 for housing the signal generator, energy source and other electronic components described above. Housing 152 includes first and second electrodes 154, 156 extending from an upper surface of housing 152. Housing 152 further includes a user input 158 that may, for example, include an energy control that turns the device On/Off and/or a signal control that causes the signal generator to transmit electrical impulses to the electrodes. Housing 152 may include additional user inputs, such as controls for amplitude level of the electrical impulses and the like. Housing further includes one or more user displays or icons 160 that provide information regarding the operation of the device. For example, user display 160 may illustrate the number of doses that the device has available, as discussed in more detail below. User display may include additional information, such as status of the device, a single indicator that alerts the patient that the electrodes are not properly positioned against an outer skin surface such that current may pass therethrough.

Device 150 may include an accompanying vibration and/or audible signal or buzzer in case the icons are not visible or when the patient is asleep or otherwise not able to view user interface 160. In this embodiment, inputs 158 may further comprise controls that turn ON/OFF the vibration or the audible signals (e.g., a mute button).

Figure 16A:
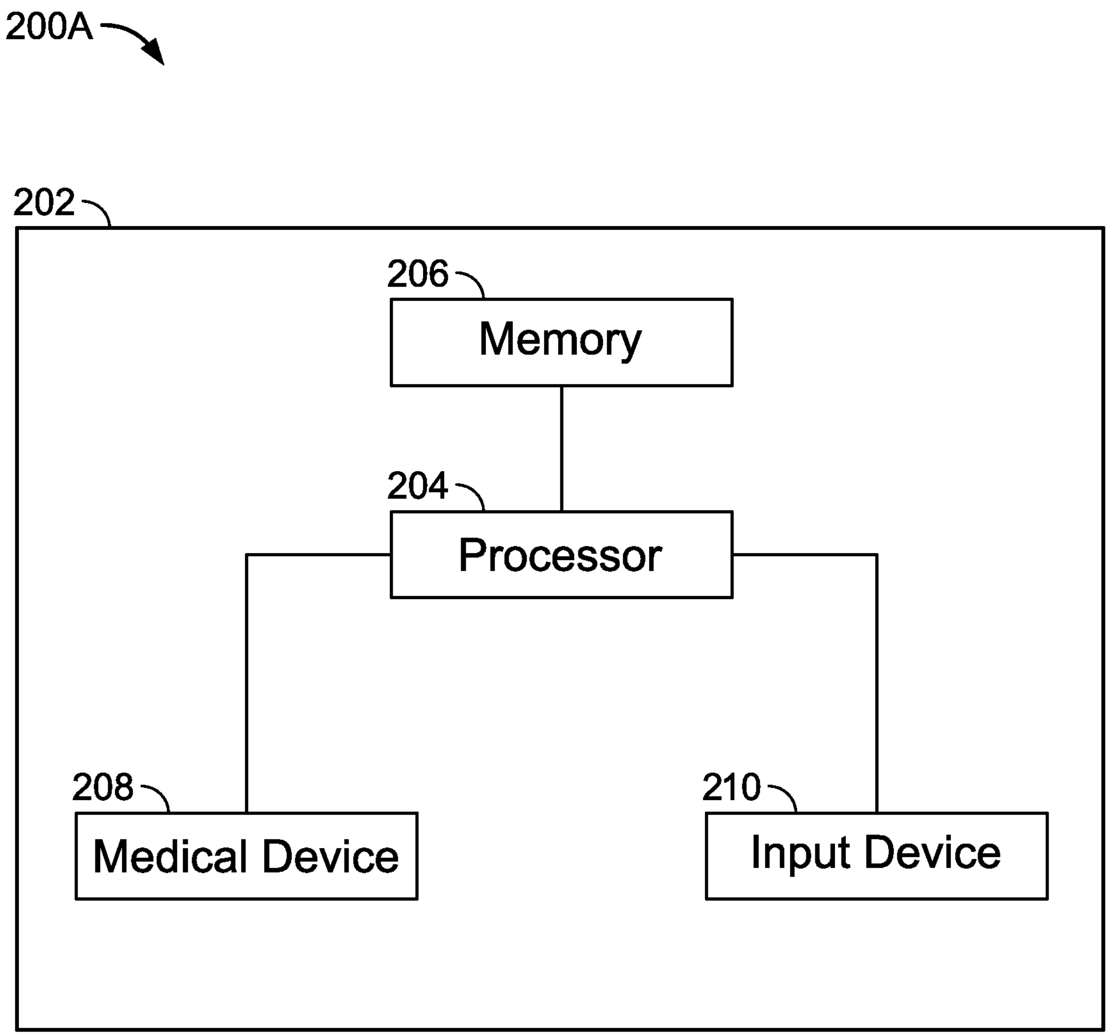
FIG. 16A is a schematic diagram of an embodiment of a system containing a medical device and an input device according to this disclosure.
Figure 16B:
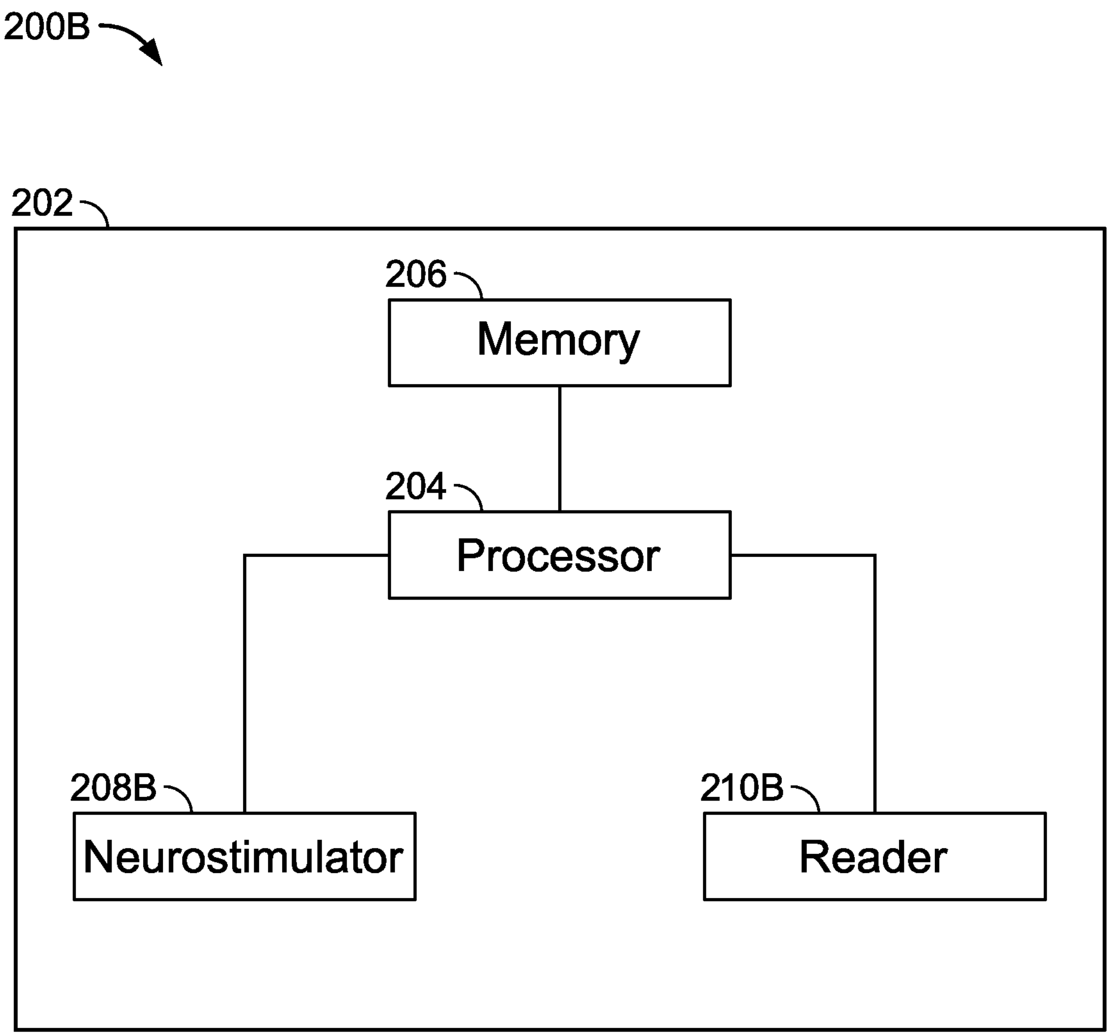
FIG. 16B is a schematic diagram of an embodiment of a system containing a neurostimulator and a reader according to this disclosure.
Figure 16C:
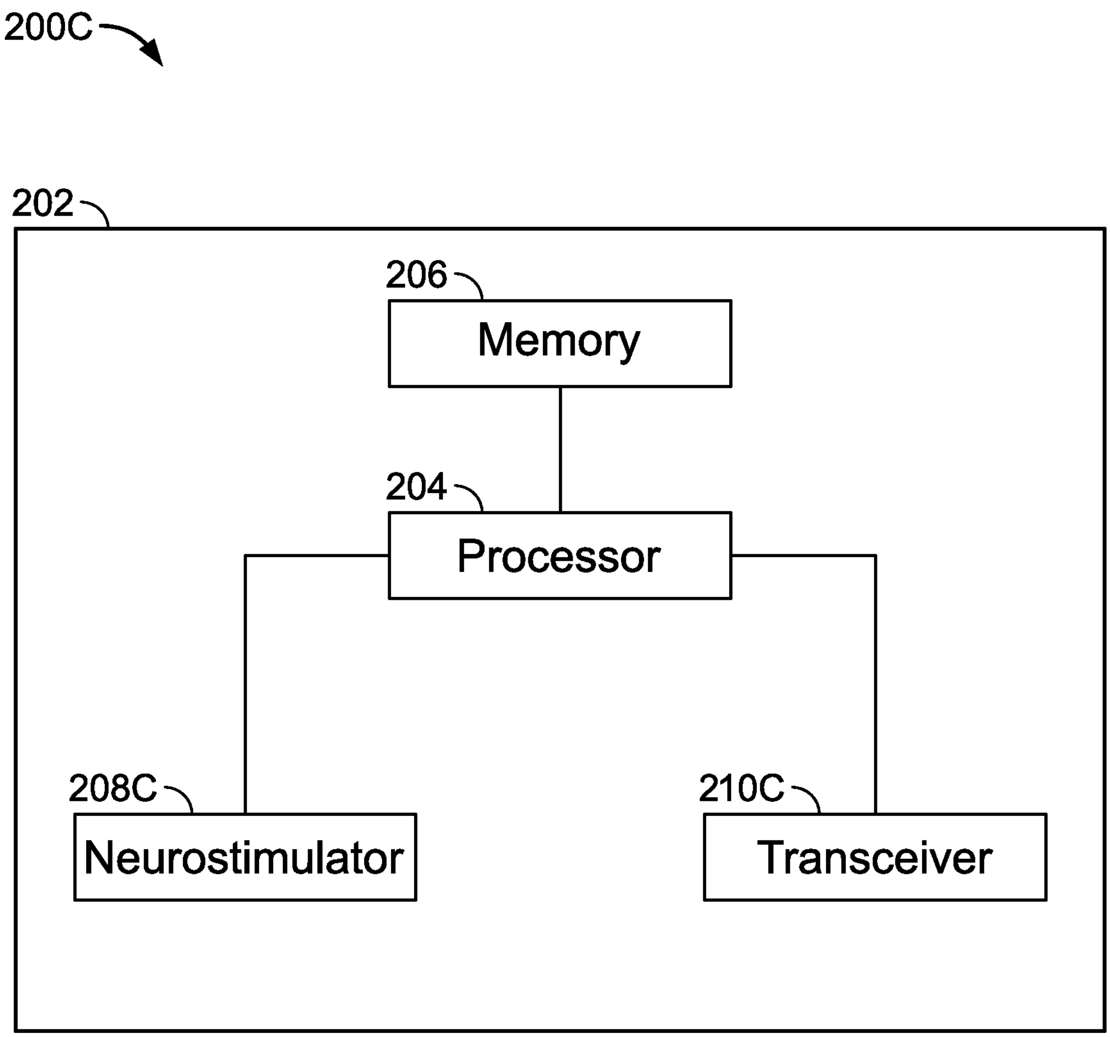
FIG. 16C is a schematic diagram of an embodiment of a system containing a neurostimulator and a transceiver according to this disclosure.

FIG. 16A shows a schematic diagram of an embodiment of a system containing a medical device and an input device according to this disclosure. FIG. 16B shows a schematic diagram of an embodiment of a system containing a neurostimulator and a reader according to this disclosure. FIG. 16C shows a schematic diagram of an embodiment of a system containing a neurostimulator and a transceiver according to this disclosure.

In particular, in FIG. 16A, a system 200A includes a housing 202, a processor 204, a memory 206, a medical device 208, and an input device 210. The system 200A is energized via an energy source, such as a rechargeable or single-use battery, a mains energy line, a photovoltaic cell, a fluid turbine, or others. For example, when the system 200A is energized via the battery, then the battery can be positioned interior or exterior to the housing 202, yet securely supported via the housing 202 (e.g., fastening, mating, interlocking, adhering, hook-and-looping). For example, the battery can be rechargeable, whether over a wired, wireless, or waveguide connection, such as via a wireless charger housed or coupled to the housing 202. Similarly, when the system 200A is energized via the mains energy line, then the system 200A includes a conductive wire (e.g., copper, aluminum) or a cable (e.g. coaxial, data communication) spanning between the housing 202 and the mains energy line, with the conductive wire or the cable being coupled (e.g., mechanically, electrically) the housing 202, such as via a plug, a socket, a junction box, a pigtail, or others, and the mains energy line, such as via a plug, a socket, a junction box, a pigtail, or others.

The housing 202 houses (e.g., internally, externally) the processor 204, the memory 206, the medical device 208, and the input device 210. The housing 202 can include plastic, metal, rubber, or others. The housing 202 can be rigid, elastic, resilient, or flexible. For example, the housing 202 can be included in or embodied as a phone, a tablet, a laptop, a phone/tablet/laptop case, a patch, an adhesive bandage, a strip, an anklet, a belt, a bracelet, a necklace, a garment, a pad, a ring, a mattress, a pillow, a blanket, a robot, a surgical instrument, a stimulator, an infusion device, or others. For example, the housing 202 can be embodied as described in U.S. Patent Application Publication 20140330336 and U.S. Pat. Nos. 8,874,205, 9,174,066, 9,205,258, 9,375,571, and 9,427,581, all of which are herein incorporated by reference for all purposes as if copied and pasted herein, such as all structures, all functions, and all methods of manufacture and use, as disclosed therein. As such, the medical device 208 can be embodied as described in U.S. Patent Application Publication 20140330336 and U.S. Pat. Nos. 8,874,205, 9,174,066, 9,205,258, 9,375,571, and 9,427,581, all of which are herein incorporated by reference for all purposes as if copied and pasted herein, such as all structures, all functions, and all methods of manufacture and use, as disclosed therein.

In some embodiments, the housing 202 includes a plurality of housings 202, where the processor 204, the memory 206, the medical device 208, and the input device 210 are distributed (e.g., internally, externally) among the housings 202 in any permutational or combinatory manner. For example, one of the housings 202 may include the processor 204, the memory 206, whereas another of the housings 202 may include the medical device 208, and the input device 210, where the one of the housings 202 and the another of the housings 202 are signally coupled to each other, such as via wiring, wireless, transceivers, waveguides, or others. For example, one of the housings 202 may include the processor 204, the memory 206, and the medical device 208, whereas another of the housings 202 may include the input device 210, where the one of the housings 202 and the another of the housings 202 are signally coupled to each other, such as via wiring, wireless, transceivers, waveguides, or others.

In some embodiments, the housing 202 is anti-tamper or includes an anti-tamper device or technique, such as via a mechanic or chemical technique. Note that anti-tamper or the anti-tamper device includes at least one of a tamper resistance, a tamper detection, a tamper response, or a tamper evidence. For example, the housing 202 can be mechanically anti-tamper via including a screw that can be operated with a non-standard bit. For example, the housing 202 can be chemically anti-tamper via including a tamper evident seal.

The processor 204 is coupled to the memory 206, the medical device 208, and the input device 210, such as via wiring, wireless, transceivers, waveguides, or other wireless or wired coupling methods. The processor 204 can include a single core or multicore processor. The processor 204 can be included in or be a controller, such as a programmable logic controller (PLC) or others. The processor 204 can be distinct from the medical device 208 or be a component of the medical device 208.

The memory 206, whether volatile or non-volatile, is at least one of a mechanical memory, such as a punch card or others, or a semiconductor memory, such as a flash memory or others. The memory 206 can be distinct from the medical device 208 or be a component of the medical device 208. The memory 206 can receive, such as via a physical recordation, a wired or wireless connection, or others, and store a logic, such as projections, depressions, holes, modules, objects, programs, apps, firmware, microcode, or other forms of instruction, for execution via the processor 204. For example, the logic can be programmed or input via a (1) a manufacturer of the system 200A, (2) a distributor of the system 200A, (3) a retailer of the system 200A, (4) a wholesaler of the system 200A, or (5) a user of the system 200A, such as a medical service provider, a patient, or others. For example, a pharmacist can receive the system 200A programmed for use with a specific medical condition, disease, or disorder or a specific dosage or a specific patient or the pharmacist can receive the system 200A without being programmed for use with a specific medical condition, disease, or disorder or a specific dosage or a specific patient and then the pharmacist can program for use with a specific medical condition, disease, or disorder or a specific dosage or a specific patient, as disclosed herein. For example, a pharmacist or assistant thereof can program, such as over a wired or wireless connection, the logic via a pharmacy electronic terminal, which can include an electronic payment device, such as a payment card reader, a mobile phone wallet reader, a currency input device, a bill acceptor, a cash register, or others, or via a point-of-sale (POS) system, which may include some, most, or all of the foregoing, and can be positioned in a customer interaction area or a back pharmacy or restricted personnel area, or others. Such programming can include input or modification of (1) patient identification information, such as personal information, biometrics (e.g., fingerprint, retina scan), or others, (2) medical condition, disease, or disorder type, (3) prevention, diagnosis, monitoring, amelioration, or treatment information, such as medical device operation parameters, such as dosages, timing, or others. For example, the logic can be executed via the processor 204, such as to authenticate users, to use or to track use of the medical device 208 for at least one of prevention, diagnosis, monitoring, amelioration, or treatment, to modify prescription data, to switch the medical device 208 between a plurality of modes, to communicate with other devices, accessories, peripherals, to reconfigure, retrofit, or update the medical device 208, or others.

The memory 206 also stores a first content, such as an activation code, a set of prescription data, a set of dosage/frequency of use data, or others, that is associated with the medical device 208, such as uniquely or others. For example, the first content can include a content (e.g., barcode, text, image, sound) that is unique with respect to other similar medical devices 208, such as a serial number, a device identifier, a device parameter, or others, or a plurality of medical devices listed in a database, as disclosed herein. The first content can be stored internal or external to the logic stored in the memory 206. The first content can be of any type, such as an alphanumeric, an image, a barcode, a sound, a data structure, a projection, a depression, a hole, or any others. The first content can be formatted in any manner, such as binary, denary, hexadecimal, or others.

The medical device 208 can include one or more sensors, such as, for example, biosensors, feedback sensors, chemical sensors, optical sensors, acoustic sensors, vibration sensors, motion sensors, fluid sensors, radiation sensors, temperature sensors, motion sensors, proximity sensors, fluid sensors, or others. The one sensor can be used to sense and detect various properties, conditions and/or characteristics or variations to same or lack thereof. The sensor may generate an output, such as one or more outputs, which are communicated, via wire, wirelessly or waveguide, to the medical device 208, a base station, processor, server, or other logic or computing device. The output may be used as an input to one or more of the foregoing devices to forecast or avert an imminent onset or predicted upcoming onset of a symptom, episode, condition or disease. For example, as disclosed in U.S. Patent App. Pub. No. 2017/0120052, which is incorporated herein by reference in its entirety for at least these purposes as if copied and pasted herein, as disclosed herein, and for all purposes as if copied and pasted herein, such as all structures, all functions, and all methods of manufacture and use, as disclosed therein.

The medical device 208 can be configured to output an energy via an energy source of the medical device 208, such as a mechanical energy via an actuation source (e.g., actuator) of the medical device 208, an electrical energy via a current or voltage source (e.g., electrode) of the medical device 208, an electromagnetic energy via an impulse source (e.g., generator) of the medical device 208, a thermal energy via a heating (e.g., heating element) or cooling (e.g., ice pack, fan) source of the medical device 208, an acoustic energy via an acoustic source (e.g., speaker, transducer) of the medical device 208, or a light energy via a light source (e.g., bulb, laser beam generator) of the medical device 208. For example, as shown in FIG. 1B, the medical device 208 can include a neurostimulator 208B, whether invasive, non-invasive, or hybrid. For example, the neurostimulator 208B can be embodied as described in US Patent Application Publication 2014/0330336 and U.S. Pat. Nos. 8,874,205, 9,037,247, 9,174,066, 9,205,258, 9,375,571, and 9,427,581, all of which are herein incorporated by reference for all purposes as if copied and pasted herein, such as all structures, all functions, and all methods of manufacture and use, as disclosed therein. For example, the neurostimulator can modulate central or peripheral nervous systems. For example, the neurostimulator can be enable spinal cord stimulation to provide therapy for intractable pain and refractory angina; occipital nerve stimulation to provide therapy for occipital neuralgia and transformed migraine; afferent vagus nerve modulation to provide therapy for a host of neurological and neuropsychiatric disorders, such as epilepsy, depression, Parkinson's disease, bulimia, anxiety/obsessive compulsive disorders, Alzheimer's disease, autism, and neurogenic pain; efferent vagus nerve stimulation for rate control in atrial fibrillation, and to provide therapy for congestive heart failure; gastric nerves or gastric wall stimulation to provide therapy for obesity; sacral nerve stimulation to provide therapy for urinary urge incontinence; deep brain stimulation to provide therapy for Parkinson's disease, and other neurological and neuropsychiatric disorders; cavernous nerve stimulation to provide therapy for erectile dysfunction. However, as explained herein, note that the medical device 208 can be of any type or modality for at least one of prevention, diagnosis, monitoring, amelioration, or treatment of a medical condition, disease, or a disorder of a patient. For example, the medical device 208 can be configured to output a fluid, such as a liquid, a suspension, or a gas. For example, the medical device 208 can be configured to output a gel, a powder, or a foam. For example, the medical device 208 can be configured to increase or decrease pressure or provide physical support, whether internal or external to a patient. An example of a device that can be used is a mechanical actuator, vibration device, piezoelectric device, electric motor (e.g., brushed, brushless) or engine (e.g., combustion) or any other force generator, applicator, or output device.

The medical device 208 can operate in a first manner during the first mode and in a second manner in the second mode, where the first manner is different from or identical to the second manner, such as in an amount of operation, in an intensity of operation, in a duration of operation, in a modality of operation, in an energy use of operation, or others. For example, when the processor 204 switches the medical device 208 from the first mode (e.g., a deactivated mode) to the second mode (e.g., an activate mode), then such switching can activate the medical device 208 for a specific time period or a number of diagnosis or treatment doses or other parameters or vice versa. For example, the amount of operation includes a number of individual doses of at least one of diagnosis or treatment doses, such as less than or more than 3 doses, 4 doses, 5 doses, 6 doses, 7 doses, 8 doses, 9 doses, 10 doses, 15 doses, 20 doses, 25 doses, 30 doses, 40 doses, 45 doses, 50 doses, 60 doses, 65 doses, 70 doses, 75 doses, 80 doses, 85 doses, 90 doses, 95 doses, 100 doses, 200 doses, 300 doses, 400 doses, 500 doses, 600 doses, 700 doses, 800 doses, 900 doses, 1000 doses, or any other amount of doses from 1 to 1000 or greater, or others, whether a dose is based on a single use or a set of uses within a predefined time period (e.g., milliseconds, seconds, minutes, hours, days, weeks, months, years). As such, the medical device 208 can be adjusted where the first mode and the second mode can be equal or unequal in amount of doses.

Similarly, the intensity of operation includes a degree or type of intensity with which the medical device 208 at least one of prevents, diagnoses, monitors, ameliorates, or treats the medical condition, disease, or the disorder in the patient. For example, the first mode can be associated with a first prevention, diagnosis, monitoring, amelioration, or treatment signal/energy output and the second mode can be associated with a second prevention, diagnosis, monitoring, amelioration, or treatment signal/energy output, wherein the first signal/energy output is identical to or differs from the second signal/energy output in various parameters, such as a content, a format, an amplitude, a frequency, a time period, or others. As such, the medical device 208 can be adjusted to more intensely or less intensely prevent, diagnose, monitor, ameliorate, or treat based on switching between the first mode and the second mode. Likewise, the duration of operation includes a number of defined time periods during which the medical device can at least one of prevent, diagnose, monitor, ameliorate, or treat, such as a number of seconds, minutes, hours, days, weeks, months, or others, whether dependent on usage or independent of usage. As such, the medical device 208 can be adjusted to a least one of prevent, diagnose, monitor, ameliorate, or treat between a first defined time period and a second defined time period.

The input device 210 is configured to obtain, such as via reading, copying, or others, a second content from a storage medium, such as a magnetic card, a radio frequency identification (RFID) card, a chip card, a barcode, a Quick Response (QR) code, or others, such that the processor 204 switches the medical device 208 between the first mode and the second mode based on the first content corresponding to the second content, such as logically or others, or vice versa. The second content, such as an activation code, a set of prescription data, a set of dosage/frequency of use data, or others, can be associated with the medical device 208, such as uniquely or others, with a specific mode of operation, such as for preventing, diagnosing, monitoring, ameliorating, or treating a specific medical condition, disease, or disorder, or with a particular user, such as based on a user identifier, such as a personal identification number (PIN), a biometric, or others. Note that the particular user can be associated with the medical device 208, such as via a primary key of a relational database, as disclosed herein. For example, the primary key can be the PIN or another set of data such that the second content is unique to the particular user. In some embodiments, where the medical device 208 is shared among a plurality of users, the second content can be unique to one of the users, yet access control or authentication between the users can be controlled via another layer or form of identification, such as passwords, biometrics, or others, such as when the system 200A includes a user input device coupled to the processor 204. For example, the user input device can include a keyboard or dial, whether physical, virtual (e.g., display), or haptic (e.g., display), a biometric reader, a fob or tag, a barcode, or others.

The second content can be of any of type, whether identical to or different from the first content, such as an alphanumeric, an image, a barcode, a sound, a data structure, a projection, a depression, a hole, or any others. The second content can be formatted in any manner, whether identical to or different from the first content, such as binary, denary, hexadecimal, or others.

The input device 210 can be of any modality or type, such as a camera, a microphone, a sensor, a card reader, a signal receiver, or others. For example, as shown in FIG. 16B, the input device 210 includes a reader 210B, such as a reader terminal, that is configured to read the second content from the storage medium, such as a card, a display, an interface, a chip, a memory dongle, a paper, or others, whether the storage medium is in or out of a line-of-sight of the reader 210B. For example, when the storage medium is a card, which can include paper, cardboard, plastic, rubber, metal, wood, or others, and the reader 210B is a card reader, then the card can be embedded with at least one of a barcode, a magnetic strip, a computer chip, or another storage medium and the card reader can read the at least one of the barcode, the magnetic strip, the computer chip, or another storage medium. For example, the memory dongle can include a Universal Serial Bus (USB) dongle, a CompactFlash (CF) card, Secure Digital (SD) card, a MultiMediaCard (MMC) card. Therefore, the card can be a dumb card, a smart card, a memory card, a Wiegand card, a proximity card, or others, whether contact or contactless. Correspondingly, the reader 210B can be a smart card reader, a memory card reader, a Wiegand card reader, a magnetic stripe reader, a proximity reader, or others, whether the reader 210B is a non-intelligent reader, a semi-intelligent reader, or an intelligent reader. The input device 210 can be distinct from the medical device 208 or be a component of the medical device 208. The memory 206 can include the storage medium (e.g., removable memory chip) or vice versa. The memory 206 can exclude the storage medium or vice versa.

Similarly, as shown in FIG. 16C, the input device 210 includes a transceiver 210C, which includes a receiver, that is configured to receive, whether over a wired, wireless, or waveguide connection, the second content from the storage medium, such a card, a phone, a tablet, a laptop, a wearable, or others, such via a radio technique, an optical technique, an acoustic technique, or others, whether the storage medium is in or out of a line-of-sight of the transceiver 210C. For example, the radio technique can include a RFID interrogation, a Wi-Fi communication, a Bluetooth communication, or other radio communication formats, which can be encrypted or unencrypted. For example, the optical technique can include a laser beam, an infrared beam, a Li-Fi connection, or others. Note that the transceiver can include a transmitter or a receiver.

The input device 210 can obtain the second content from the storage medium in various ways. For example, the input device 210 can obtain the second content electronically, optically, electromagnetically, mechanically, or others, whether the storage medium is in or out of a line-of-sight of the input device 210. For example, when the input device 210 is the reader 210B, then the input device 210 can read the second content from the storage medium based on at least one of a barcode of the storage medium (optically), a QR code of the storage medium (optically), a magnetic material of the storage medium (electromagnetically), a chip of the storage medium (electromagnetically), an integrated circuit of the storage medium (electronically), a non-volatile memory of the storage medium (electronically), a punched hole of the storage medium (mechanically), a tactile surface of the storage medium (mechanically), or others. Likewise, when the input device 210 is the transceiver 210C, then the input device 210 can read the second content from the storage medium via an RFID technique, such as via interrogation, whether the storage medium is passive or active. Note that in some embodiments, the input device 210 includes the reader 210B and the transceiver 210C.

The first content can correspond to the second content in various ways, such as logically, such as via a Boolean logic, or others. For example, the first content can match the second content in content, format, logic, parameters, encryption, or others. For example, the first content can be equal to the second content, whether in format or value. Similarly, the first content can be unequal to the second content, whether in format or value. Likewise, the first content can logically map to the second content, such as via a logical symmetry where the first content is same as the second content or where the first content is different from the second, but related in a relatively quick computational way. For example, such correspondence can be determined based on or via hashing the first content or the second content. In some embodiments, processor 204 or the input device 210 can convert the first content or the second content before determining whether the first content corresponds to the second content. For example, such conversion can involve a format or a content of the first content or the second content.

When the first content does not correspond to the second content, such as the first content does not match the second content in value and format or others, as described above, then the medical device 208 is not switched from the first mode, such as a deactivated mode, to the second mode, such as an activated mode. In some embodiments, when the first content does not correspond to the second content, then the medical device 208 is switched from the first mode to the second mode, but the second mode is as or less operational than the first mode. For example, the second mode is a default mode of operation, a minimal mode of operation, a demo mode of operation, a disabled mode of operation, a kiosk mode of operation, or others.

In some embodiments, the system 100 includes an output device, such as a signal transmitter, a light, sound, or vibration source, an actuator, a data writer, or others, coupled to the processor 204, whether over a wired, wireless, or waveguide connection, where the processor 204 is configured to instruct the output device to interface with the storage medium in response to the input device 210 reading the second content. For example, the output device can include a transmitter and the processor 204 can instruct the transmitter to send a signal to the storage medium such that the storage medium can receive and process the signal, which may involve acting based on such processing. For example, such action can allow deactivating the storage medium based on or after the medical device 208 is switched from the first mode, such as a deactivated mode, to the second mode, such as an activated mode. For example, the processor 204 can request the output device to interface with the storage medium such that the storage medium is locked from further reading, when the storage medium is enabled for such locking. Similarly, the processor 204 can request the output device to interface with the storage medium such that the second content on the storage medium is rendered unusable, when the storage medium is enabled for such data modification rights. Likewise, the processor 204 can request the output device to interface with the storage medium such that the second content on the storage medium is erased from the storage medium, whether temporarily or permanently, when the storage medium is enabled for such data modification rights. Also, the processor 204 can request the output device to interface with the storage medium such that the storage medium is reformatted, when the storage medium is enabled for such data modification rights. Additionally, the processor 204 can request the output device to interface with the storage medium such that the storage medium is modified from a first state to a second state, when the storage medium is enabled for such state modification rights, and where the first state is before the input device 210 obtains the second content from the storage medium, and where the second state is after the input device 210 obtains the second content from the storage medium. Note that such interfacing can include electronically or physically modifying the storage medium or a content or data format thereon. Note that the first state and the second state can differ from each other in various ways (e.g., more or less functionality, more or less energy use, more or less data reading or modification or deletion or reformatting rights). As such, the output device can be useful to lock or wipe the storage medium once the input device 210 reads the second content from the storage medium.

When the system 200A is used to at least one of prevent, diagnose, monitor, ameliorate, or treat the medical condition, disease, or the disorder of the patient, the processor 204 tracks such use and can take an action when a predetermined threshold is satisfied or not satisfied, such as via the logic stored via the memory 206. For example, the logic tracks a use of the medical device 208 and when a number of uses, as programmed in advance, satisfies or does not satisfy the predetermined threshold, then the processor 204 can take an action, such as switch the medical device 208 between the first mode, such as an activated mode, and the second mode, such as a deactivated mode, or vice versa. Note that the logic has access to or can modify the predetermined threshold. Further, note that the predetermined threshold can be based on a number of single uses within a predefined time period (e.g., within a day, a week, a month, a year) or a number of single uses regardless of any time limit. For example, the action can include activating the medical device 208, deactivating the medical device 208, creating, modifying, or deleting a prevention, diagnosis, monitoring, amelioration, or treatment parameter of the medical device 208, as stored via the medical device 208 or the memory 206, creating, modifying, or deleting a set of treatment instructions of the medical device 208, as stored via the medical device 208 or the memory 206, or others.

In one mode of operation, a user of the system 200A positions the storage medium in proximity thereof, such as within about ten feet or less. The input device 210 interfaces with the storage medium such that the processor 204 switches the medical device 208 between the first mode and the second mode. If the first mode was a deactivated mode and the second mode was an activated mode, then the user can use the system 200A to prevent, diagnose, monitor, ameliorate, or treat the medical condition, disease, or the disorder of the user or another. For example, the input device 210 can read the second content from the storage medium and pass the second content to the processor 204. In response, the processor 204 can confirm that the first content, which is uniquely associated with the medical device 208, matches the second card, such as via value and format. Upon such confirmation, the processor 204 switches the medical device 208 from the first mode to the second mode.

Figure 17:
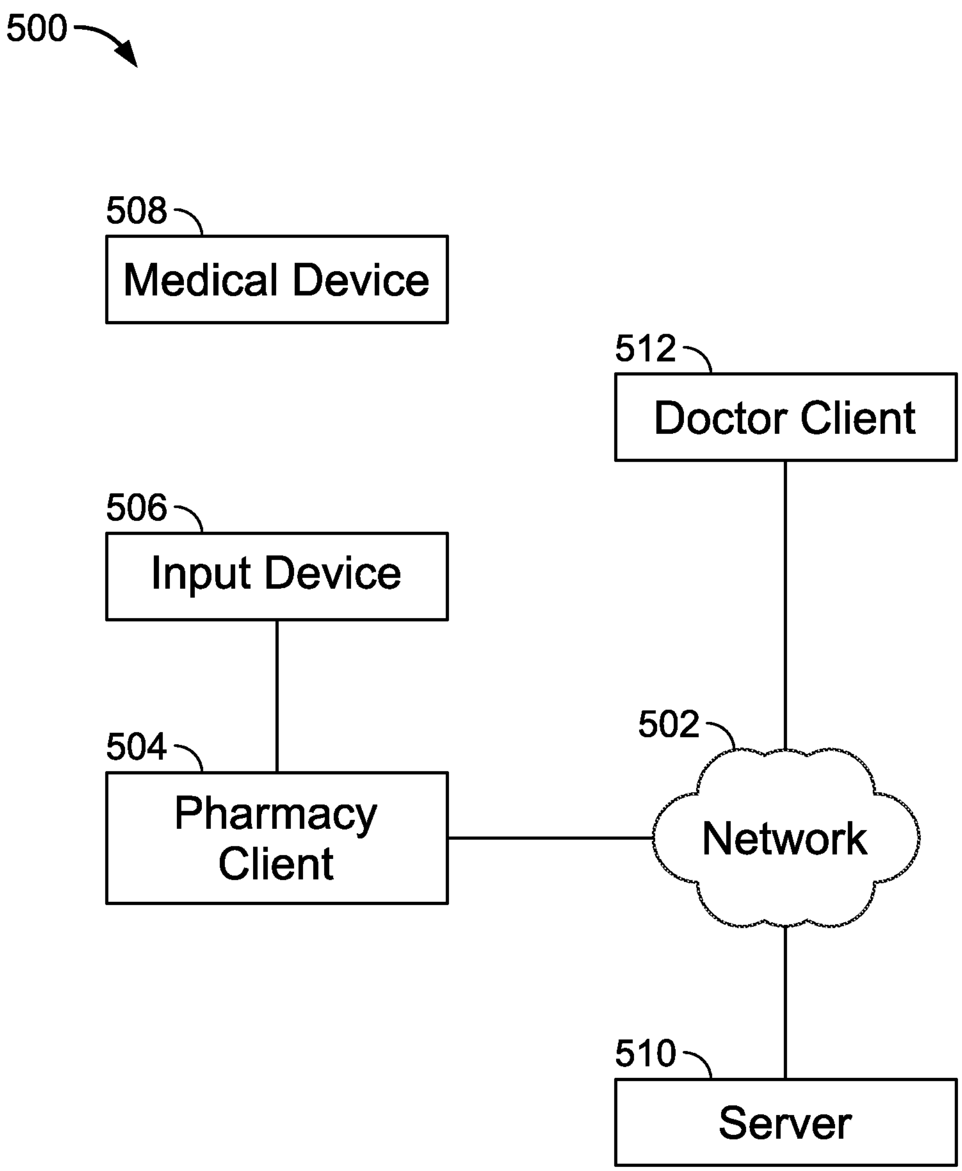
FIG. 17 is a schematic diagram of an embodiment of a network diagram for initially provisioning and refilling a system containing a medical device according to this disclosure.
Figure 18:
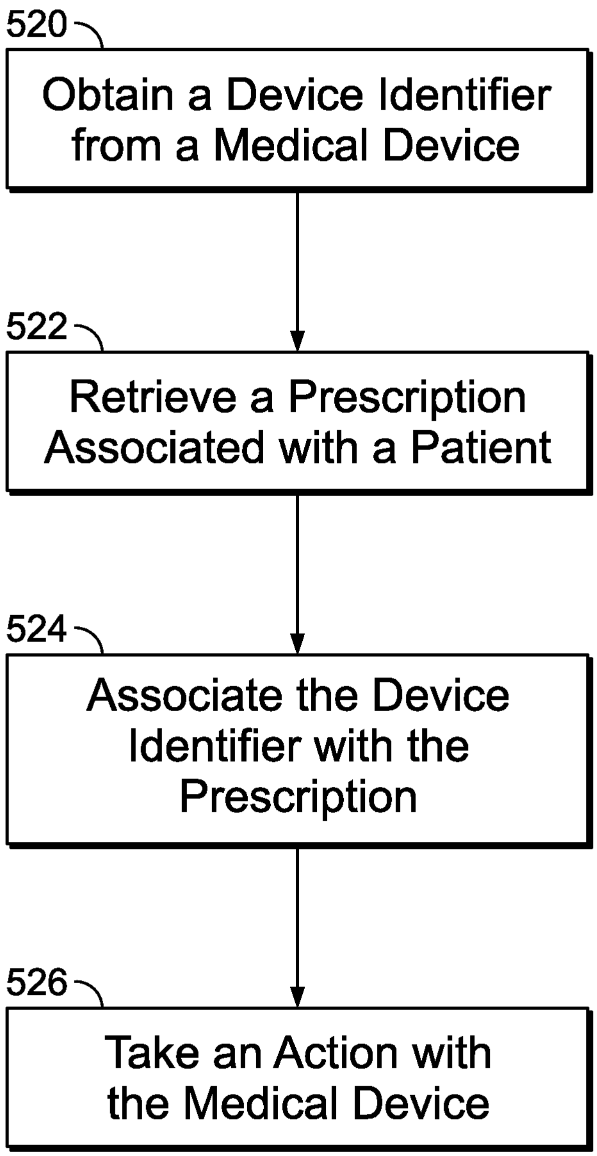
FIG. 18 is a flowchart of an embodiment of a method for initially provisioning a system containing a medical device according to this disclosure.

FIG. 17 shows a schematic diagram of an embodiment of a network diagram for initially provisioning and refilling a system containing a medical device according to this disclosure. FIG. 18 shows a flowchart of an embodiment of a method for initially provisioning a system containing a medical device according to this disclosure. In particular, a system 500 includes a network 502, a pharmacy client 504, an input device 506, a medical device 508, a server 510, and a doctor client 512. The network 502 is in communication, whether over a wireless, wired, or waveguide connection, with the pharmacy client 504, the server 510, and the doctor client 512. The pharmacy client 504 is in communication, whether over a wireless, wired, or waveguide connection, with the input device 506 and the network 502.

The network 502 includes a plurality of nodes that allow for sharing of resources or information. The network 502 can be wired or wireless. For example, the network 502 can be a local area network (LAN), a wide area network (WAN), a cellular network, a satellite network, or others.

Each of the pharmacy client 504 and the doctor client 512 is a workstation that runs an operating system, such as MacOS®, Windows®, or others, and an application, such as an administrator application, on the operating system. The workstation can include and/or be coupled to, whether directly and/or indirectly, an input device, such as a mouse, a keyboard, a camera, whether forward-facing and/or back-facing, an accelerometer, a touchscreen, a biometric reader, a clicker, a microphone, a barcode or QR code reader, or any other suitable input device. The workstation can include and/or be coupled to, whether directly and/or indirectly, an output device, such as a display, a speaker, a headphone, a printer, or any other suitable output device. In some embodiments, the input device and the output device can be embodied in one unit, such as a touch-enabled display, which can be haptic. As such, the application presents a graphical user interface (GUI) configured to interact with a user to perform various functionality, as disclosed herein. In some embodiments, the application on the pharmacy client 504 can operate in an administrator mode and a kiosk mode, such as an agent mode or others, where the administrator mode has more or higher access privileges than the kiosk mode, where the kiosk mode is used for programming the medical device 508 or coupling the medical device 508 to the storage medium, as disclosed herein. Note that the application on the pharmacy client 204 can control access between the administrator mode and the kiosk mode via user identifiers, passwords, biometrics, or others. Further, note that at least one of the pharmacy client 204 or the doctor client 212 can be a non-workstation computer as well, such as a smartphone, a tablet, a laptop, a wearable, an eyewear unit, or others.

The server 510 runs an operating system, such as MacOS®, Windows®, or others, and an application, such as a prescription management application, on the operating system. In some embodiments, the server 510 hosts or has access to a database, such as a relational database, an in-memory database, a graphical database, a NoSQL database, or others. For example, the database can include a plurality of records, where each of the records contains a plurality of fields associated with a plurality of categories, such as patient identifier, patient contact information, patient medical record, prescription name, prescription dosage, and others. Note that the database can include or be coupled to an electronic medical records (EMR) database, whether local or remote thereto, whether using a same or different schema (e.g., star, tree). The server 510 can include and/or be coupled to, whether directly and/or indirectly, an input device, such as a mouse, a keyboard, a camera, whether forward-facing and/or back-facing, an accelerometer, a touchscreen, a biometric reader, a clicker, a microphone, or any other suitable input device. The server 510 can include and/or be coupled to, whether directly and/or indirectly, an output device, such as a display, a speaker, a headphone, a printer, or any other suitable output device. In some embodiments, the input device and the output device can be embodied in one unit, such as a touch-enabled display, which can be haptic.

The input device 506 is coupled to the pharmacy client 504, whether over in a wired, wireless, or waveguide connection, and can include a camera, a microphone, a keyboard, whether physical or virtual, a reader, or others. The input device 504 can be battery energized or energized via the pharmacy client 504.

The medical device 208, such as the system 200A, the medical device 208, or others, comprises a device identifier, such as the first content, as disclosed herein, whether internally, such as via the memory 206 or others, or externally, such as on the medical device 208 itself, on a tag coupled to the medical device 208, such as via adhering, fastening, mating, or others, or on a tag coupled to or depicted or printed on a package containing the medical device 208.

In one mode of operation, as shown in FIG. 18, in order to initially provision the medical device 508, the doctor client 512 sends a set of prescription data to the server 510 over the network 502. As per block 522, the pharmacy client 504 retrieves (e.g., reads, copies) the set of prescription data from the server 510 over the network 502, such as via a patient identifier associated with a record of the database accessible to the server 510. Upon retrieval, the pharmacy client 504 displays the set of prescription data thereon.

As per block 520, a user of the pharmacy client 504 uses the input device 506 to obtain the device identifier from the medical device 508. For example, when the device identifier, such as the first content, is internal to the medical device 508, then the input device 506 can interface with the medical device 508, whether over a wired, wireless, or waveguide connection, and obtain the device identifier, such as via an RFID interrogation or others. Likewise, when the device identifier is external to the medical device 508, then the input device 206 obtains the device identifier via reading the device identifier, such as via barcode or QR code scanning or others. Note that the block 520 can occur before, during, or after the block 522. As such, once the pharmacy client 504 has the device identifier and the set of prescription data, as per block 524, the pharmacy client 504 associates the device identifier and the set of prescription data, whether locally or on the server 510, such as via relating the device identifier and the set of prescription data in the database, such as via a primary key or others. Therefore, as per block 526, an action can be taken with the medical device 508. For example, the action can be via the pharmacy client 510 prompting a message that the medical device 508 is associated with the set of prescription data, generating a sound alert, modifying a data structure, or others. Similarly, the action can include packaging or repackaging the medical device 508, shipping the medical device 508, handing over the medical device 508 to a patient, or others.

Figure 19:
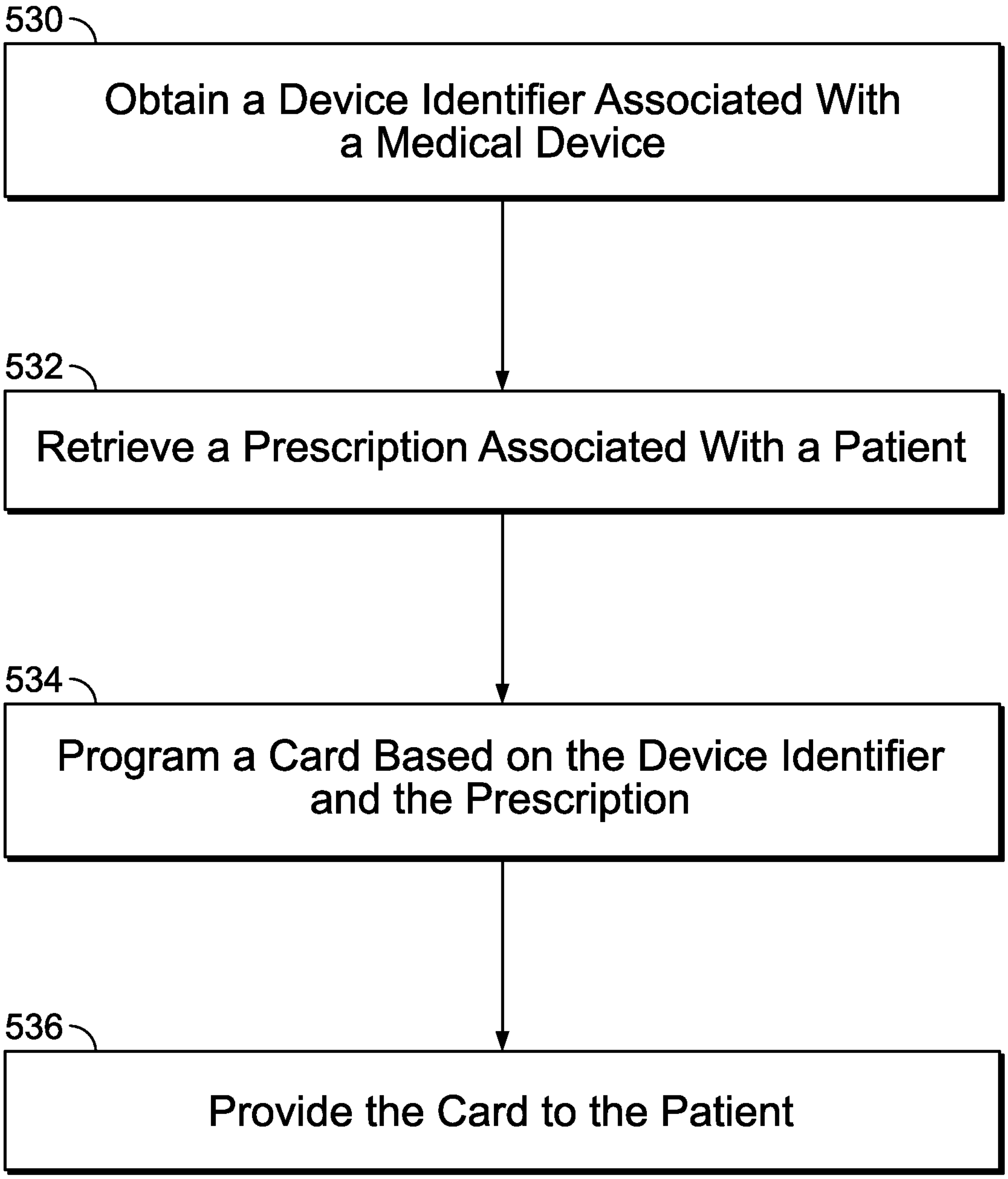
FIG. 19 is a flowchart of an embodiment of a method for refilling a system containing a medical device according to this disclosure.

FIG. 19 shows a flowchart of an embodiment of a method for refilling a system containing a medical device according to this disclosure. In particular, in order to refill the medical device 508, the doctor client 512 sends a set of prescription data to the server 510 over the network 502. As per block 532, the pharmacy client 504 retrieves (e.g., reads, copies) the set of prescription data from the server 510 over the network 502, such as via a patient identifier associated with a record of the database accessible to the server 510. Upon retrieval, the pharmacy client 504 displays the set of prescription data thereon.

As per block 530, a user of the pharmacy client 504 uses the input device 506 to obtain the device identifier from the medical device 508. For example, when the device identifier, such as the first content, is internal to the medical device 508, then the input device 506 can interface with the medical device 508, whether over a wired, wireless, or waveguide connection, and obtain the device identifier, such as via an RFID interrogation or others. Likewise, when the device identifier is external to the medical device 508, then the input device 506 obtains the device identifier via reading the device identifier, such as via barcode or QR code scanning or others. Note that the block 530 can occur before, during, or after the block 532.

As such, once the pharmacy client 504 has the device identifier and the set of prescription data, as per block 534, the pharmacy client 504 can be used to program or reprogram a storage medium, such as an RFID card or others, based on the set of prescription data, via an output device, such as a signal transmitter, a light, sound, or vibration source, an actuator, a data writer, or others, coupled to the pharmacy client 504, whether over a wired, wireless, or waveguide connection. For example, such programming can be via an RFID interrogation or other technologies. For example, such programming can involve using the pharmacy client 504 to program the storage medium to match the device identifier that is uniquely associated with the medical device 508. For example, the pharmacy client 504 can instruct the output device to interface with the storage medium, such as via adding, modifying, or deleting content or format to or from the storage medium such that the storage medium stores the set of prescription data or a logic containing a set of instructions to operate the medical device 508 according to the set of prescription data. Note that this logic can be included in the set of prescription data or generated via the server 510 or the pharmacy client 504 based on the set of prescription data. In some embodiments, the medical device 508 generates this logic based on the set of prescription data as obtained from the storage medium. Therefore, the storage medium can be positioned in proximity (e.g., within about 10 feet or less) of the system 200A to be read via the input device 510 such that the processor 504 can switch the medical device 508 between the first mode and the second mode. Note that for recordkeeping purposes, the pharmacy client 504 can communicate (e.g., email, texting, social networking, over-the-top) a message informative of such programming to the server 510 over the network 502, such as for writing into the record of the patient in the database. For example, the pharmacy client 504 associates the device identifier and the set of prescription data, whether locally or on the server 510, such as via relating the device identifier and the set of prescription data in the database, such as via a primary key or others.

Consequently, as per block 536, the storage medium, as programmed, can be provided to the patient, such as via handing over to the patient, packaging/shipping to the patient, or communicating to the patient, such as via email, text, social networking, over-the-top messaging, or others. As such, a POS terminal, such as the pharmacy client 504, can be used to (1) obtain a device identifier from the medical device 508, (2) retrieve a set of prescription data from the server 510, where the device identifier is uniquely associated with the medical device 508, and (3) program, such as via encoding or others, a storage medium, such as an RFID card or others, based on the device identifier and the set of prescription data such that the medical device 508 can be switched from a first mode, such as a deactivated mode, to a second mode, such as an activated mode, or load a set of new therapy dose data, based on the storage medium being in proximity of the medical device 508.

In some embodiments, the output device can include a transmitter (e.g., wired, wireless, waveguide) and the pharmacy client 504 can instruct the transmitter to send (e.g., wired, wireless, waveguide) a signal to the storage medium such that the storage medium can receive and process the signal, which may involve acting based on such processing. For example, the pharmacy client 504 can request the output device to interface with the storage medium such that the storage medium is locked from further reading or writing or modifying or deleting, whether in data or format, when the storage medium is enabled for such locking. Similarly, the pharmacy client 504 can request the output device to interface with the storage medium such that the second content on the storage medium is rendered unusable, when the storage medium is enabled for such data modification rights. Likewise, the pharmacy client 504 can request the output device to interface with the storage medium such that the second content on the storage medium is erased from the storage medium, whether temporarily or permanently, when the storage medium is enabled for such data modification rights. Also, the pharmacy client 504 can request the output device to interface with the storage medium such that the storage medium is reformatted, when the storage medium is enabled for such data modification rights. Note that such interfacing can include electronically or physically modifying the storage medium or a content or data format thereon or an encryption thereon.

Figure 20:
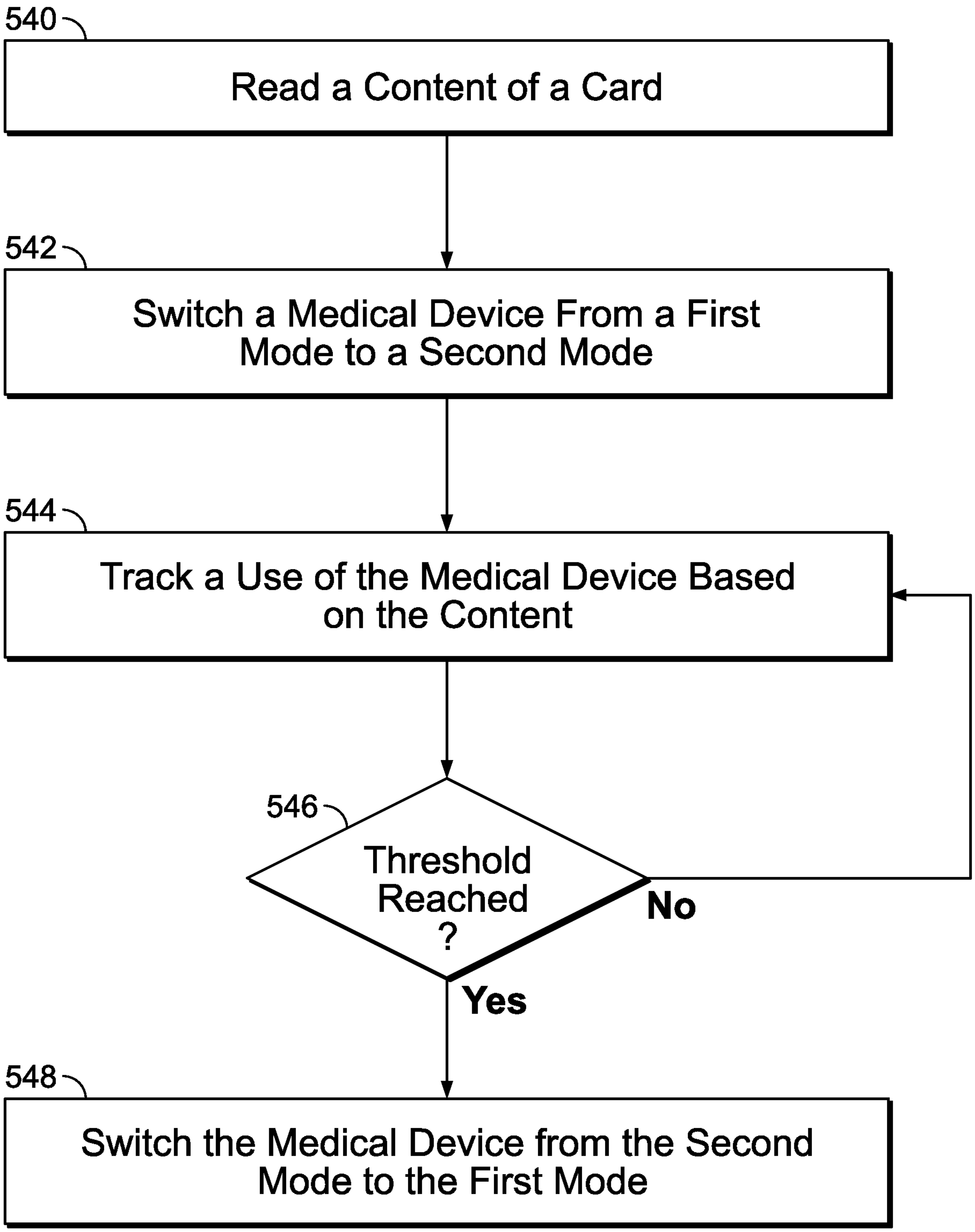
FIG. 20 is a flowchart of an embodiment of a method for using a system containing a medical device according to this disclosure.

FIG. 20 shows a flowchart of an embodiment of a method for using a system containing a medical device according to this disclosure. In particular, as per block 540, a storage medium, such as an RFID card or others, is positioned in proximity of the input device 510, such as an RFID reader, such that the input device 510 can read a content of the storage medium. For example, the content can include an activation code and a set of prescription data, such as a therapy dosage or others. For example, such reading can occur at a patient location such as at home, at work, or others, at a pharmacy location, such as at a retail kiosk or others, at a manufacturer location, such as at a warehouse or others, or others. As per block 544, responsive to such reading, the processor 504 switches the medical device 508 from a first mode, such as a deactivated mode, to a second mode, such as an activated mode. In some embodiments, the processor 504 instructs the output device of the system 200A to communicate with the storage medium in order to deactivate the storage medium, as disclosed herein, such as via deleting the content from the storage medium, reformatting the card, or others. As per block 544, the processor 504 tracks usage of the medical device 508 in order to be compliant with the content of the storage medium as read by the input device 510. For example, if the content mandates 1 use during 24 hours for 1 week, then the processor 504 track time, days, and usage per day or another time period (e.g., minutes, hours). As per block 544, if the processor 504 determines that the usage of the medical device has reached a predetermined threshold, as per the content read from the storage medium, then the processor 504 switches the medical device 508 from the second mode (the activated mode) to the first mode (the deactivated mode), otherwise the processor 504 allows the usage of the medical device 508. For example, if the content mandates 1 use during 24 hours for 1 week, then the processor 504 switches the medical device 508 from the second mode to the first mode when 1 week from first use of the medical device 508 passed.

A more complete description of systems and methods of using medical device 208 can be found in commonly-assigned, co-pending U.S. patent application Ser. No. 16/229,299, filed Dec. 21, 2018, the complete disclosure of which is incorporated herein by reference for all purposes.

Various corresponding structures, materials, acts, and equivalents of all means or step plus function elements in various claims below are intended to include any structure, material, or act for performing the function in combination with other claimed elements as specifically claimed. Various embodiments were chosen and described in order to best explain various principles of this disclosure and various practical applications thereof, and to enable others of ordinary skill in a pertinent art to understand this disclosure for various embodiments with various modifications as are suited to a particular use contemplated.

Various diagrams depicted herein are illustrative. There can be many variations to such diagrams or steps (or operations) described therein without departing from various spirits of this disclosure. For instance, various steps can be performed in a differing order or steps can be added, deleted or modified. All of these variations are considered a part of this disclosure. People skilled in an art to which this disclosure relates, both now and in future, can make various improvements and enhancements which fall within various scopes of various claims which follow.

The invention claimed is:

1. A method for maintaining telomere lengths of a patient, the method comprising:

positioning an electrode of a device in contact with an outer skin surface of a neck of a patient;

applying, via the device, when the electrode is in contact with the outer skin surface of the neck of the patient, electrical impulses transcutaneously from the device through the outer skin surface of the patient to a vagus nerve in the patient according to a stimulation protocol that consists of applying the electrical impulses as a first single dose for a time period of about 90seconds to about three minutes, and a second single dose for a time period of about 90 seconds to about three minutes, wherein the second single dose is applied five minutes or less after the first single dose and wherein the stimulation protocol consists of apply only the first and second doses each day for a plurality of days and wherein no other electric impulses are applied to the patient during a duration of the stimulation protocol; and wherein the electric current and the stimulation protocol are sufficient to modulate the vagus nerve to increase an activity of telomerase and at least inhibit a reduction in telomere lengths in the patient.

2. The method of claim 1, further comprising attaching the electrode to the outer skin surface of the neck of the patient.

3. The method of claim 2, wherein the electrode is coupled to an energy source via one or more leads.

4. The method of claim 2, further comprising wirelessly transmitting the electrical impulses to the electrode.

5. The method of claim 2, wherein the electrode is part of a housing and wherein the energy source is housed within the housing.

6. The method of claim 1, wherein the electrical impulses comprises bursts of pulses, with each burst having a frequency of about 1 to about 100 bursts per second and each pulse has a duration of about 50 to about 1000 microseconds in duration.

7. The method of claim 6, wherein the bursts each comprise about 2 to 20 pulses and the bursts are separated by an inter-burst period that comprises zero pulses.

8. The method of claim 1, wherein the electrical impulses and the stimulation protocol are sufficient to modulate the vagus nerve to reduce a cortisol level within the patient.

9. The method of claim 1, wherein the electrical impulses and the stimulation protocol are sufficient to modulate the vagus nerve to reduce an amount of circulating cortisol within the patient.

10. The method of claim 1, wherein the electrical impulses and the stimulation protocol are sufficient to increase a healthspan of the patient.

11. The method of claim 1, further comprising attaching a patch to the outer skin surface of a neck of the patient, wherein the patch comprises one or more electrodes.

12. The method of claim 1, wherein the stimulation protocol comprises 2 to 4 treatments/day.

13. The method of claim 1, wherein the electrical impulses comprises pulses having a frequency of about 1 kHz to about 20 kHz.

14. The method of claim 1, wherein the electrical impulses are sufficient to inhibit systemic inflammation within the patient.

* * * * *